US009161991B2

(12) United States Patent
Pieczykolan et al.

(10) Patent No.: US 9,161,991 B2
(45) Date of Patent: Oct. 20, 2015

(54) ANTICANCER FUSION PROTEIN COMPRISING TRAIL AND INTERFERON

(75) Inventors: Jerzy Szczepan Pieczykolan, Radecznica (PL); Krzysztof Kazimierz Lemke, Gdynia (PL); Sebastian Pawlak, Warszawa (PL); Bartłomiej Żerek, Dąbrowa (PL)

(73) Assignee: ADAMED sp. z o. o., Czosnow k/Warszawy ( * ) Notice: Subject to any disclaimer, the term of this patent is extended or adjusted under 35 U.S.C. 154(b) by 0 days.

(21) Appl. No.: 13/989,969

(22) PCT Filed: Dec. 5, 2011

(86) PCT No.: PCT/EP2011/071719
§ 371 (c)(1),
(2), (4) Date: May 28, 2013

(87) PCT Pub. No.: WO2012/072815
PCT Pub. Date: Jun. 7, 2012

(65) Prior Publication Data
US 2013/0251676 A1 Sep. 26, 2013

(30) Foreign Application Priority Data

Dec. 3, 2010 (PL) .......................... 393146
Apr. 18, 2011 (PL) .......................... 394597

(51) Int. Cl.
*C07K 14/47* (2006.01)
*C07K 14/525* (2006.01)
*C07K 14/555* (2006.01)
*C07K 14/56* (2006.01)
*C07K 14/57* (2006.01)
*A61K 38/19* (2006.01)
*A61K 38/21* (2006.01)
*A61K 38/18* (2006.01)
*C07K 19/00* (2006.01)
*A61K 47/48* (2006.01)
*C07K 14/705* (2006.01)
*A61K 38/00* (2006.01)

(52) U.S. Cl.
CPC ........... *A61K 47/48269* (2013.01); *A61K 38/19* (2013.01); *A61K 38/191* (2013.01); *A61K 38/212* (2013.01); *A61K 38/217* (2013.01); *C07K 14/525* (2013.01); *C07K 14/56* (2013.01); *C07K 14/57* (2013.01); *C07K 14/70575* (2013.01); *A61K 38/00* (2013.01); *C07K 14/555* (2013.01); *C07K 2319/33* (2013.01); *C07K 2319/50* (2013.01); *C07K 2319/75* (2013.01)

(58) Field of Classification Search
None
See application file for complete search history.

(56) References Cited

FOREIGN PATENT DOCUMENTS

| WO | WO 01/95942 A2 | 12/2001 |
| WO | WO 02/20715 A2 | 3/2002 |
| WO | WO 2009/025846 A2 | 2/2009 |

OTHER PUBLICATIONS

Shin et al. Generation of a novel proform of tumor necrosis factor-related apoptosis-inducing ligand (TRAIL) protein that can be reactivated by matrix metalloproteases. Exp Cell Res 312: 3892-3898, 2006.*
Zerek et al. Modulation of genes expression as an effective tool for enhancing the antitumor effect of death ligands. Novel IFN-gamma-TRAIL/Apo2L fusion protein. Eur J Cancer 49 (Suppl2): S107, abstract #536, 2013.*
Pieczykolan et al. The AD-O56.9-fusion of TRAIL/Apo2L with a membrane permeable peptide as a novel anticancer therapeutic. Eur J Cancer 49 (Suppl2): S107-108, abstract #537, 2013.*
Zerek et al. AD-O64.3: IFNgamma-TRAIL fusion protein. Use of two independent signaling pathways for a strong synergistic antitumor effect. Eur J Cancer 50 (Suppl 6): p. 47, abstract # 135, 2014.*
Abdulghani et al. TRAIL receptor signaling and therapeutics. Expert Opin Ther Targets 14(10): 1091-1108, 2010.*
Ashkenazi et al. Ligand-based targeting of apoptosis in cancer: the potential of recombinant human apoptosis ligand 2/tumor necrosis factor-related apoptosis-inducing ligand (rhApo2L/TRAIL). J Clin Oncol 26(21): 3621-3630, 2008.*
Lissat et al. Interferon-gamma sensitizes resistant Ewing's sarcoma cells to tumor necrosis factor apoptosis-inducing ligand-induced apoptosis by up-regulation of caspase-8 without altering chemosensitivity. Am J Pathol 170(6): 1917-1930, 2007.*
International Search Report issued by the International Searching Authority (ISA/O.E.P.M.) on Feb. 23, 2012 in connection with International Application No. PCT/EP2011/071719.
Written Opinion of the International Searching Authority issued on Feb. 23, 2012 in connection with International Application No. PCT/EP2011/071719.
Apr. 2, 2012 Applicant's comments on Written Opinion in connection with International Application No. PCT/EP2011/071719.
Clark PE et al.: "TRAIL and Interferon-alpha Act Synergistically to Induce Renal Cell Carcinoma Apoptosis", Journal of Urology, Lippincott Williams & Wilkins, Baltimore, MD, US, vol. 184, No. 3, (2010) pp. 1166-1174.
Jeannette Gerspach et al.: "Target-selective activation of a TNF prodrug by urokinase-type plasminogen activator (uPA) mediated proteolytic processing at the cell the cell surface", Cancer Immunology, Immunotherapy, Springer, Berlin, DE, vol. 55, No. 12, (2006) pp. 1590-1600.

(Continued)

*Primary Examiner* — Bridget E Bunner
(74) *Attorney, Agent, or Firm* — Gary J. Gershik; Cooper & Dunham LLP

(57) ABSTRACT

A fusion protein comprising domain (a) which is a functional fragment of hTRAIL protein sequence, which fragment begins with an amino acid at a position not lower than hTRAIL95, or a homolog of said functional fragment having at least 70% sequence identity; and domain (b) which is a sequence of an immunostimulating effector peptide, wherein the sequence of domain (b) is attached at the C-terminus or N-terminus of domain (a). The fusion protein can be used for the treatment of cancer diseases.

19 Claims, 9 Drawing Sheets

(56) References Cited

OTHER PUBLICATIONS

Merino Delphine et al., "Trail and cancer therapy: present and future challenges.", Expert Opinion on Therapeutic Targets, vol. 11, No. 10, (2007), pp. 1299-1314.

Park S-Y et al.: "INF-Gamma Enhances Trail-induced Apoptosis Through IRF-1", European Journal of Biochemistry, Blackwell Publishing, Berlin, DE, vol. 271, No. 21, (2004) pp. 4222-4228.

Shin J N et al.: "Generation of a novel proform of tumor necrosis factor-related apoptosis-inducing ligand (TRAIL) protein that can be reactivated by matrix metalloproteinases", Experimental Cell Research, Academic Press, US, vol. 312, No. 19, (2006), pp. 3892-3898.

* cited by examiner

Ex. 12

Ex. 13

Ex. 14

Ex. 15

SEQUENCE LISTING

```
<160> NUMBER OF SEQ ID NOS: 52

<210> SEQ ID NO 1
<211> LENGTH: 345
<212> TYPE: PRT
<213> ORGANISM: Artificial Sequence
<220> FEATURE:
```

<223> OTHER INFORMATION: synthesized, fusion protein comprising: a
fragment of TRAIL protein, subunit 2b of human interferon alpha,
and fragments recognized by urokinase and metalloprotease MMP

<400> SEQUENCE: 1

| Cys | Asp | Leu | Pro | Gln | Thr | His | Ser | Leu | Gly | Ser | Arg | Arg | Thr | Leu | Met |
|---|---|---|---|---|---|---|---|--- fragment of TRAIL protein, subunit 2b of human interferon alpha, and fragments recognized by urokinase and metalloprotease MMP

<400> SEQUENCE: 2

```

-continued linker for pegylation and fragments recognized by urokinase and metalloprotease MMP.

<400> SEQUENCE: 3

| | | | | | | | | | | | | | | |
|---|---|---|---|---|---|---|---|---|---|---|---|---|---|---|
| Cys | Asp | Leu | Pro | Gln | Thr | His | Ser | Leu | Gly | Ser | Arg | Arg | Thr | Leu | Met |
| 1 | | | | 5 | | | | | 10 | | | | | 15 | |
| Leu | Leu | Ala | Gln | Met | Arg | Arg | Ile | Ser | Leu | Phe | Ser | Cys | Leu | Lys | Asp |
| | | | 20 | | | | | 25 | | | | | 30 | | |
| Arg | His | Asp | Phe | Gly | Phe | Pro | Gln | Glu | Glu | Phe | Gly | Asn | Gln | Phe | Gln |
| | | | 35 | | | | 40 | | | | | 45 | | | |
| Lys | Ala | Glu | Thr | Ile | Pro | Val | Leu | His | Glu | Met | Ile | Gln | Gln | Ile | Phe |
| | 50 | | | | | 55 | | | | | 60 | | | | |
| Asn | Leu | Phe | Ser | Thr | Lys | Asp | Ser | Ser | Ala | Ala | Trp | Asp | Glu | Thr | Leu |
| 65 | | | | | 70 | | | | 75 | | | | | 80 | |
| Leu | Asp | Lys | Phe | Tyr | Thr | Glu | Leu | Tyr | Gln | Gln | Leu | Asn | Asp | Leu | Glu |
| | | | | 85 | | | | | 90 | | | | | 95 | |
| Ala | Cys | Val | Ile | Gln | Gly | Val | Gly | Val | Thr | Glu | Thr | Pro | Leu | Met | Lys |
| | | | 100 | | | | | 105 | | | | | 110 | | |
| Glu | Asp | Ser | Ile | Leu | Ala | Val | Arg | Lys | Tyr | Phe | Gln | Arg | Ile | Thr | Leu |
| | | 115 | | | | | 120 | | | | | 125 | | | |
| Tyr | Leu | Lys | Glu | Lys | Lys | Tyr | Ser | Pro | Cys | Ala | Trp | Glu | Val | Val | Arg |
| | 130 | | | | | 135 | | | | | 140 | | | | |
| Ala | Glu | Ile | Met | Arg | Ser | Phe | Ser | Leu | Ser | Thr | Asn | Leu | Gln | Glu | Ser |
| 145 | | | | | 150 | | | | | 155 | | | | | 160 |
| Leu | Arg | Ser | Lys | Glu | Pro | Leu | Gly | Leu | Ala | Gly | Arg | Val | Val | Arg | Ala |
| | | | | 165 | | | | | 170 | | | | | 175 | |
| Ser | Gly | Cys | Gly | Pro | Glu | Pro | Leu | Gly | Leu | Ala | Gly | Arg | Val | Val | Arg |
| | | | 180 | | | | | 185 | | | | | 190 | | | linker for pegylation and fragments recognized by urokinase and metalloprotease MMP.

<400> SEQUENCE: 4

```
Arg Val Ala Ala His Ile Thr Gly Thr Arg Gly Arg Ser Asn Thr Leu
1               5                   10                  15

Ser Ser Pro Asn Ser Lys Asn Glu Lys Ala Leu Gly Arg Lys Ile Asn
            20                  25                  30

Ser Trp Glu Ser Ser Arg Ser Gly His Ser Phe Leu Ser Asn Leu His
        35                  40                  45

Leu Arg Asn Gly Glu Leu Val Ile His Glu Lys Gly Phe Tyr Tyr Ile
50                  55                  60

Tyr Ser Gln Thr Tyr Phe Arg Phe Gln Glu Glu Ile Lys Glu Asn Thr
65                  70                  75                  80

Lys Asn Asp Lys Gln Met Val Gln Tyr Ile Tyr Lys Tyr Thr Ser Tyr
                85                  90                  95

Pro Asp Pro Ile Leu Leu Met Lys Ser Ala Arg Asn Ser Cys Trp Ser
            100                 105                 110

Lys Asp Ala Glu Tyr Gly Leu Tyr Ser Ile Tyr Gln Gly Gly Ile Phe
        115                 120                 125

Glu Leu Lys Glu Asn Asp Arg Ile Phe Val Ser Val Thr Asn Glu His
130                 135                 140

Leu Ile Asp Met Asp His Glu Ala Ser Phe Phe Gly Ala Phe Leu Val
145                 150                 155                 160

Gly Pro Leu Gly Leu Ala Gly Arg Val Val Arg Ala Ser Gly Cys Gly
                165                 170                 175

Pro Glu Pro Leu Gly Leu Ala Gly Arg Val Val Arg Cys Asp Leu Pro
            180                 185                 190

Gln Thr His Ser Leu Gly Ser Arg Arg Thr Leu Met Leu Leu Ala Gln
        195                 200                 205

Met Arg Arg Ile Ser Leu Phe Ser Cys Leu Lys Asp Arg His Asp Phe
210                 215                 220

Gly Phe Pro Gln Glu Glu Phe Gly Asn Gln Phe Gln Lys Ala Glu Thr
225                 230                 235                 240

Ile Pro Val Leu His Glu Met Ile Gln Gln Ile Phe Asn Leu Phe Ser
                245                 250                 255

Thr Lys Asp Ser Ser Ala Ala Trp Asp Glu Thr Leu Leu Asp Lys Phe
            260                 265                 270

Tyr Thr Glu Leu Tyr Gln Gln Leu Asn Asp Leu Glu Ala Cys Val Ile
        275                 280                 285

Gln Gly Val Gly Val Thr Glu Thr Pro Leu Met Lys Glu Asp Ser Ile
290                 295                 300

Leu Ala Val Arg Lys Tyr Phe Gln Arg Ile Thr Leu Tyr Leu Lys Glu
305                 310                 315                 320

Lys Lys Tyr Ser Pro Cys Ala Trp Glu Val Val Arg Ala Glu Ile Met
                325                 330                 335

Arg Ser Phe Ser Leu Ser Thr Asn Leu Gln Glu Ser Leu Arg Ser Lys
            340                 345                 350

Glu
```

<210> SEQ ID NO 5
<211> LENGTH: 300
<212> TYPE: PRT
<213> ORGANISM: Artificial Sequence
<220> FEATURE:

<223> OTHER INFORMATION: synthesized, a fusion protein comprising: a
      fragment of TRAIL protein, fragment of human interferon gamma and
      fragments recognized by urokinase and metalloprotease MMP.

<400> SEQUENCE: 5

```
Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
50                  55                  60

Ser Ile Gln Lys Ser Val Glu Thr Ile Lys Glu Asp Met Asn Val Lys
65                  70                  75                  80

Phe Phe Asn Ser Asn Lys Lys Arg Asp Asp Phe Glu Lys Leu Thr
                85                  90                  95

Asn Tyr Ser Val Thr Asp Leu Asn Val Gln Arg Lys Ala Ile His Glu
                100                 105                 110

Leu Ile Gln Val Met Ala Glu Leu Ser Pro Ala Ala Pro Leu Gly Leu
            115                 120                 125

Ala Gly Arg Val Val Arg Glu Arg Gly Pro Gln Arg Val Ala Ala His
        130                 135                 140

Ile Thr Gly Thr Arg Gly Arg Ser Asn Thr Leu Ser Ser Pro Asn Ser
145                 150                 155                 160

Lys Asn Glu Lys Ala Leu Gly Arg Lys Ile Asn Ser Trp Glu Ser Ser
                165                 170                 175

Arg Ser Gly His Ser Phe Leu Ser Asn Leu His Leu Arg Asn Gly Glu
                180                 185                 190

Leu Val Ile His Glu Lys Gly Phe Tyr Tyr Ile Tyr Ser Gln Thr Tyr
            195                 200                 205

Phe Arg Phe Gln Glu Glu Ile Lys Glu Asn Thr Lys Asn Asp Lys Gln
        210                 215                 220

Met Val Gln Tyr Ile Tyr Lys Tyr Thr Ser Tyr Pro Asp Pro Ile Leu
225                 230                 235                 240

Leu Met Lys Ser Ala Arg Asn Ser Cys Trp Ser Lys Asp Ala Glu Tyr
                245                 250                 255

Gly Leu Tyr Ser Ile Tyr Gln Gly Gly Ile Phe Glu Leu Lys Glu Asn
                260                 265                 270

Asp Arg Ile Phe Val Ser Val Thr Asn Glu His Leu Ile Asp Met Asp
            275                 280                 285

His Glu Ala Ser Phe Phe Gly Ala Phe Leu Val Gly
        290                 295                 300
```

<210> SEQ ID NO 6
<211> LENGTH: 307
<212> TYPE: PRT
<213> ORGANISM: Artificial Sequence
<220> FEATURE:
<223> OTHER INFORMATION: synthesized, a fusion protein comprising: a
      fragment of TRAIL protein, fragment of human interferon gamma,
      flexible glycine-serine linkers and fragments recognized by
      urokinase and metalloprotease MMP.

<400> SEQUENCE: 6

```
Glu Arg Gly Pro Gln Arg Val Ala Ala His Ile Thr Gly Thr Arg Gly
1               5                   10                  15
```

```
Arg Ser Asn Thr Leu Ser Ser Pro Asn Ser Lys Asn Glu Lys Ala Leu
             20                  25                  30

Gly Arg Lys Ile Asn Ser Trp Glu Ser Ser Arg Ser Gly His Ser Phe
         35                  40                  45

Leu Ser Asn Leu His Leu Arg Asn Gly Glu Leu Val Ile His Glu Lys
 50                  55                  60

Gly Phe Tyr Tyr Ile Tyr Ser Gln Thr Tyr Phe Arg Phe Gln Glu Glu
 65                  70                  75                  80

Ile Lys Glu Asn Thr Lys Asn Asp Lys Gln Met Val Gln Tyr Ile Tyr
                 85                  90                  95

Lys Tyr Thr Ser Tyr Pro Asp Pro Ile Leu Leu Met Lys Ser Ala Arg
            100                 105                 110

Asn Ser Cys Trp Ser Lys Asp Ala Glu Tyr Gly Leu Tyr Ser Ile Tyr
            115                 120                 125

Gln Gly Gly Ile Phe Glu Leu Lys Glu Asn Asp Arg Ile Phe Val Ser
    130                 135                 140

Val Thr Asn Glu His Leu Ile Asp Met Asp His Glu Ala Ser Phe Phe
145                 150                 155                 160

Gly Ala Phe Leu Val Gly Gly Ser Pro Leu Gly Leu Ala Gly Arg
                165                 170                 175

Val Val Arg Gly Gly Ser Gln Asp Pro Tyr Val Lys Glu Ala Glu
            180                 185                 190

Asn Leu Lys Lys Tyr Phe Asn Ala Gly His Ser Asp Val Ala Asp Asn
        195                 200                 205

Gly Thr Leu Phe Leu Gly Ile Leu Lys Asn Trp Lys Glu Glu Ser Asp
210                 215                 220

Arg Lys Ile Met Gln Ser Gln Ile Val Ser Phe Tyr Phe Lys Leu Phe
225                 230                 235                 240

Lys Asn Phe Lys Asp Asp Gln Ser Ile Gln Lys Ser Val Glu Thr Ile
                245                 250                 255

Lys Glu Asp Met Asn Val Lys Phe Phe Asn Ser Asn Lys Lys Lys Arg
            260                 265                 270

Asp Asp Phe Glu Lys Leu Thr Asn Tyr Ser Val Thr Asp Leu Asn Val
        275                 280                 285

Gln Arg Lys Ala Ile His Glu Leu Ile Gln Val Met Ala Glu Leu Ser
    290                 295                 300

Pro Ala Ala
305

<210> SEQ ID NO 7
<211> LENGTH: 310
<212> TYPE: PRT
<213> ORGANISM: Artificial Sequence
<220> FEATURE:
<223> OTHER INFORMATION: synthesized, a fusion protein comprising: a
      fragment of TRAIL protein, fragment of human interferon gamma,
      flexible glycine-serine linkers and fragments recognized by
      urokinase and metalloprotease MMP

<400> SEQUENCE: 7

Gln Asp Pro Tyr Val Lys Glu Ala Glu Asn Leu Lys Lys Tyr Phe Asn
 1               5                  10                  15

Ala Gly His Ser Asp Val Ala Asp Asn Gly Thr Leu Phe Leu Gly Ile
             20                  25                  30

Leu Lys Asn Trp Lys Glu Glu Ser Asp Arg Lys Ile Met Gln Ser Gln
         35                  40                  45
```

```
Ile Val Ser Phe Tyr Phe Lys Leu Phe Lys Asn Phe Lys Asp Asp Gln
        50                  55                  60

Ser Ile Gln Lys Ser Val Glu Thr Ile Lys Glu Asp Met Asn Val Lys
 65                  70                  75                  80

Phe Phe Asn Ser Asn Lys Lys Arg Asp Asp Phe Glu Lys Leu Thr
                 85                  90                  95

Asn Tyr Ser Val Thr Asp Leu Asn Val Gln Arg Lys Ala Ile His Glu
                100                 105                 110

Leu Ile Gln Val Met Ala Glu Leu Ser Pro Ala Ala Gly Ser Gly Gly
            115                 120                 125

Gly Pro Leu Gly Leu Ala Gly Arg Val Val Arg Gly Ser Gly Gly Gly
        130                 135                 140

Glu Arg Gly Pro Gln Arg Val Ala Ala His Ile Thr Gly Thr Arg Gly
145                 150                 155                 160

Arg Ser Asn Thr Leu Ser Ser Pro Asn Ser Lys Asn Glu Lys Ala Leu
                165                 170                 175

Gly Arg Lys Ile Asn Ser Trp Glu Ser Ser Arg Ser Gly His Ser Phe
            180                 185                 190

Leu Ser Asn Leu His Leu Arg Asn Gly Glu Leu Val Ile His Glu Lys
        195                 200                 205

Gly Phe Tyr Tyr Ile Tyr Ser Gln Thr Tyr Phe Arg Phe Gln Glu Glu
        210                 215                 220

Ile Lys Glu Asn Thr Lys Asn Asp Lys Gln Met Val Gln Tyr Ile Tyr
225                 230                 235                 240

Lys Tyr Thr Ser Tyr Pro Asp Pro Ile Leu Leu Met Lys Ser Ala Arg
                245                 250                 255

Asn Ser Cys Trp Ser Lys Asp Ala Glu Tyr Gly Leu Tyr Ser Ile Tyr
            260                 265                 270

Gln Gly Gly Ile Phe Glu Leu Lys Glu Asn Asp Arg Ile Phe Val Ser
        275                 280                 285

Val Thr Asn Glu His Leu Ile Asp Met Asp His Glu Ala Ser Phe Phe
        290                 295                 300

Gly Ala Phe Leu Val Gly
305                 310

<210> SEQ ID NO 8
<211> LENGTH: 310
<212> TYPE: PRT
<213> ORGANISM: Artificial Sequence
<220> FEATURE:
<223> OTHER INFORMATION: synthesized, a fusion protein comprising: a
      fragment of TRAIL protein, fragment of human interferon gamma,
      flexible glycine-serine linkers and fragments recognized by
      urokinase and metalloprotease MMP

<400> SEQUENCE: 8

Glu Arg Gly Pro Gln Arg Val Ala Ala His Ile Thr Gly Thr Arg Gly
 1                   5                  10                  15

Arg Ser Asn Thr Leu Ser Ser Pro Asn Ser Lys Asn Glu Lys Ala Leu
                 20                  25                  30

Gly Arg Lys Ile Asn Ser Trp Glu Ser Ser Arg Ser Gly His Ser Phe
            35                  40                  45

Leu Ser Asn Leu His Leu Arg Asn Gly Glu Leu Val Ile His Glu Lys
        50                  55                  60

Gly Phe Tyr Tyr Ile Tyr Ser Gln Thr Tyr Phe Arg Phe Gln Glu Glu
 65                  70                  75                  80
```

Ile Lys Glu Asn Thr Lys Asn Asp Lys Gln Met Val Gln Tyr Ile Tyr
                85                  90                  95

Lys Tyr Thr Ser Tyr Pro Asp Pro Ile Leu Leu Met Lys Ser Ala Arg
            100                 105                 110

Asn Ser Cys Trp Ser Lys Asp Ala Glu Tyr Gly Leu Tyr Ser Ile Tyr
            115                 120                 125

Gln Gly Gly Ile Phe Glu Leu Lys Glu Asn Asp Arg Ile Phe Val Ser
130                 135                 140

Val Thr Asn Glu His Leu Ile Asp Met Asp His Glu Ala Ser Phe Phe
145                 150                 155                 160

Gly Ala Phe Leu Val Gly Gly Ser Gly Gly Gly Pro Leu Gly Leu Ala
                165                 170                 175

Gly Arg Val Val Arg Gly Ser Gly Gly Gly Gln Asp Pro Tyr Val Lys
                180                 185                 190

Glu Ala Glu Asn Leu Lys Lys Tyr Phe Asn Ala Gly His Ser Asp Val
            195                 200                 205

Ala Asp Asn Gly Thr Leu Phe Leu Gly Ile Leu Lys Asn Trp Lys Glu
            210                 215                 220

Glu Ser Asp Arg Lys Ile Met Gln Ser Gln Ile Val Ser Phe Tyr Phe
225                 230                 235                 240

Lys Leu Phe Lys Asn Phe Lys Asp Asp Gln Ser Ile Gln Lys Ser Val
                245                 250                 255

Glu Thr Ile Lys Glu Asp Met Asn Val Lys Phe Phe Asn Ser Asn Lys
            260                 265                 270

Lys Lys Arg Asp Asp Phe Glu Lys Leu Thr Asn Tyr Ser Val Thr Asp
            275                 280                 285

Leu Asn Val Gln Arg Lys Ala Ile His Glu Leu Ile Gln Val Met Ala
            290                 295                 300

Glu Leu Ser Pro Ala Ala
305                 310

<210> SEQ ID NO 9
<211> LENGTH: 317
<212> TYPE: PRT
<213> ORGANISM: Artificial Sequence
<220> FEATURE:
<223> OTHER INFORMATION: synthesized, a fusion protein comprising: a
      fragment of TRAIL protein, fragment of human interferon gamma,
      flexible glycine-serine linkers, a linker for pegylation and
      fragments recognized by urokinase and metalloprotease MMP

<400> SEQUENCE: 9

Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
65                  70                  75                  80

Phe Phe Asn Ser Asn Lys Lys Arg Asp Asp Phe Glu Lys Leu Thr
                85                  90                  95

Asn Tyr Ser Val Thr Asp Leu Asn Val Gln Arg Lys Ala Ile His Glu
            100                 105                 110

```
Leu Ile Gln Val Met Ala Glu Leu Ser Pro Ala Ala Gly Ser Gly Gly
            115                 120                 125

Gly Pro Leu Gly Leu Ala Gly Ala Ser Gly Cys Gly Pro Glu Arg Val
        130                 135                 140

Val Arg Gly Ser Gly Gly Gly Glu Arg Gly Pro Gln Arg Val Ala Ala
145                 150                 155                 160

His Ile Thr Gly Thr Arg Gly Arg Ser Asn Thr Leu Ser Ser Pro Asn
                165                 170                 175

Ser Lys Asn Glu Lys Ala Leu Gly Arg Lys Ile Asn Ser Trp Glu Ser
            180                 185                 190

Ser Arg Ser Gly His Ser Phe Leu Ser Asn Leu His Leu Arg Asn Gly
        195                 200                 205

Glu Leu Val Ile His Glu Lys Gly Phe Tyr Tyr Ile Tyr Ser Gln Thr
    210                 215                 220

Tyr Phe Arg Phe Gln Glu Glu Ile Lys Glu Asn Thr Lys Asn Asp Lys
225                 230                 235                 240

Gln Met Val Gln Tyr Ile Tyr Lys Tyr Thr Ser Tyr Pro Asp Pro Ile
                245                 250                 255

Leu Leu Met Lys Ser Ala Arg Asn Ser Cys Trp Ser Lys Asp Ala Glu
            260                 265                 270

Tyr Gly Leu Tyr Ser Ile Tyr Gln Gly Gly Ile Phe Glu Leu Lys Glu
        275                 280                 285

Asn Asp Arg Ile Phe Val Ser Val Thr Asn Glu His Leu Ile Asp Met
    290                 295                 300

Asp His Glu Ala Ser Phe Phe Gly Ala Phe Leu Val Gly
305                 310                 315

<210> SEQ ID NO 10
<211> LENGTH: 338
<212> TYPE: PRT
<213> ORGANISM: Artificial Sequence
<220> FEATURE:
<223> OTHER INFORMATION: synthesized, a fusion protein comprising: a
      fragment of TRAIL protein, fragment of human interferon gamma,
      flexible glycine-serine linkers, a linker for pegylation and
      fragments recognized by urokinase and metalloprotease MMP

<400> SEQUENCE: 10

Gln Asp Pro Tyr Val Lys Glu Ala Glu Asn Leu Lys Lys Tyr Phe Asn
1               5                   10                  15

Ala

```
Pro Glu Gly Ser Gly Gly Gly Thr Ser Glu Thr Ile Ser Thr Val
145                 150                 155                 160

Gln Glu Lys Gln Gln Asn Ile Ser Pro Leu Val Arg Glu Arg Gly Pro
                165                 170                 175

Gln Arg Val Ala Ala His Ile Thr Gly Thr Arg Gly Arg Ser Asn Thr
            180                 185                 190

Leu Ser Ser Pro Asn Ser Lys Asn Glu Lys Ala Leu Gly Arg Lys Ile
        195                 200                 205

Asn Ser Trp Glu Ser Ser Arg Ser Gly His Ser Phe Leu Ser Asn Leu
    210                 215                 220

His Leu Arg Asn Gly Glu Leu Val Ile His Glu Lys Gly Phe Tyr Tyr
225                 230                 235                 240

Ile Tyr Ser Gln Thr Tyr Phe Arg Phe Gln Glu Glu Ile Lys Glu Asn
                245                 250                 255

Thr Lys Asn Asp Lys Gln Met Val Gln Tyr Ile Tyr Lys Tyr Thr Ser
                260                 265                 270

Tyr Pro Asp Pro Ile Leu Leu Met Lys Ser Ala Arg Asn Ser Cys Trp
            275                 280                 285

Ser Lys Asp Ala Glu Tyr Gly Leu Tyr Ser Ile Tyr Gln Gly Gly Ile
        290                 295                 300

Phe Glu Leu Lys Glu Asn Asp Arg Ile Phe Val Ser Val Thr Asn Glu
305                 310                 315                 320

His Leu Ile Asp Met Asp His Glu Ala Ser Phe Phe Gly Ala Phe Leu
                325                 330                 335

Val Gly

<210> SEQ ID NO 11
<211> LENGTH: 317
<212> TYPE: PRT
<213> ORGANISM: Artificial Sequence
<220> FEATURE:
<223> OTHER INFORMATION: synthesized, a fusion protein comprising: a
      fragment of TRAIL protein, fragment of human interferon gamma,
      flexible glycine-serine linkers, a linker for pegylation and
      fragments recognized by urokinase and metalloprotease MMP

<400> SEQUENCE: 11

Glu Arg Gly Pro Gln Arg Val Ala Ala His Ile Thr Gly Thr Arg Gly
1               5                   10                  15

Arg Ser Asn Thr Leu Ser Ser Pro Asn Ser Lys Asn Glu Lys Ala Leu
                20                  25                  30

Gly Arg Lys Ile Asn Ser Trp Glu Ser Ser Arg Ser Gly His Ser Phe
            35                  40                  45

Leu Ser Asn Leu His Leu Arg Asn Gly Glu Leu Val Ile His Glu Lys
        50                  55                  60

Gly Phe Tyr Tyr Ile Tyr Ser Gln Thr Tyr Phe Arg Phe Gln Glu Glu
65                  70                  75                  80

Ile Lys Glu Asn Thr Lys Asn Asp Lys Gln Met Val Gln Tyr Ile Tyr
                85                  90                  95

Lys Tyr Thr Ser Tyr Pro Asp Pro Ile Leu Leu Met Lys Ser Ala Arg
            100                 105                 110

Asn Ser Cys Trp Ser Lys Asp Ala Glu Tyr Gly Leu Tyr Ser Ile Tyr
        115                 120                 125

Gln Gly Gly Ile Phe Glu Leu Lys Glu Asn Asp Arg Ile Phe Val Ser
    130                 135                 140

Val Thr Asn Glu His Leu Ile Asp Met Asp His Glu Ala Ser Phe Phe
```

-continued

```
            145                 150                 155                 160
        Gly Ala Phe Leu Val Gly Gly Ser Gly Gly Gly Ala Ser Gly Cys Gly
                        165                 170                 175

Pro Glu Pro Leu Gly Leu Ala Gly Arg Val Val Arg Gly Ser Gly Gly
                        180                 185                 190

Gly Gln Asp Pro Tyr Val Lys Glu Ala Glu Asn Leu Lys Lys Tyr Phe
                        195                 200                 205

Asn Ala Gly His Ser Asp Val Ala Asp Asn Gly Thr Leu Phe Leu Gly
                210                 215                 220

Ile Leu Lys Asn Trp Lys Glu Glu Ser Asp Arg Lys Ile Met Gln Ser
        225                 230                 235                 240

Gln Ile Val Ser Phe Tyr Phe Lys Leu Phe Lys Asn Phe Lys Asp Asp
                        245                 250                 255

Gln Ser Ile Gln Lys Ser Val Glu Thr Ile Lys Glu Asp Met Asn Val
                        260                 265                 270

Lys Phe Phe Asn Ser Asn Lys Lys Arg Asp Asp Phe Glu Lys Leu
                        275                 280                 285

Thr Asn Tyr Ser Val Thr Asp Leu Asn Val Gln Arg Lys Ala Ile His
                290                 295                 300

Glu Leu Ile Gln Val Met Ala Glu Leu Ser Pro Ala Ala
        305                 310                 315

<210> SEQ ID NO 12
<211> LENGTH: 449
<212> TYPE: PRT
<213> ORGANISM: Artificial Sequence
<220> FEATURE:
<223> OTHER INFORMATION: synthesized, a fusion protein comprising: a
      fragment of TRAIL protein, fragment of human interferon gamma,
      flexible glycine-serine linkers and fragments recognized by
      urokinase and metalloprotease MMP.

<400> SEQUENCE: 12

Gln Asp Pro Tyr Val Lys Glu Ala Glu Asn Leu Lys Lys Tyr Phe Asn
        1               5                   10                  15

Ala Gly His Ser Asp Val Ala Asp Asn Gly Thr Leu Phe Leu Gly Ile
                        20                  25                  30

Leu Lys Asn Trp Lys Glu Glu Ser Asp Arg Lys Ile Met Gln Ser Gln
                        35                  40                  45

Ile Val Ser Phe Tyr Phe Lys Leu Phe Lys Asn Phe Lys Asp Asp Gln
                        50                  55                  60

Ser Ile Gln Lys Ser Val Glu Thr Ile Lys Glu Asp Met Asn Val Lys
        65                  70                  75                  80

Phe Phe Asn Ser Asn Lys Lys Arg Asp Asp Phe Glu Lys Leu Thr
                        85                  90                  95

Asn Tyr Ser Val Thr Asp Leu Asn Val Gln Arg Lys Ala Ile Asp Glu
                        100                 105                 110

Leu Ile Gln Val Met Ala Glu Phe Ser Thr Glu Gln Gln Glu Gly
                        115                 120                 125

Pro Tyr Val Lys Glu Ala Glu Asn Leu Lys Lys Tyr Phe Asn Ala Gly
                        130                 135                 140

His Ser Asp Val Ala Asp Asn Gly Thr Leu Phe Leu Gly Ile Leu Lys
        145                 150                 155                 160

Asn Trp Lys Glu Glu Ser Asp Arg Lys Ile Met Gln Ser Gln Ile Val
                        165                 170                 175

Ser Phe Tyr Phe Lys Leu Phe Lys Asn Phe Lys Asp Asp Gln Ser Ile
```

```
                    180                 185                 190
Gln Lys Ser Val Glu Thr Ile Lys Glu Asp Met Asn Val Lys Phe Phe
                195                 200                 205

Asn Ser Asn Lys Lys Lys Arg Asp Asp Phe Glu Lys Leu Thr Asn Tyr
            210                 215                 220

Ser Val Thr Asp Leu Asn Val Gln Arg Lys Ala Ile His Glu Leu Ile
225                 230                 235                 240

Gln Val Met Ala Glu Leu Ser Pro Ala Ala Lys Thr Gly Lys Arg Lys
                245                 250                 255

Arg Ser Gln Met Leu Phe Arg Gly Ser Gly Gly Pro Leu Gly Leu
            260                 265                 270

Ala Gly Arg Val Val Arg Gly Ser Gly Gly Glu Arg Gly Pro Gln
            275                 280                 285

Arg Val Ala Ala His Ile Thr Gly Thr Arg Gly Arg Ser Asn Thr Leu
            290                 295                 300

Ser Ser Pro Asn Ser Lys Asn Glu Lys Ala Leu Gly Arg Lys Ile Asn
305                 310                 315                 320

Ser Trp Glu Ser Ser Arg Ser Gly His Ser Phe Leu Ser Asn Leu His
                325                 330                 335

Leu Arg Asn Gly Glu Leu Val Ile His Glu Lys Gly Phe Tyr Tyr Ile
            340                 345                 350

Tyr Ser Gln Thr Tyr Phe Arg Phe Gln Glu Glu Ile Lys Glu Asn Thr
            355                 360                 365

Lys Asn Asp Lys Gln Met Val Gln Tyr Ile Tyr Lys Tyr Thr Ser Tyr
            370                 375                 380

Pro Asp Pro Ile Leu Leu Met Lys Ser Ala Arg Asn Ser Cys Trp Ser
385                 390                 395                 400

Lys Asp Ala Glu Tyr Gly Leu Tyr Ser Ile Tyr Gln Gly Gly Ile Phe
                405                 410                 415

Glu Leu Lys Glu Asn Asp Arg Ile Phe Val Ser Val Thr Asn Glu His
            420                 425                 430

Leu Ile Asp Met Asp His Glu Ala Ser Phe Phe Gly Ala Phe Leu Val
            435                 440                 445

Gly

<210> SEQ ID NO 13
<211> LENGTH: 449
<212> TYPE: PRT
<213> ORGANISM: Artificial Sequence
<220> FEATURE:
<223> OTHER INFORMATION: synthesized, a fusion protein comprising: a
      fragment of TRAIL protein, fragment of human interferon gamma,
      flexible glycine-serine linkers and fragments recognized by
      urokinase and metalloprotease MMP.

<400> SEQUENCE: 13

Glu Arg Gly Pro Gln Arg Val Ala Ala His Ile Thr Gly Thr Arg Gly
1               5                   10                  15

Arg Ser Asn Thr Leu Ser Ser Pro Asn Ser Lys Asn Glu Lys Ala Leu
            20                  25                  30

Gly Arg Lys Ile Asn Ser Trp Glu Ser Ser Arg Ser Gly His Ser Phe
        35                  40                  45

Leu Ser Asn Leu His Leu Arg Asn Gly Glu Leu Val Ile His Glu Lys
    50                  55                  60

Gly Phe Tyr Tyr Ile Tyr Ser Gln Thr Tyr Phe Arg Phe Gln Glu Glu
65                  70                  75                  80
```

```
Ile Lys Glu Asn Thr Lys Asn Asp Lys Gln Met Val Gln Tyr Ile Tyr
                85                  90                  95

Lys Tyr Thr Ser Tyr Pro Asp Pro Ile Leu Leu Met Lys Ser Ala Arg
            100                 105                 110

Asn Ser Cys Trp Ser Lys Asp Ala Glu Tyr Gly Leu Tyr Ser Ile Tyr
            115                 120                 125

Gln Gly Gly Ile Phe Glu Leu Lys Glu Asn Asp Arg Ile Phe Val Ser
    130                 135                 140

Val Thr Asn Glu His Leu Ile Asp Met Asp His Glu Ala Ser Phe Phe
145                 150                 155                 160

Gly Ala Phe Leu Val Gly Gly Ser Gly Gly Pro Leu Gly Leu Ala
                165                 170                 175

Gly Arg Val Val Arg Gly Ser Gly Gly Gln Asp Pro Tyr Val Lys
                180                 185                 190

Glu Ala Glu Asn Leu Lys Lys Tyr Phe Asn Ala Gly His Ser Asp Val
    195                 200                 205

Ala Asp Asn Gly Thr Leu Phe Leu Gly Ile Leu Lys Asn Trp Lys Glu
210                 215                 220

Glu Ser Asp Arg Lys Ile Met Gln Ser Gln Ile Val Ser Phe Tyr Phe
225                 230                 235                 240

Lys Leu Phe Lys Asn Phe Lys Asp Asp Gln Ser Ile Gln Lys Ser Val
                245                 250                 255

Glu Thr Ile Lys Glu Asp Met Asn Val Lys Phe Phe Asn Ser Asn Lys
            260                 265                 270

Lys Lys Arg Asp Asp Phe Glu Lys Leu Thr Asn Tyr Ser Val Thr Asp
                275                 280                 285

Leu Asn Val Gln Arg Lys Ala Ile Asp Glu Leu Ile Gln Val Met Ala
290                 295                 300

Glu Phe Ser Thr Glu Glu Gln Gly Pro Tyr Val Lys Glu Ala
305                 310                 315                 320

Glu Asn Leu Lys Lys Tyr Phe Asn Ala Gly His Ser Asp Val Ala Asp
                325                 330                 335

Asn Gly Thr Leu Phe Leu Gly Ile Leu Lys Asn Trp Lys Glu Glu Ser
            340                 345                 350

Asp Arg Lys Ile Met Gln Ser Gln Ile Val Ser Phe Tyr Phe Lys Leu
            355                 360                 365

Phe Lys Asn Phe Lys Asp Asp Gln Ser Ile Gln Lys Ser Val Glu Thr
    370                 375                 380

Ile Lys Glu Asp Met Asn Val Lys Phe Phe Asn Ser Asn Lys Lys Lys
385                 390                 395                 400

Arg Asp Asp Phe Glu Lys Leu Thr Asn Tyr Ser Val Thr Asp Leu Asn
                405                 410                 415

Val Gln Arg Lys Ala Ile His Glu Leu Ile Gln Val Met Ala Glu Leu
            420                 425                 430

Ser Pro Ala Ala Lys Thr Gly Lys Arg Lys Arg Ser Gln Met Leu Phe
            435                 440                 445

Arg

<210> SEQ ID NO 14
<211> LENGTH: 456
<212> TYPE: PRT
<213> ORGANISM: Artificial Sequence
<220> FEATURE:
<223> OTHER INFORMATION: synthesized, a fusion protein comprising: a
``` fragment of TRAIL protein, fragment of human interferon gamma,
flexible glycine-serine linkers, linker for pegylation and
fragments recognized by urokinase and metalloprotease MMP.

<400> SEQUENCE: 14

```
Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
65                  70                  75                  80

Phe Phe Asn Ser Asn Lys Lys Lys Arg Asp Asp Phe Glu Lys Leu Thr
                85                  90                  95

Asn Tyr Ser Val Thr Asp Leu Asn Val Gln Arg Lys Ala Ile Asp Glu
            100                 105                 110

Leu Ile Gln Val Met Ala Glu Phe Ser Thr Glu Glu Gln Gln Glu Gly
        115                 120                 125

Pro Tyr Val Lys Glu Ala Glu Asn Leu Lys Lys Tyr Phe Asn Ala Gly
    130                 135                 140

His Ser Asp Val Ala Asp Asn Gly Thr Leu Phe Leu Gly Ile Leu Lys
145                 150                 155                 160

Asn Trp Lys Glu Glu Ser Asp Arg Lys Ile Met Gln Ser Gln Ile Val
                165                 170                 175

Ser Phe Tyr Phe Lys Leu Phe Lys Asn Phe Lys Asp Asp Gln Ser Ile
            180                 185                 190

Gln Lys Ser Val Glu Thr Ile Lys Glu Asp Met Asn Val Lys Phe Phe
        195                 200                 205

Asn Ser Asn Lys Lys Lys Arg Asp Asp Phe Glu Lys Leu Thr Asn Tyr
    210                 215                 220

Ser Val Thr Asp Leu Asn Val Gln Arg Lys Ala Ile His Glu Leu Ile
225                 230                 235                 240

Gln Val Met Ala Glu Leu Ser Pro Ala Ala Lys Thr Gly Lys Arg Lys
                245                 250                 255

Arg Ser Gln Met Leu Phe Arg Gly Ser Gly Gly Gly Pro Leu Gly Leu
            260                 265                 270

Ala Gly Ala Ser Gly Cys Gly Pro Glu Arg Val Val Arg Gly Ser Gly
        275                 280                 285

Gly Gly Glu Arg Gly Pro Gln Arg Val Ala Ala His Ile Thr Gly Thr
    290                 295                 300

Arg Gly Arg Ser Asn Thr Leu Ser Ser Pro Asn Ser Lys Asn Glu Lys
305                 310                 315                 320

Ala Leu Gly Arg Lys Ile Asn Ser Trp Glu Ser Ser Arg Ser Gly His
                325                 330                 335

Ser Phe Leu Ser Asn Leu His Leu Arg Asn Gly Glu Leu Val Ile His
            340                 345                 350

Glu Lys Gly Phe Tyr Tyr Ile Tyr Ser Gln Thr Tyr Phe Arg Phe Gln
        355                 360                 365

Glu Glu Ile Lys Glu Asn Thr Lys Asn Asp Lys Gln Met Val Gln Tyr
    370                 375                 380

Ile Tyr Lys Tyr Thr Ser Tyr Pro Asp Pro Ile Leu Leu Met Lys Ser
```

```
                385                 390                 395                 400
Ala Arg Asn Ser Cys Trp Ser Lys Asp Ala Glu Tyr Gly Leu Tyr Ser
                405                 410                 415

Ile Tyr Gln Gly Gly Ile Phe Glu Leu Lys Glu Asn Asp Arg Ile Phe
                420                 425                 430

Val Ser Val Thr Asn Glu His Leu Ile Asp Met Asp His Glu Ala Ser
                435                 440                 445

Phe Phe Gly Ala Phe Leu Val Gly
                450                 455

<210> SEQ ID NO 15
<211> LENGTH: 456
<212> TYPE: PRT
<213> ORGANISM: Artificial Sequence
<220> FEATURE:
<223> OTHER INFORMATION: synthesized, a fusion protein comprising: a
      fragment of TRAIL protein, fragment of human interferon gamma,
      flexible glycine-serine linkers, linker for pegylation and
      fragments recognized by urokinase and metalloprotease MMP.

<400> SEQUENCE: 15

Glu Arg Gly Pro Gln Arg Val Ala Ala His Ile Thr Gly Thr Arg Gly
1               5                   10                  15

Arg Ser Asn Thr Leu Ser Ser Pro Asn Ser Lys Asn Glu Lys Ala Leu
                20                  25                  30

Gly Arg Lys Ile Asn Ser Trp Glu Ser Ser Arg Ser Gly His Ser Phe
            35                  40                  45

Leu Ser Asn Leu His Leu Arg Asn Gly Glu Leu Val Ile His Glu Lys
        50                  55                  60

Gly Phe Tyr Tyr Ile Tyr Ser Gln Thr Tyr Phe Arg Phe Gln Glu Glu
65              70                  75                  80

Ile Lys Glu Asn Thr Lys Asn Asp Lys Gln Met Val Gln Tyr Ile Tyr
                85                  90                  95

Lys Tyr Thr Ser Tyr Pro Asp Pro Ile Leu Leu Met Lys Ser Ala Arg
                100                 105                 110

Asn Ser Cys Trp Ser Lys Asp Ala Glu Tyr Gly Leu Tyr Ser Ile Tyr
            115                 120                 125

Gln Gly Gly Ile Phe Glu Leu Lys Glu Asn Asp Arg Ile Phe Val Ser
        130                 135                 140

Val Thr Asn Glu His Leu Ile Asp Met Asp His Glu Ala Ser Phe Phe
145             150                 155                 160

Gly Ala Phe Leu Val Gly Gly Ser Gly Gly Pro Leu Gly Leu Ala
                165                 170                 175

Gly Ala Ser Gly Cys Gly Pro Glu Arg Val Val Arg Gly Ser Gly Gly
            180                 185                 190

Gly Gln Asp Pro Tyr Val Lys Glu Ala Glu Asn Leu Lys Lys Tyr Phe
        195                 200                 205

Asn Ala Gly His Ser Asp Val Ala Asp Asn Gly Thr Leu Phe Leu Gly
        210                 215                 220

Ile Leu Lys Asn Trp Lys Glu Glu Ser Asp Arg Lys Ile Met Gln Ser
225             230                 235                 240

Gln Ile Val Ser Phe Tyr Phe Lys Leu Phe Lys Asn Phe Lys Asp Asp
                245                 250                 255

Gln Ser Ile Gln Lys Ser Val Glu Thr Ile Lys Glu Asp Met Asn Val
                260                 265                 270

Lys Phe Phe Asn Ser Asn Lys Lys Lys Arg Asp Asp Phe Glu Lys Leu
```

```
                275                 280                 285
Thr Asn Tyr Ser Val Thr Asp Leu Asn Val Gln Arg Lys Ala Ile Asp
    290                 295                 300
Glu Leu Ile Gln Val Met Ala Glu Phe Ser Thr Glu Gln Gln Glu
305                 310                 315                 320
Gly Pro Tyr Val Lys Glu Ala Glu Asn Leu Lys Lys Tyr Phe Asn Ala
                325                 330                 335
Gly His Ser Asp Val Ala Asp Asn Gly Thr Leu Phe Leu Gly Ile Leu
            340                 345                 350
Lys Asn Trp Lys Glu Glu Ser Asp Arg Lys Ile Met Gln Ser Gln Ile
        355                 360                 365
Val Ser Phe Tyr Phe Lys Leu Phe Lys Asn Phe Lys Asp Asp Gln Ser
    370                 375                 380
Ile Gln Lys Ser Val Glu Thr Ile Lys Glu Asp Met Asn Val Lys Phe
385                 390                 395                 400
Phe Asn Ser Asn Lys Lys Lys Arg Asp Asp Phe Glu Lys Leu Thr Asn
                405                 410                 415
Tyr Ser Val Thr Asp Leu Asn Val Gln Arg Lys Ala Ile His Glu Leu
            420                 425                 430
Ile Gln Val Met Ala Glu Leu Ser Pro Ala Ala Lys Thr Gly Lys Arg
        435                 440                 445
Lys Arg Ser Gln Met Leu Phe Arg
    450                 455

<210> SEQ ID NO 16
<211> LENGTH: 281
<212> TYPE: PRT
<213> ORGANISM: Homo sapiens
<300> PUBLICATION INFORMATION:
<308> DATABASE ACCESSION NUMBER: GenBank/P50591
<309> DATABASE ENTRY DATE: 1996-10-01
<313> RELEVANT RESIDUES IN SEQ ID NO: (1)..(281)

<400> SEQUENCE: 16

Met Ala Met Met Glu Val Gln Gly Gly Pro Ser Leu Gly Gln Thr Cys
1               5                   10                  15
Val Leu Ile Val Ile Phe Thr Val Leu Leu Gln Ser Leu Cys Val Ala
            20                  25                  30
Val Thr Tyr Val Tyr Phe Thr Asn Glu Leu Lys Gln Met Gln Asp Lys
        35                  40                  45
Tyr Ser Lys Ser Gly Ile Ala Cys Phe Leu Lys Glu Asp Asp Ser Tyr
    50                  55                  60
Trp Asp Pro Asn Asp Glu Glu Ser Met Asn Ser Pro Cys Trp Gln Val
65              70                  75                  80
Lys Trp Gln Leu Arg Gln Leu Val Arg Lys Met Ile Leu Arg Thr Ser
                85                  90                  95
Glu Glu Thr Ile Ser Thr Val Gln Glu Lys Gln Gln Asn Ile Ser Pro
            100                 105                 110
Leu Val Arg Glu Arg Gly Pro Gln Arg Val Ala Ala His Ile Thr Gly
        115                 120                 125
Thr Arg Gly Arg Ser Asn Thr Leu Ser Ser Pro Asn Ser Lys Asn Glu
    130                 135                 140
Lys Ala Leu Gly Arg Lys Ile Asn Ser Trp Glu Ser Ser Arg Ser Gly
145             150                 155                 160
His Ser Phe Leu Ser Asn Leu His Leu Arg Asn Gly Glu Leu Val Ile
                165                 170                 175
```

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
            195                 200                 205

Tyr Ile Tyr Lys Tyr Thr Ser Tyr Pro Asp Pro Ile Leu Leu Met Lys
            210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
            245                 250                 255

Phe Val Ser Val Thr Asn Glu His Leu Ile Asp Met Asp His Glu Ala
            260                 265                 270

Ser Phe Phe Gly Ala Phe Leu Val Gly
            275                 280

<210> SEQ ID NO 17
<211> LENGTH: 150
<212> TYPE: PRT
<213> ORGANISM: Homo sapiens
<300> PUBLICATION INFORMATION:
<308> DATABASE ACCESSION NUMBER: GenBank: AAB59402.1
<309> DATABASE ENTRY DATE: 2001-01-08
<313> RELEVANT RESIDUES IN SEQ ID NO: (24)..(173)
<300> PUBLICATION INFORMATION:
<308> DATABASE ACCESSION NUMBER: GenBank/ AAB59402.1
<309> DATABASE ENTRY DATE: 2001-01-08
<313> RELEVANT RESIDUES IN SEQ ID NO: (24)..(173)

<400> SEQUENCE: 17

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser
145                 150

<210> SEQ ID NO 18
<211> LENGTH: 124
<212> TYPE: PRT
<213> ORGANISM: Homo sapiens
<300> PUBLICATION INFORMATION:
<308> DATABASE ACCESSION NUMBER: GenBank: AAM28885.1
<309> DATABASE ENTRY DATE: 2002-05-16
<313> RELEVANT RESIDUES IN SEQ ID NO: (2)..(125)
<300> PUBLICATION INFORMATION:
<308> DATABASE ACCESSION NUMBER: GenBank/AAM28885.1

```
<309> DATABASE ENTRY DATE: 2002-05-16
<313> RELEVANT RESIDUES IN SEQ ID NO: (2)..(125)

<400> SEQUENCE: 18
```

Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
65                  70                  75                  80

Phe Phe Asn Ser Asn Lys Lys Arg Asp Asp Phe Glu Lys Leu Thr
                85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala
        115                 120

```
<210> SEQ ID NO 19
<211> LENGTH: 263
<212> TYPE: PRT
<213> ORGANISM: Homo sapiens
<300> PUBLICATION INFORMATION:
<308> DATABASE ACCESSION NUMBER: PDB/1EKUA
<309> DATABASE ENTRY DATE: 2008-09-24
<313> RELEVANT RESIDUES IN SEQ ID NO: (2)..(264)

<400> SEQUENCE: 19
```

Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
65                  70                  75                  80

Phe Phe Asn Ser Asn Lys Lys Arg Asp Asp Phe Glu Lys Leu Thr
                85                  90                  95

Asn Tyr Ser Val Thr Asp Leu Asn Val Gln Arg Lys Ala Ile Asp Glu
            100                 105                 110

Leu Ile Gln Val Met Ala Glu Phe Ser Thr Glu Gln Gln Glu Gly
        115                 120                 125

Pro Tyr Val Lys Glu Ala Glu Asn Leu Lys Lys Tyr Phe Asn Ala Gly
        130                 135                 140

His Ser Asp Val Ala Asp Asn Gly Thr Leu Phe Leu Gly Ile Leu Lys
145                 150                 155                 160

Asn Trp Lys Glu Glu Ser Asp Arg Lys Ile Met Gln Ser Gln Ile Val
                165                 170                 175

Ser Phe Tyr Phe Lys Leu Phe Lys Asn Phe Lys Asp Asp Gln Ser Ile
            180                 185                 190

Gln Lys Ser Val Glu Thr Ile Lys Glu Asp Met Asn Val Lys Phe Phe
        195                 200                 205

```
Asn Ser Asn Lys Lys Arg Asp Asp Phe Glu Lys Leu Thr Asn Tyr
    210                 215                 220

Ser Val Thr Asp Leu Asn Val Gln Arg Lys Ala Ile His Glu Leu Ile
225                 230                 235                 240

Gln Val Met Ala Glu Leu Ser Pro Ala Ala Lys Thr Gly Lys Arg Lys
            245                 250                 255

Arg Ser Gln Met Leu Phe Arg
            260
```

```
<210> SEQ ID NO 20
<211> LENGTH: 6
<212> TYPE: PRT
<213> ORGANISM: Artificial Sequence
<220> FEATURE:
<223> OTHER INFORMATION: synthesized, a sequence recognized by
      metalloprotease MMP

<400> SEQUENCE: 20

Pro Leu Gly Leu Ala Gly
1               5

<210> SEQ ID NO 21
<211> LENGTH: 4
<212> TYPE: PRT
<213> ORGANISM: Artificial Sequence
<220> FEATURE:
<223> OTHER INFORMATION: synthesized, a sequence recognized by urokinase
      uPa

<400> SEQUENCE: 21

Arg Val Val Arg
1

<210> SEQ ID NO 22
<211> LENGTH: 7
<212> TYPE: PRT
<213> ORGANISM: Artificial Sequence
<220> FEATURE:
<223> OTHER INFORMATION: synthesized, a linker for pegylation
<300> PUBLICATION INFORMATION:
<301> AUTHORS: Tsutsumi Y, Onda M, Nagata S, Lee B, Kreitman RJ,
      Pastan I.
<302> TITLE: Site-specific chemical modification with polyethylene
      glycol of recombinant immunotoxin anti-Tac(Fv)-PE38 (LMB-2)
      improves antitumor activity and reduces animal toxicity and
      immunogenicity.
<303> JOURNAL: Proc Natl Acad Sci U S A.
<304> VOLUME: 97
<305> ISSUE: 15
<306> PAGES: 8548-53
<307> DATE: 2000-07-18
<308> DATABASE ACCESSION NUMBER: PMID/10890891
<309> DATABASE ENTRY DATE: 2000-07-18

<400> SEQUENCE: 22

Ala Ser Gly Cys Gly Pro Glu
1               5

<210> SEQ ID NO 23
<211> LENGTH: 5
<212> TYPE: PRT
<213> ORGANISM: Artificial Sequence
<220> FEATURE:
<223> OTHER INFORMATION: synthesized, a linker for pegylation

<400> SEQUENCE: 23

Ala Ala Cys Ala Ala
```

```
1               5

<210> SEQ ID NO 24
<211> LENGTH: 7
<212> TYPE: PRT
<213> ORGANISM: Artificial Sequence
<220> FEATURE:
<223> OTHER INFORMATION: synthesized, a linker for pegylation

<400> SEQUENCE: 24

Ser Gly Gly Cys Gly Gly Ser
1               5

<210> SEQ ID NO 25
<211> LENGTH: 5
<212> TYPE: PRT
<213> ORGANISM: Artificial Sequence
<220> FEATURE:
<223> OTHER INFORMATION: synthesized, a linker for pegylation

<400> SEQUENCE: 25

Ser Gly Cys Gly Ser
1               5

<210> SEQ ID NO 26
<211> LENGTH: 5
<212> TYPE: PRT
<213> ORGANISM: Artificial Sequence
<220> FEATURE:
<223> OTHER INFORMATION: synthesized, a steric linker

<400> SEQUENCE: 26

Gly Ser Gly Gly Gly
1               5

<210> SEQ ID NO 27
<211> LENGTH: 4
<212> TYPE: PRT
<213> ORGANISM: Artificial Sequence
<220> FEATURE:
<223> OTHER INFORMATION: synthesized, a steric linker

<400> SEQUENCE: 27

Gly Gly Gly Ser
1

<210> SEQ ID NO 28
<211> LENGTH: 4
<212> TYPE: PRT
<213> ORGANISM: Artificial Sequence
<220> FEATURE:
<223> OTHER INFORMATION: synthesized, a steric linker
<220> FEATURE:
<221> NAME/KEY: misc_feature
<222> LOCATION: (1)..(1)
<223> OTHER INFORMATION: Xaa can be any naturally occurring amino acid

<400> SEQUENCE: 28

Xaa Gly Gly Ser
1

<210> SEQ ID NO 29
<211> LENGTH: 1034
<212> TYPE: DNA
<213> ORGANISM: Artificial Sequence
<220> FEATURE:
<223> OTHER INFORMATION: synthesized, encoding a fusion protein
      comprising: a fragment of TRAIL protein, subunit 2b of human
``` interferon alpha, and fragments recognized by urokinase and
metalloprotease MMP

<400> SEQUENCE: 29

| | | | | |
|---|---|---|---|---|
| tgtgatctgc | cgcagaccca | tagcctgggt | agccgtcgta | ccctgatgct gctggcacag | 60 |
| atgcgtcgta | ttagcctgtt | tagctgcctg | aaagatcgtc | atgattttgg ttttccgcag | 120 |
| gaagaatttg | gtaatcagtt | tcagaaagcc | gaaaccattc | cggttctgca tgaaatgatt | 180 |
| cagcagattt | taacctgtt | tagcaccaaa | gatagcagcg | cagcatggga tgaaaccctg | 240 |
| ctggataaat | tttataccga | actgtatcag | cagctgaatg | atctggaagc atgtgttatt | 300 |
| cagggtgttg | gtgttaccga | acaccgctg | atgaaagaag | atagcattct ggccgtgcgt | 360 |
| aaatattttc | agcgcattac | cctgtatctg | aaagaaaaaa | aatatagccc gtgtgcatgg | 420 |
| gaagttgttc | gtgcagaaat | tatgcgtagc | tttagcctga | gcaccaatct gcaggaaagc | 480 |
| ctgcgtagca | aagaaccgct | gggtctggca | ggtcgtgttg | ttcgtccgct ggcctggctg | 540 |
| gccgtgtggt | gcgtgttgca | gcacatatta | ccggcacccg | tggtcgtagc aatacctga | 600 |
| gcagcccgaa | tagcaaaaat | gaaaagccc | tgggtcgcaa | aattaatagc tgggaaagca | 660 |
| gccgtagcgg | tcatagcttt | ctgagcaatc | tgcatctgcg | taatggtgaa ctggtgattc | 720 |
| atgaaaaagg | ctttttattat | atttatagcc | agacctattt | tcgctttcag gaagaaatta | 780 |
| aagaaaatac | caaaaatgat | aaacaaatgg | tgcagtatat | ctataaatat accagctatc | 840 |
| cggatccgat | tctgctgatg | aaaagcgcac | gtaatagctg | ttggagcaaa gatgcagaat | 900 |
| atggcctgta | tagcatttat | cagggtggca | tttttgaact | gaaagaaaat gatcgcatt | 960 |
| ttgtgagcgt | gaccaatgaa | catctgattg | atatggatca | tgaagccagc ttttttggtg | 1020 |
| catttctggt | gggt | | | | 1034 |

<210> SEQ ID NO 30
<211> LENGTH: 1040
<212> TYPE: DNA
<213> ORGANISM: Artificial Sequence
<220> FEATURE:
<223> OTHER INFORMATION: synthesized, encoding a fusion protein
      comprising: a fragment of TRAIL protein, subunit 2b of human
      interferon alpha, and fragments recognized by urokinase and
      metalloprotease MMP

<400> SEQUENCE: 30

| | | | | |
|---|---|---|---|---|
| ccgcagcgtg | ttgcagcaca | tattaccggc | acccgtggtc | gtagcaatac cctgagcagc | 60 |
| ccgaatagca | aaaatgaaaa | agccctgggt | cgcaaaatta | atagctggga aagcagccgt | 120 |
| agcggtcata | gctttctgag | caatctgcat | ctgcgtaatg | gtgaactggt gattcatgaa | 180 |
| aaaggctttt | attatattta | tagccagacc | tattttcgct | ttcaggaaga aattaaagaa | 240 |
| aataccaaaa | atgataaaca | aatggtgcag | tatatctata | aataccag ctatccggat | 300 |
| ccgattctgc | tgatgaaaag | cgcacgtaat | agctgttgga | gcaaagatgc agaatatggc | 360 |
| ctgtatagca | tttatcaggg | tggcattttt | gaactgaaag | aaaatgatcg cattttgtg | 420 |
| agcgtgacca | atgaacatct | gattgatatg | gatcatgaag | ccagctttt tggtgcattt | 480 |
| ctggtgggtc | cgctgggtct | ggcaggtcgt | gttgttcgtc | cgctgggcct gctggccgtg | 540 |
| tggtgtgtga | tctgccgcag | acccatagcc | tgggtagccg | tcgtaccctg atgctgctgg | 600 |
| cacagatgcg | tcgtattagc | ctgtttagct | gcctgaaaga | tcgtcatgat tttggttttc | 660 |
| cgcaggaaga | atttggtaat | cagtttcaga | aagccgaaac | cattccggtt ctgcatgaaa | 720 |
| tgattcagca | gattttaac | ctgtttagca | ccaaagatag | cagcgcagca tgggatgaaa | 780 |

```
ccctgctgga taaattttat accgaactgt atcagcagct gaatgatctg gaagcatgtg    840
ttattcaggg tgttggtgtt accgaaacac cgctgatgaa agaagatagc attctggccg    900
tgcgtaaata ttttcagcgc attaccctgt atctgaaaga aaaaaaatat agcccgtgtg    960
catgggaagt tgttcgtgca gaaattatgc gtagctttag cctgagcacc aatctgcagg   1020
aaagcctgcg tagcaaagaa                                                1040

<210> SEQ ID NO 31
<211> LENGTH: 1054
<212> TYPE: DNA
<213> ORGANISM: Artificial Sequence
<220> FEATURE:
<223> OTHER INFORMATION: synthesized, encoding a fusion protein
      comprising: a fragment of TRAIL protein, subunit 2b of human
      interferon alpha, linker for pegylation and fragments recognized
      by urokinase and metalloprotease MMP.

<400> SEQUENCE: 31
tgtgatctgc cgcagaccca tagcctgggt agccgtcgta ccctgatgct gctggcacag     60
atgcgtcgta ttagcctgtt tagctgcctg aaagatcgtc atgatttggt ttttccgcag    120
gaagaatttg gtaatcagtt tcagaaagcc gaaaccattc cggttctgca tgaaatgatt    180
cagcagattt ttaacctgtt tagcaccaaa gatagcagcg cagcatggga tgaaaccctg    240
ctggataaat tttataccga actgtatcag cagctgaatg atctggaagc atgtgttatt    300
cagggtgttg gtgttaccga aacaccgctg atgaagaag atagcattct ggccgtgcgt    360
aaatattttc agcgcattac cctgtatctg aagaaaaaa atatagcccc gtgtgcatgg    420
gaagttgttc gtgcagaaat tatgcgtagc tttagcctga gcaccaatct gcaggaaagc    480
ctgcgtagca agaaccgct gggtctggca ggtcgtgttg ttcgtgcgtc ggctgcggtc    540
cggaaccgct gggcctggct ggccgtgtgg tgcgtgttgc agcacatata ccggcacccg    600
tggtcgtagc aataccctga gcagcccgaa tagcaaaaat gaaaagccc tgggtcgcaa    660 aattaatagc tgggaaagca gccgtagcgg tcatagcttt ctgagcaatc tgcatctgcg    720
taatggtgaa ctggtgattc atgaaaaagg cttttattat atttataggc agacctattt    780
tcgctttcag gaagaaatta aggaaaatac caaaaatgat aacaaatgg tgcagtatat    840 ctataaatat accagctatc cggatccgat tctgctgatg aaaagcgcac gtaatagctg    900
ttggagcaaa gatgcagaat atggcctgta tagcatttat cagggtggca ttttttgaact    960 gaaagaaaat gatcgcattt ttgtgagcgt gaccaatgaa catctgattg atatggatca   1020
tgaagccagc ttttttggtg catttctggt gggt                                1054

<210> SEQ ID NO 32
<211> LENGTH: 1057
<212> TYPE: DNA
<213> ORGANISM: Artificial Sequence
<220> FEATURE:
<223> OTHER INFORMATION: synthesized, encoding a fusion protein
      comprising: a fragment of TRAIL protein, subunit 2b of human
      interferon alpha, linker for pegylation and fragments recognized
      by urokinase and metalloprotease MMP.

<400> SEQUENCE: 32
cagcgtgttg cagcacatat taccggcacc cgtggtcgta gcaataccct gagcagcccg     60
aatagcaaaa atgaaaaagc cctgggtcgc aaaattaata gctgggaaag cagccgtagc    120
ggtcatagct ttctgagcaa tctgcatctg cgtaatggtg aactggtgat tcatgaaaaa    180
```

-continued

| | |
|---|---|
| ggcttttatt atatttatag ccagaccctat tttcgctttc aggaagaaat taaagaaaat | 240 |
| accaaaaatg ataaacaaat ggtgcagtat atctataaat ataccagcta tccggatccg | 300 |
| attctgctga tgaaaagcgc acgtaatagc tgttggagca aagatgcaga atatggcctg | 360 |
| tatagcattt atcagggtgg cattttttgaa ctgaaagaaa atgatcgcat ttttgtgagc | 420 |
| gtgaccaatg aacatctgat tgatatggat catgaagcca gcttttttgg tgcatttctg | 480 |
| gtgggtccgc tgggtctggc aggtcgtgtt gttcgtgcgt ctggctgcgg ccggaaccgc | 540 |
| tgggcctggc tggccgtgtg gtgtgtgatc tgccgcagac ccatagcctg gtagccgtcg | 600 |
| taccctgatg ctgctggcac agatgcgtcg tattagcctg tttagctgcc tgaaagatcg | 660 |
| tcatgatttt ggttttccgc aggaagaatt tggtaatcag tttcagaaag ccgaaaccat | 720 |
| tccggttctg catgaaatga ttcagcagat tttttaacctg tttagcacca agatagcag | 780 |
| cgcagcatgg gatgaaaccc tgctggataa atttttatacc gaactgtatc agcagctgaa | 840 |
| tgatctggaa gcatgtgtta ttcagggtgt tggtgttacc gaaacaccgc tgatgaaaga | 900 |
| agatagcatt ctggccgtgc gtaaatattt tcagcgcatt accctgtatc tgaaagaaaa | 960 |
| aaaatatagc ccgtgtgcat gggaagttgt tcgtgcagaa attatgcgta gctttagcct | 1020 |
| gagcaccaat ctgcaggaaa gcctgcgtag caaagaa | 1057 |

<210> SEQ ID NO 33
<211> LENGTH: 899
<212> TYPE: DNA
<213> ORGANISM: Artificial Sequence
<220> FEATURE:
<223> OTHER INFORMATION: synthesized, encoding a fusion protein comprising: a fragment of TRAIL protein, fragment of human interferon gamma and fragments recognized by urokinase and metalloprotease MMP.

<400> SEQUENCE: 33
caggatccgt atgttaaaga agccgaaaat ctgaaaaaat attttaatgc cggtcattct 60
gatgttgcag ataatggcac cctgtttctg ggtattctga aaaattggaa agaagaaagc 120
gatcgcaaaa tcatgcagag ccagatcgtg agcttttatt tcaaactgtt caaaaatttt 180
aaagatgatc agagcattca gaaaagcgtg gaaaccatta aagaagacat gaacgtaaaa 240
ttcttcaatt ccaataaaaa aaaacgcgat gatttcgaaa aactgaccaa ttatagcgtg 300
accgatctga atgttcagcg taaagccatt catgaactga ttcaggttat ggcagaactg 360
tctccggcag caccgctggg tctggcaggc cgtgttgttc gtgaacgtgg ccgcagcgtg 420
ttgcagcaca tattaccggc acccgtggtc gtagcaatac cctgagcagc ccgaatagca 480
aaaatgaaaa agccctgggt cgcaaaatta atagctggga aagcagccgt agcggtcata 540
gctttctgag caatctgcat ctgcgtaatg gtgaactggt gattcatgaa aaaggctttt 600
attatattta tagccagacc tattttcgct ttcaggaaga aattaaagaa aacaccaaaa 660
atgataaaca aatggtgcag tatatctata aatataccag ctatccggat ccgattctgc 720
tgatgaaaag cgcacgtaat agctgttgga gcaaagatgc agaatatggc ctgtatagca 780
tttatcaggg tggcattttt gaactgaaag aaaatgatcg catttttgtg agcgtgacca 840
atgaacatct gattgatatg gatcatgaag ccagcttttt tggtgcattt ctggtgggt 899

<210> SEQ ID NO 34
<211> LENGTH: 857
<212> TYPE: DNA
<213> ORGANISM: Artificial Sequence
<220> FEATURE:

<223> OTHER INFORMATION: synthesized, encoding a fusion protein
comprising: a fragment of TRAIL protein, fragment of human
interferon gamma, flexible glycine-serine linkers and fragments
recognized by urokinase and metalloprotease MMP.

<400> SEQUENCE: 34

| | | | | | |
|---|---|---|---|---|---|
| cgtgaacgtg | gtccgcagcg | tgttgcagca | catattaccg | gcacccgtgg | tcgtagcaat | 60 |
| accctgagca | gcccgaatag | caaaaatgaa | aaagccctgg | gtcgcaaaat | aatagctgg | 120 |
| gaaagcagcc | gtagcggtca | tagcttctg | agcaatctgc | atctgcgtaa | tggtgaactg | 180 |
| gtgattcatg | aaaaaggctt | ttattatatt | tatagccaga | cctatttcg | ctttcaggaa | 240 |
| gaaattaaag | aaaacaccaa | aaatgataaa | caatggtgc | agtatatcta | taaatatacc | 300 |
| agctatccgg | atccgattct | gctgatgaaa | agcgcacgta | atagctgttg | gagcaaagat | 360 |
| gcagaatatg | gcctgtatag | catttatcag | ggtggcattt | ttgaactgaa | agaaaatgat | 420 |
| cgcattttg | tgagcgtgac | cggtggtagc | ccgctgggtc | tggcaggccg | gttgttggtg | 480 |
| gtagccagga | tccgtatgtt | aaagaagccg | aaaatctgaa | aaaatattt | aatgccggtc | 540 |
| attctgatgt | tgcagataat | ggcaccctgt | tctgggtat | tctgaaaaat | tggaaagaag | 600 |
| aaagcgatcg | caaaatcatg | cagagccaga | tcgtgagctt | ttatttcaaa | ctgttcaaaa | 660 |
| attttaaaga | tgatcagagc | attcagaaaa | gcgtggaaac | cattaaagaa | gacatgaacg | 720 |
| taaaattctt | caattccaat | aaaaaaaaac | gcgatgattt | cgaaaaactg | accaattata | 780 |
| gcgtgaccga | tctgaatgtt | cagcgtaaag | ccattcatga | actgattcag | gttatggcag | 840 |
| aactgtctcc | ggcagca | | | | | 857 |

<210> SEQ ID NO 35
<211> LENGTH: 928
<212> TYPE: DNA
<213> ORGANISM: Artificial Sequence
<220> FEATURE:
<223> OTHER INFORMATION: synthesized, encoding a fusion protein
comprising: a fragment of TRAIL protein, fragment of human
interferon gamma, flexible glycine-serine linkers and fragments
recognized by urokinase and metalloprotease MMP.

<400> SEQUENCE: 35

| | | | | | |
|---|---|---|---|---|---|
| caggatccgt | atgttaaaga | agcagaaaat | ctgaaaaaat | atttaatgc | aggtcatagc | 60 |
| gatgttgcag | ataatggtac | actgtttctg | ggtattctga | aaaattggaa | agaagaaagc | 120 |
| gatcgtaaaa | tcatgcagag | ccagattgtg | agcttctatt | ttaaactgtt | caaaaatttt | 180 |
| aaagatgatc | agagcattca | gaaaagcgtg | gaaaccatca | agaagatat | gaacgttaaa | 240 |
| ttttcaata | gcaacaaaaa | aaaacgtgat | gattttgaaa | aactgaccaa | ctatagcgtg | 300 |
| accgatctga | atgttcagcg | taaagcaatt | catgaactga | ttcaggttat | ggcagaactg | 360 |
| agtccggcag | caggtagcgg | tggtggtccg | ctgggtctgg | caggtcgtgt | gttcgtggta | 420 |
| gcggaggtgg | tgaacgtggt | ccgcagcgtg | ttgcagcaca | tattaccgga | cccgtggtcg | 480 |
| tagcaatacc | ctgagcagcc | cgaatagcaa | aaatgaaaaa | gcactgggtc | gtaaaattaa | 540 |
| tagctgggaa | agcagccgta | gcggtcatag | ctttctgagc | aatctgcatc | tgcgtaatgg | 600 |
| tgaactggtt | attcatgaaa | aaggttttta | ttatatttat | agccagacct | attttcgttt | 660 |
| tcaggaagaa | attaaagaaa | ataccaaaaa | tgataagcag | atggttcagt | acatttataa | 720 |
| ataccagc | tatccggatc | cgattctgct | gatgaaaagc | gcacgtaata | gctgttggag | 780 |
| caaagatgca | gaatatggtc | tgtatagcat | ttatcagggt | ggtattttg | aactgaaaga | 840 |
| aaatgatcgt | attttgtta | gcgttaccaa | tgaacatctg | attgatatgg | atcatgaagc | 900 | gagctttttt ggtgcatttc tggttggt                                       928

<210> SEQ ID NO 36
<211> LENGTH: 929
<212> TYPE: DNA
<213> ORGANISM: Artificial Sequence
<220> FEATURE:
<223> OTHER INFORMATION: synthesized, encoding a fusion protein
      comprising: a fragment of TRAIL protein, fragment of human
      interferon gamma, flexible glycine-serine linkers and fragments
      recognized by urokinase and metalloprotease MMP

<400> SEQUENCE: 36
cgtggtccgc agcgtgttgc agcacatatt accggcaccc gtggtcgtag caataccctg    60
agcagcccga atagcaaaaa tgaaaaagca ctgggtcgta aaattaatag ctgggaaagc   120
agccgtagcg gtcatagctt tctgagcaat ctgcatctgc gtaatggtga actggttatt   180
catgaaaaag ttttttatta tatttatagc cagacctatt tcgttttca ggaagaaatt    240 aaagaaaata ccaaaaatga taagcagatg gttcagtaca tttataaata taccagctat   300
ccggatccga ttctgctgat gaaaagcgca cgtaatagct gttggagcaa agatgcagaa   360
tatggtctgt atagcattta tcagggtggt attttttgaac tgaaagaaaa tgatcgtatt   420
tttgttagcg ttaccaatga acatctgatt gatatggatc atgaagcgag ctttttggt    480 gcatttctgg ttggtggtag cggtggtggt ccgctgggtc tggcaggtcg gttgttcgtg   540
gtagcggagg tggtgaacag gatccgtatg ttaaagaagc agaaaatctg aaaaaatatt   600
ttaatgcagg tcatagcgat gttgcagata atggtacact gtttctgggt attctgaaaa   660
attggaaaga agaaagcgat cgtaaaatca tgcagagcca gattgtgagc ttctattta    720 aactgttcaa aaattttaaa gatgatcaga gcattcagaa aagcgtggaa accatcaaag   780
aagatatgaa cgttaaattt ttcaatagca acaaaaaaaa acgtgatgat tttgaaaaac   840
tgaccaacta tagcgtgacc gatctgaatg ttcagcgtaa agcaattcat gaactgattc   900
aggttatggc agaactgagt ccggcagca                                      929

<210> SEQ ID NO 37
<211> LENGTH: 948
<212> TYPE: DNA
<213> ORGANISM: Artificial Sequence
<220> FEATURE:
<223> OTHER INFORMATION: synthesized, encoding a fusion protein
      comprising: a fragment of TRAIL protein, fragment of human
      interferon gamma, flexible glycine-serine linkers, a linker for
      pegylation and fragments recognized by urokinase and
      metalloprotease MMP

<400> SEQUENCE: 37
caggatccgt atgttaaaga agcagaaaat ctgaaaaaat attttaatgc aggtcatagc    60
gatgttgcag ataatggtac actgtttctg ggtattctga aaattggaa agaagaaagc   120 gatcgtaaaa tcatgcagag ccagattgtg agcttctatt taaaactgtt caaaaatttt   180
aaagatgatc agagcattca gaaaagcgtg gaaaccatca agaagatat gaacgttaaa   240 tttttcaata gcaacaaaaa aaaacgtgat gattttgaaa aactgaccaa ctatagcgtg   300
accgatctga atgttcagcg taaagcaatt catgaactga ttcaggttat ggcagaactg   360
agtccggcag caggtagcgg tggcggtccg ctgggtctgg caggtcgtc gctgcggtcc   420 ggaacgtgtt gttcgtggta gcggaggcgg tgaacgtggt ccgcagcggt tgcagcacat   480
attaccggca cccgtggtcg tagcaatacc ctgagcagcc cgaatagcaa aaatgaaaaa   540

```
gcactgggtc gtaaaattaa tagctgggaa agcagccgta gcggtcatag ctttctgagc      600
aatctgcatc tgcgtaatgg tgaactggtt attcatgaaa aaggttttta ttatatttat      660
agccagacct attttcgttt tcaggaagaa attaaagaaa ataccaaaaa tgataagcag      720
atggttcagt acattataa atataccagc tatccggatc cgattctgct gatgaaaagc       780
gcacgtaata gctgttggag caaagatgca gaatatggtc tgtatagcat ttatcagggt      840 ggtattttg aactgaaaga aaatgatcgt attttgtta gcgttaccaa tgaacatctg        900
attgatatgg atcatgaagc gagctttttt ggtgcatttc tggttggt                    948
```

<210> SEQ ID NO 38
<211> LENGTH: 1014
<212> TYPE: DNA
<213> ORGANISM: Artificial Sequence
<220> FEATURE:
<223> OTHER INFORMATION: synthesized, encoding a fusion protein
      comprising: a fragment of TRAIL protein, fragment of human
      interferon gamma, flexible glycine-serine linkers, a linker for
      pegylation and fragments recognized by urokinase and
      metalloprotease MMP

<400> SEQUENCE: 38

```
caggatccgt atgttaaaga agccgagaac ctgaaaaaat attttaatgc cggtcattcc      60
gatgttgcag ataatggcac cctgtttctg ggtattctga aaaattggaa agaggaaagc     120
gaccgcaaaa tcatgcagag ccagattgtg agcttctatt tcaaactgtt caaaaacttc    180
aaagacgacc agagcattca gaaaagcgtg gaaaccatca agaagatat gaacgtcaaa     240 ttcttcaaca gcaacaaaaa aaaacgcgac gactttgaga aactgaccaa ttatagcgtg    300
accgatctga atgttcagcg taaagcaatt catgaactga ttcaggttat ggcagaactg    360
agtccggcag caggtagcgg tggtggtccg ctgggtctgg caggtcgtgt tgttcgtgca    420
agcggttgtg gtccggaagg tagtggtggt ggcaccagcg aagaaaccat tagcaccgtt    480
caagaaaaac agcagaatat tagtccgctg gttcgtgaac gtggtccgca gcgtgttgca    540
gcacatatta ccggcacccg tggtcgtagc aatacccctga gcagcccgaa tagcaaaaat    600
gaaaaagcac tgggtcgcaa aatcaatagc tgggaaagca gccgtagcgg tcatagcttt    660
ctgagcaatc tgcatctgcg taatggtgaa ctggtgattc atgaaaaagg cttctactat    720
atctacagcc agacctattt tcgcttccaa gaagaaatca agagaacac caaaaacgac     780 aaacaaatgg tgcagtacat ctacaaatat accagctatc cggatccgat tctgctgatg    840
aaaagcgcac gtaatagctg ttggagcaaa gatgcagaat atggtctgta tagcatttat    900
cagggtggca tctttgagct gaaagaaaat gatcgcatct tgttagcgt gaccaacgaa     960 catctgatcg atatggatca tgaagccagc ttttttggtg catttctggt gggt          1014
```

<210> SEQ ID NO 39
<211> LENGTH: 951
<212> TYPE: DNA
<213> ORGANISM: Artificial Sequence
<220> FEATURE:
<223> OTHER INFORMATION: synthesized, encoding a fusion protein
      comprising: a fragment of TRAIL protein, fragment of human
      interferon gamma, flexible glycine-serine linkers, a linker for
      pegylation and fragments recognized by urokinase and
      metalloprotease MMP

<400> SEQUENCE: 39

```
gaacgtggtc cgcagcgtgt tgcagcacat attaccggca cccgtggtcg tagcaatacc       60
```

```
ctgagcagcc cgaatagcaa aaatgaaaaa gcactgggtc gtaaaattaa tagctgggaa      120
agcagccgta gcggtcatag ctttctgagc aatctgcatc tgcgtaatgg tgaactggtt      180
attcatgaaa aaggttttta ttatatttat agccagacct attttcgttt tcaggaagaa      240
attaaagaaa ataccaaaaa tgataagcag atggttcagt acatttataa atataccagc      300
tatccggatc cgattctgct gatgaaaagc gcacgtaata gctgttggag caaagatgca      360
gaatatggtc tgtatagcat ttatcagggt ggtattttg aactgaaaga aaatgatcgt       420 attttttgtta gcgttaccaa tgaacatctg attgatatgg atcatgaagc gagcttttt    480 ggtgcatttc tggttggtgg tagcggtggc ggtccgctgg gtctggcagg tgcgtctggc     540
tgcggtccgg aacgtgttgt tcgtggtagc ggaggcggtc aggatccgta tgttaaagaa    600
gcagaaaatc tgaaaaaata ttttaatgca ggtcatagcg atgttgcaga taatggtaca     660
ctgtttctgg gtattctgaa aaattggaaa gaagaaagcg atcgtaaaat catgcagagc    720
cagattgtga gcttctattt taaactgttc aaaaatttta agatgatca gagcattcag      780 aaaagcgtgg aaaccatcaa agaagatatg aacgttaaat ttttcaatag caacaaaaaa    840
aaacgtgatg attttgaaaa actgaccaac tatagcgtga ccgatctgaa tgttcagcgt    900
aaagcaattc atgaactgat tcaggttatg gcagaactga gtccggcagc a             951
```

<210> SEQ ID NO 40
<211> LENGTH: 1347
<212> TYPE: DNA
<213> ORGANISM: Artificial Sequence
<220> FEATURE:
<223> OTHER INFORMATION: synthesized, encoding a fusion protein
      comprising: a fragment of TRAIL protein, fragment of human
      interferon gamma, flexible glycine-serine linkers and fragments
      recognized by urokinase and metalloprotease MMP.

<400> SEQUENCE: 40

```
caggatccgt atgttaaaga agccgagaac ctgaaaaaat attttaatgc cggtcattcc      60
gatgttgcag ataatggcac cctgtttctg ggtattctga aaattggaa agaggaaagc     120 gatcgcaaaa tcatgcagag ccagattgtg agcttctatt ttaaactgtt caaaaatttt     180
aaagatgatc agagcattca gaaaagcgtg gaaaccatca agaagatat gaacgttaaa     240 tttttcaata gcaacaaaaa aaaacgtgat gattttgaaa actgaccaa ctatagcgtg    300 accgatctga atgttcagcg taaagcaatt gatgaactga ttcaggtgat ggcagaatt      360 agcaccgaag aacagcaaga gggtccttat gtgaaagaag cagaaaatct gaaaaaatac    420
ttcaacgcag tcatagcga cgttgccgat aacggtacac tgttcctggg catcctgaaa    480
aactggaaag aagaatcaga tcgtaaaatc atgcaatccc agatcgtgtc cttctacttc    540
aaactgttca aaacttcaa agacgaccag tcaatccaga atcagtggaa acgattaaa     600 gaagatatga acgtcaaatt cttcaattca acaaaaaaa acgcgacga cttcgagaaa    660 ctgacgaatt attcagttac cgatctgaac gtgcaacgca aagccatcca tgagctgatc    720
caggttatgg ccgaactgag tccggcagca aaaaccggta acgtaaacg tagccagatg    780 ctgtttcgtg gtagcggtgg tggtccgctg gtctggcag gtcgtgttgt tcgtggttca    840
ggtggtggtg aacgtggtcc gcagcgtgtt gcagcacata ttaccggcac ccgtggtcgt    900
agcaataccc tgagcagccc gaatagcaaa aatgaaaaag cactgggtcg caaaatcaat    960
agctgggaaa gcagccgtag cggtcatagc tttctgagca atctgcatct gcgtaatggt   1020
gaactggtga ttcatgaaaa aggctttat tatatttata gccagaccta ttttcgcttt   1080
```

```
caagaagaga ttaaagaaaa taccaaaaat gataaacaaa tggtgcagta catttataaa    1140
tataccagct atccggaccc gattctgctg atgaaaagcg cacgtaatag ctgttggagc    1200
aaagatgcag aatatggtct gtatagcatt tatcagggtg gcatctttga gctgaaagaa    1260
aatgatcgca tctttgttag cgtgaccaac gaacatctga tcgatatgga tcatgaagcc    1320
agcttttttg gtgcatttct ggtgggt                                        1347
```

<210> SEQ ID NO 41
<211> LENGTH: 1350
<212> TYPE: DNA
<213> ORGANISM: Artificial Sequence
<220> FEATURE:
<223> OTHER INFORMATION: synthesized, encoding a fusion protein
      comprising: a fragment of TRAIL protein, fragment of human
      interferon gamma, flexible glycine-serine linkers and fragments
      recognized by urokinase and metalloprotease MMP.

<400> SEQUENCE: 41

```
gaacgtggtc cgcagcgtgt tgcagcacat attaccggca cccgtggtcg tagcaatacc    60
ctgagcagcc cgaatagcaa aaatgaaaaa gcactgggtc gcaaaatcaa tagctgggaa    120
agcagccgta gcggtcatag ctttctgagc aatctgcatc tgcgtaatgg tgaactggtg    180
attcatgaaa aaggctttta ttatatttat agccagacct attttcgctt tcaagaagag    240
attaaagaaa ataccaaaaa tgataaacaa atggtgcagt acatttataa atataccagc    300
tatccggacc cgattctgct gatgaaaagc gcacgtaata gctgttggag caaagatgca    360
gaatatggtc tgtatagcat ttatcagggt ggcatctttg agctgaaaga aaatgatcgc    420
atctttgtta gcgtgaccaa cgaacatctg atcgatatgg atcatgaagc cagcttttt    480 ggtgcatttc tggtgggtgg tagcggtggt ggtccgctgg gtctggcagg tcgtgttgtt    540
cgtggttcag gtggtggtga acaggatccg tatgttaaag aagccgagaa cctgaaaaaa    600
tattttaatg ccggtcattc cgatgttgca gataatggca ccctgtttct gggtattctg    660
aaaaattgga agaggaaag cgatcgcaaa atcatgcaga gccagattgt gagcttctat    720
tttaaactgt tcaaaaattt taaagatgat cagagcattc agaaaagcgt ggaaaccatc    780
aaagaagata tgaacgttaa atttttcaat agcaacaaaa aaaaacgtga tgattttgaa    840
aaactgacca actatagcgt gaccgatctg aatgttcagc gtaaagcaat tgatgaactg    900
attcaggtga tggcagaatt tagcaccgaa gaacagcaag agggtcctta tgtgaaagaa    960
gcagaaaatc tgaaaaaata cttcaacgca ggtcatagcg acgttgccga taacggtaca    1020
ctgttcctgg gcatcctgaa aaactggaaa gaagaatcag atcgtaaaat catgcaatcc    1080
cagatcgtgt ccttctactt caaactgttc aaaaacttca agacgacca gtcaatccag    1140 aaatcagtgg aaacgattaa agaagatatg aacgtcaaat tcttcaattc aaacaaaaaa    1200
aaacgcgacg acttcgagaa actgacgaat tattcagtta ccgatctgaa cgtgcaacgc    1260
aaagccatcc atgagctgat ccaggttatg gccgaactga gtccggcagc aaaaaccggt    1320
aaacgtaaac gtagccagat gctgtttcgt                                     1350
```

<210> SEQ ID NO 42
<211> LENGTH: 1368
<212> TYPE: DNA
<213> ORGANISM: Artificial Sequence
<220> FEATURE:
<223> OTHER INFORMATION: synthesized, encoding a fusion protein
      comprising: a fragment of TRAIL protein, fragment of human
      interferon gamma, flexible glycine-serine linkers, linker for
      pegylation and fragments recognized by urokinase and metalloprotease MMP.

<400> SEQUENCE: 42

```
caggatccgt atgttaaaga agccgagaac ctgaaaaaat attttaatgc cggtcattcc     60
gatgttgcag ataatggcac cctgtttctg ggtattctga aaaattggaa agaggaaagc    120
gatcgcaaaa tcatgcagag ccagattgtg agcttctatt ttaaactgtt caaaaatttt    180
aaagatgatc agagcattca gaaaagcgtg gaaaccatca agaagatat gaacgttaaa     240
tttttcaata gcaacaaaaa aaaacgtgat gattttgaaa aactgaccaa ctatagcgtg    300
accgatctga tgttcagcg taaagcaatt gatgaactga ttcaggtgat ggcagaattt    360
agcaccgaag aacagcaaga gggtccttat gtgaaagaag cagaaaatct gaaaaaatac    420
ttcaacgcag gtcatagcga cgttgccgat aacggtacac tgttcctggg catcctgaaa    480
aactggaaag aagaatcaga tcgtaaaatc atgcaatccc agatcgtgtc cttctacttc    540
aaactgttca aaaacttcaa agacgaccag tcaatccaga atcagtgga acgattaaa     600
gaagatatga acgtcaaatt cttcaattca acaaaaaaa acgcgacga cttcgagaaa    660
ctgacgaatt attcagttac cgatctgaac gtgcaacgca aagccatcca tgagctgatc    720
caggttatgg ccgaactgag tccggcagca aaaaccggta acgtaaacg tagccagatg    780
ctgtttcgtg gtagcggtgg tggtccgctg ggtctggcag gtgcgtctgg ctgcggtccg    840
gaacgtgttg ttcgtggttc aggtggtggt gaacgtggtc cgcagcgtgt tgcagcacat    900
attaccggca cccgtggtcg tagcaatacc ctgagcagcc cgaatagcaa aaatgaaaaa    960
gcactgggtc gcaaaatcaa tagctgggaa agcagccgta gcggtcatag ctttctgagc   1020
aatctgcatc tgcgtaatgg tgaactggtg attcatgaaa aaggcttttta ttatatttat   1080
agccagacct attttcgctt tcaagaagag attaaagaaa ataccaaaaa tgataaacaa   1140
atggtgcagt acatttataa atataccagc tatccggacc cgattctgct gatgaaaagc   1200
gcacgtaata gctgttggag caaagatgca gaatatggtc tgtatagcat ttatcagggt   1260
ggcatctttg agctgaaaga aaatgatcgc atctttgtta gcgtgaccaa cgaacatctg   1320
atcgatatgg atcatgaagc cagcttttttt ggtgcatttc tggtgggt              1368
```

<210> SEQ ID NO 43
<211> LENGTH: 1368
<212> TYPE: DNA
<213> ORGANISM: Artificial Sequence
<220> FEATURE:
<223> OTHER INFORMATION: synthesized, encoding a fusion protein
    comprising: a fragment of TRAIL protein, fragment of human
    interferon gamma, flexible glycine-serine linkers, linker for
    pegylation and fragments recognized by urokinase and
    metalloprotease MMP.

<400> SEQUENCE: 43

```
gaacgtggtc cgcagcgtgt tgcagcacat attaccggca cccgtggtcg tagcaatacc     60
ctgagcagcc cgaatagcaa aaatgaaaaa gcactgggtc gcaaaatcaa tagctgggaa    120
agcagccgta gcggtcatag ctttctgagc aatctgcatc tgcgtaatgg tgaactggtg    180
attcatgaaa aaggcttttta ttatatttat agccagacct attttcgctt tcaagaagag    240
attaaagaaa ataccaaaaa tgataaacaa atggtgcagt acatttataa atataccagc    300
tatccggacc cgattctgct gatgaaaagc gcacgtaata gctgttggag caaagatgca    360
gaatatggtc tgtatagcat ttatcagggt ggcatctttg agctgaaaga aaatgatcgc    420
atctttgtta gcgtgaccaa cgaacatctg atcgatatgg atcatgaagc cagcttttttt    480
```

```
ggtgcatttc tggtgggtgg tagcggtggt ggtccgctgg gtctggcagg tgcgtctggc    540
tgcggtccgg aacgtgttgt tcgtggttca ggtggtggtc aggatccgta tgttaaagaa    600
gccgagaacc tgaaaaaata ttttaatgcc ggtcattccg atgttgcaga taatggcacc    660
ctgtttctgg gtattctgaa aaattggaaa gaggaaagcg atcgcaaaat catgcagagc    720
cagattgtga gcttctattt taaactgttc aaaaatttta agatgatca gagcattcag    780 aaaagcgtgg aaaccatcaa agaagatatg aacgttaaat ttttcaatag caacaaaaaa    840
aaacgtgatg attttgaaaa actgaccaac tatagcgtga ccgatctgaa tgttcagcgt    900
aaagcaattg atgaactgat tcaggtgatg cagaattta gcaccgaaga cagcaagag    960 ggtccttatg tgaaagaagc agaaaatctg aaaaaatact caacgcagg tcatagcgac    1020 gttgccgata acgtacact gttcctgggc atcctgaaaa actggaaaga agaatcagat    1080
cgtaaaatca tgcaatccca gatcgtgtcc ttctacttca aactgttcaa aaacttcaaa    1140
gacgaccagt caatccagaa atcagtggaa acgattaaag aagatatgaa cgtcaaattc    1200
ttcaattcaa acaaaaaaaa acgcgacgac ttcgagaaac tgacgaatta ttcagttacc    1260
gatctgaacg tgcaacgcaa agccatccat gagctgatcc aggttatggc cgaactgagt    1320
ccggcagcaa aaaccggtaa acgtaaacgt agccagatgc tgtttcgt                 1368
```

<210> SEQ ID NO 44
<211> LENGTH: 538
<212> TYPE: PRT
<213> ORGANISM: Artificial Sequence
<220> FEATURE:
<223> OTHER INFORMATION: synthesized, a fusion protein comprising: a
      fragment of TRAIL protein, a single chain pseudodimer of human
      interferon alpha 2b, a linker for pegylation and fragments
      recognized by urokinase and metalloprotease MMP.

<400> SEQUENCE: 44

```
Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu Gly Gly Gly Ser Pro Leu Gly Leu Ala Gly
                165                 170                 175

Arg Val Val Arg Ser Gly Gly Gly Ser Glu Lys Ser Arg Leu Ser
            180                 185                 190
```

-continued

```
Glu Gln Leu Asn Thr Ser Leu Ser Phe Ser Arg Met Ile Glu Ala Arg
        195                 200                 205

Val Val Glu Trp Ala Cys Pro Ser Tyr Lys Lys Glu Lys Leu Tyr Leu
    210                 215                 220

Thr Ile Arg Gln Phe Tyr Phe Arg Val Ala Leu Ile Ser Asp Glu Lys
225                 230                 235                 240

Met Leu Pro Thr Glu Thr Val Gly Val Gly Gln Ile Val Cys Ala Glu
                245                 250                 255

Leu Asp Asn Leu Gln Gln Tyr Leu Glu Thr Tyr Phe Lys Asp Leu Leu
            260                 265                 270

Thr Glu Asp Trp Ala Ala Ser Ser Asp Lys Thr Ser Phe Leu Asn Phe
        275                 280                 285

Ile Gln Gln Ile Met Glu His Leu Val Pro Ile Thr Glu Ala Lys Gln
    290                 295                 300

Phe Gln Asn Gly Phe Glu Glu Gln Pro Phe Gly Phe Asp His Arg Asp
305                 310                 315                 320

Lys Leu Cys Ser Phe Leu Ser Ile Arg Arg Met Gln Ala Leu Leu Met
                325                 330                 335

Leu Thr Arg Arg Ser Gly Leu Ser His Thr Gln Pro Leu Asp Cys Pro
            340                 345                 350

Leu Gly Leu Ala Gly Arg Val Val Arg Ala Ser Gly Cys Gly Pro Glu
        355                 360                 365

Pro Leu Gly Leu Ala Gly Arg Val Val Arg Val Ala Ala His Ile Thr
    370                 375                 380

Gly Thr Arg Gly Arg Ser Asn Thr Leu Ser Ser Pro Asn Ser Lys Asn
385                 390                 395                 400

Glu Lys Ala Leu Gly Arg Lys Ile Asn Ser Trp Glu Ser Ser Arg Ser
                405                 410                 415

Gly His Ser Phe Leu Ser Asn Leu His Leu Arg Asn Gly Glu Leu Val
            420                 425                 430

Ile His Glu Lys Gly Phe Tyr Tyr Ile Tyr Ser Gln Thr Tyr Phe Arg
        435                 440                 445

Phe Gln Glu Glu Ile Lys Glu Asn Thr Lys Asn Asp Lys Gln Met Val
    450                 455                 460

Gln Tyr Ile Tyr Lys Tyr Thr Ser Tyr Pro Asp Pro Ile Leu Leu Met
465                 470                 475                 480

Lys Ser Ala Arg Asn Ser Cys Trp Ser Lys Asp Ala Glu Tyr Gly Leu
                485                 490                 495

Tyr Ser Ile Tyr Gln Gly Gly Ile Phe Glu Leu Lys Glu Asn Asp Arg
            500                 505                 510

Ile Phe Val Ser Val Thr Asn Glu His Leu Ile Asp Met Asp His Glu
        515                 520                 525

Ala Ser Phe Phe Gly Ala Phe Leu Val Gly
    530                 535
```

<210> SEQ ID NO 45
<211> LENGTH: 384
<212> TYPE: PRT
<213> ORGANISM: Artificial Sequence
<220> FEATURE:
<223> OTHER INFORMATION: synthesized, a fusion protein comprising: a
      fragment of TRAIL protein, a consensus sequence of human
      interferon alpha, a linker for pegylation, flexible glycine-serine
      linker and fragments recognized by urokinase and metalloprotease
      MMP.

```
<400> SEQUENCE: 45

Ser Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Trp Asp Glu Ser
65                  70                  75                  80

Leu Leu Glu Lys Phe Tyr Thr Glu Leu Tyr Gln Gln Leu Asn Asp Leu
                85                  90                  95

Glu Ala Cys Val Ile Gln Glu Val Gly Val Glu Thr Pro Leu Met
            100                 105                 110

Asn Val Asp Ser Ile Leu Ala Val Lys Lys Tyr Phe Gln Arg Ile Thr
            115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Ile Ser Thr Asn Leu Gln Glu
145                 150                 155                 160

Arg Leu Arg Arg Lys Glu Gly Ser Gly Pro Leu Gly Leu Ala Gly
                165                 170                 175

Arg Val Val Arg Ala Ser Gly Cys Gly Pro Glu Pro Leu Gly Leu Ala
            180                 185                 190

Gly Arg Val Val Arg Thr Ser Glu Glu Thr Ile Ser Thr Val Gln Glu
    195                 200                 205

Lys Gln Gln Asn Ile Ser Pro Leu Val Arg Glu Arg Gly Pro Gln Arg
210                 215                 220

Val Ala Ala His Ile Thr Gly Thr Arg Gly Arg Ser Asn Thr Leu Ser
225                 230                 235                 240

Ser Pro Asn Ser Lys Asn Glu Lys Ala Leu Gly Arg Lys Ile Asn Ser
                245                 250                 255

Trp Glu Ser Ser Arg Ser Gly His Ser Phe Leu Ser Asn Leu His Leu
            260                 265                 270

Arg Asn Gly Glu Leu Val Ile His Glu Lys Gly Phe Tyr Tyr Ile Tyr
        275                 280                 285

Ser Gln Thr Tyr Phe Arg Phe Gln Glu Glu Ile Lys Glu Asn Thr Lys
    290                 295                 300

Asn Asp Lys Gln Met Val Gln Tyr Ile Tyr Lys Tyr Thr Ser Tyr Pro
305                 310                 315                 320

Asp Pro Ile Leu Leu Met Lys Ser Ala Arg Asn Ser Cys Trp Ser Lys
                325                 330                 335

Asp Ala Glu Tyr Gly Leu Tyr Ser Ile Tyr Gln Gly Gly Ile Phe Glu
            340                 345                 350

Leu Lys Glu Asn Asp Arg Ile Phe Val Ser Val Thr Asn Glu His Leu
        355                 360                 365

Ile Asp Met Asp His Glu Ala Ser Phe Phe Gly Ala Phe Leu Val Gly
    370                 375                 380

<210> SEQ ID NO 46
<211> LENGTH: 351
<212> TYPE: PRT
<213> ORGANISM: Artificial Sequence
```

<220> FEATURE:
<223> OTHER INFORMATION: a pseudodimer of interferon alpha 2b

<400> SEQUENCE: 46

```
Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu Gly Gly Gly Ser Pro Leu Gly Leu Ala Gly
                165                 170                 175

Arg Val Val Arg Ser Gly Gly Gly Ser Glu Lys Ser Arg Leu Ser
                180                 185                 190

Glu Gln Leu Asn Thr Ser Leu Ser Phe Ser Arg Met Ile Glu Ala Arg
            195                 200                 205

Val Val Glu Trp Ala Cys Pro Ser Tyr Lys Lys Glu Lys Leu Tyr Leu
    210                 215                 220

Thr Ile Arg Gln Phe Tyr Phe Arg Val Ala Leu Ile Ser Asp Glu Lys
225                 230                 235                 240

Met Leu Pro Thr Glu Thr Val Gly Val Gly Gln Ile Val Cys Ala Glu
                245                 250                 255

Leu Asp Asn Leu Gln Gln Tyr Leu Glu Thr Tyr Phe Lys Asp Leu Leu
            260                 265                 270

Thr Glu Asp Trp Ala Ala Ser Ser Asp Lys Thr Ser Phe Leu Asn Phe
        275                 280                 285

Ile Gln Gln Ile Met Glu His Leu Val Pro Ile Thr Glu Ala Lys Gln
    290                 295                 300

Phe Gln Asn Gly Phe Glu Gln Pro Phe Gly Phe Asp His Arg Asp
305                 310                 315                 320

Lys Leu Cys Ser Phe Leu Ser Ile Arg Arg Met Gln Ala Leu Leu Met
                325                 330                 335

Leu Thr Arg Arg Ser Gly Leu Ser His Thr Gln Pro Leu Asp Cys
            340                 345                 350
```

<210> SEQ ID NO 47
<211> LENGTH: 166
<212> TYPE: PRT
<213> ORGANISM: Artificial Sequence
<220> FEATURE:
<223> OTHER INFORMATION: a consensus sequence of human interferon alpha

<400> SEQUENCE: 47

| | | | | | | | | | | | | | | |
|---|---|---|---|---|---|---|---|---|---|---|---|---|---|---|
| Ser | Asp | Leu | Pro | Gln | Thr | His | Ser | Leu | Gly | Asn | Arg | Arg | Ala | Leu | Ile |
| 1 | | | | 5 | | | | | 10 | | | | | 15 | |

Leu Leu Ala Gln Met Arg Arg Ile Ser Pro Phe Ser Cys Leu Lys Asp
          20               25             30

Arg His Asp Phe Gly Phe Pro Gln Glu Glu Phe Asp Gly Asn Gln Phe
        35               40              45

Gln Lys Ala Gln Ala Ile Ser Val Leu His Glu Met Ile Gln Gln Thr
    50               55              60

Phe Asn Leu Phe Ser Thr Lys Asp Ser Ser Ala Ala Trp Asp Glu Ser
65               70              75              80

Leu Leu Glu Lys Phe Tyr Thr Glu Leu Tyr Gln Gln Leu Asn Asp Leu
             85              90             95

Glu Ala Cys Val Ile Gln Glu Val Gly Val Glu Thr Pro Leu Met
        100             105            110

Asn Val Asp Ser Ile Leu Ala Val Lys Lys Tyr Phe Gln Arg Ile Thr
        115             120            125

Leu Tyr Leu Thr Glu Lys Lys Tyr Ser Pro Cys Ala Trp Glu Val Val
   130               135              140

Arg Ala Glu Ile Met Arg Ser Phe Ser Ile Ser Thr Asn Leu Gln Glu
145              150              155            160

Arg Leu Arg Arg Lys Glu
            165

<210> SEQ ID NO 48
<211> LENGTH: 1614
<212> TYPE: DNA
<213> ORGANISM: Artificial Sequence
<220> FEATURE:
<223> OTHER INFORMATION: synthesized, encoding a fusion protein
    comprising: a fragment of TRAIL protein, a single chain
    pseudodimer of human interferon alpha 2b, a linker for pegylation
    and fragments recognized by urokinase and metalloprotease MMP.

<400> SEQUENCE: 48

```
tgtgatttac cacaaacaca ttcattagga tcaagaagaa cattaatgtt attagcacaa      60
atgagaagaa tatcattatt ttcatgttta aaggatagac atgattttgg atttccacaa     120
gaagaatttg gaatcaatt tcaaaaggca gaaacaatac cagtgttaca tgaaatgata     180
caacaaatat ttaatttatt ttcaacaaag gattcatcag cagcatggga tgaaacatta     240
ttagataagt tttatacaga attatatcaa caattaaatg atttagaagc atgtgtgata     300
caaggagtgg gagtgacaga aacaccatta atgaaggaag attcaatatt agcagtgaga     360
aagtattttc aaagaataac attatattta aaggaaaaga agtattcacc atgtgcatgg     420
gaagtggtga gagcagaaat aatgagatca ttttcattat caacaaattt acaagaatca     480
ttaagatcaa aggaaggagg aggaggatca ccattaggat tagcaggaag agtggtgaga     540
tcaggaggag gaggatcaga aaagtcaaga ttatcagaac aattaaatac atcattatca     600
ttttcaagaa tgatagaagc aagagtggtg gaatgggcat gtccatcata taagaaggaa     660 aagtatatt taacaataag acaattttat tttagagtgg cattaatatc agatgaaaag     720
atgttaccaa cagaaacagt gggagtggga caaatagtgt gtgcagaatt agataattta     780
caacaatatt tagaaacata ttttaaggat ttattaacag aagattgggc agcatcatca     840
gataagacat cattttttaaa ttttatacaa caaataatgg aacatttagt gccaataaca     900
gaagcaaagc aatttcaaaa tggatttgaa gaacaaccat ttggatttga tcatagagat     960
```

```
aagttatgtt cattttatc aataagaaga atgcaagcat tattaatgtt aacaagaaga    1020
tcaggattat cacatacaca accattagat tgtccattag gattagcagg aagagtggtg    1080
agagcatcag gatgtggacc agaaccatta ggattagcag gaagagtggt gagagtggca    1140
gcacatataa caggaacaag aggaagatca aatacattat catcaccaaa ttcaaagaat    1200
gaaaaggcat taggaagaaa gataaattca tgggaatcat caagatcagg acattcattt    1260
ttatcaaatt tacatttaag aaatggagaa ttagtgatac atgaaaaggg attttattat    1320
atatattcac aaacatattt tagatttcaa gaagaaataa aggaaaatac aaagaatgat    1380
aagcaaatgg tgcaatatat ataagtat acatcatatc cagatccaat attattaatg    1440
aagtcagcaa gaaattcatg ttggtcaaag gatgcagaat atggattata ttcaatatat    1500
caaggaggaa tatttgaatt aaaggaaaat gatagaaat ttgtgtcagt gacaaatgaa    1560
catttaatag atatggatca tgaagcatca tttttggag cattttagt ggga            1614
```

<210> SEQ ID NO 49
<211> LENGTH: 1152
<212> TYPE: DNA
<213> ORGANISM: Artificial Sequence
<220> FEATURE:
<223> OTHER INFORMATION: synthesized, encoding a fusion protein
      comprising: a fragment of TRAIL protein, a consensus sequence of
      human interferon alpha, a linker for pegylation, flexible
      glycine-serine linker and fragments recognized by urokinase and
      metalloprotease MMP.

<400> SEQUENCE: 49

```
tcagatttac cacaaacaca ttcattagga aatagaagag cattaatatt attagcacaa    60
atgagaagaa tatcaccatt tcatgtttta aaggatagac atgatttggg atttccacaa    120
gaagaatttg atggaaatca atttcaaaag gcacaagcaa tatcagtgtt acatgaaatg    180
atacaacaaa catttaattt attttcaaca aaggattcat cagcagcatg ggatgaatca    240
ttattagaaa agttttatac agaattatat caacaattaa atgatttaga agcatgtgtg    300
atacaagaag tgggagtgga agaaacacca ttaatgaatg tggattcaat attagcagtg    360
aagaagtatt ttcaaagaat aacattatat ttaacagaaa agaagtattc accatgtgca    420
tgggaagtgg tgagagcaga aataatgaga tcattttcaa tatcaacaaa tttacaagaa    480
agattaagaa gaaaggaagg aggatcagga ccattaggat tagcaggaag agtggtgaga    540
gcatcaggat gtggaccaga accattagga ttagcaggaa gagtggtgag aacatcagaa    600
gaaacaatat caacagtgca agaaaagcaa caaaatatat caccattagt gagagaaaga    660
ggaccacaaa gagtggcagc acatataaca ggaacaagag gaagatcaaa tacattatca    720
tcaccaaatt caagaatga aaaggcatta ggaagaaaga taaattcatg ggaatcatca    780
agatcaggac attcattttt atcaaattta catttaagaa atggagaatt agtgatacat    840
gaaaagggat ttattatat atattcacaa acatatttta gattcaaga gaaataaag    900 gaaaatacaa gaatgataa gcaaatggtg caatatatat ataagtatac atcatatcca    960
gatccaatat tattaatgaa gtcagcaaga aattcatgtt ggtcaaagga tgcagaatat    1020
ggattatatt caatatatca aggaggaata tttgaattaa aggaaaatga tagaaatttt    1080
gtgtcagtga caaatgaaca tttaatagat atggatcatg aagcatcatt ttttggagca    1140 ttttagtgg ga                                                       1152
```

<210> SEQ ID NO 50

```
<211> LENGTH: 4
<212> TYPE: PRT
<213> ORGANISM: Artificial Sequence
<220> FEATURE:
<223> OTHER INFORMATION: synthesized, a steric linker

<400> SEQUENCE: 50

Gly Gly Ser Gly
1

<210> SEQ ID NO 51
<211> LENGTH: 19
<212> TYPE: DNA
<213> ORGANISM: Artificial Sequence
<220> FEATURE:
<223> OTHER INFORMATION: primer complementary to T7 promotor

<400> SEQUENCE: 51
taatacgact cactatagg                                                 19

<210> SEQ ID NO 52
<211> LENGTH: 19
<212> TYPE: DNA
<213> ORGANISM: Artificial Sequence
<220> FEATURE:
<223> OTHER INFORMATION: primer complementary to T7 terminator

<400> SEQUENCE: 52
gctagttatt gctcagcgg                                                 19
```

ANTICANCER FUSION PROTEIN COMPRISING TRAIL AND INTERFERON

RELATED APPLICATIONS

This application is a §371 national stage of PCT International Application No. PCT/EP2011/071719, filed Dec. 5, 2011, claims priority Polish Patent Applications PL394597, filed Apr. 18, 2011 and PL393146, filed Dec. 3, 2010, the contents of each of which are hereby incorporated by reference into this application.

REFERENCE TO SEQUENCE LISTINGS

This application incorporates-by-reference nucleotide and/or amino acid sequences which are present in the file named "150414_1947_85139_Substitute_Listing_AWG.txt", which is 104.0 kilobytes in size, and which was created Apr. 14, 2015in the IBM-PC machine format, having an operating system compatibility with MS-Windows, which is contained in the text file filed Apr. 14, 2015 as part of this application.

The invention relates to the field of therapeutic fusion proteins, in particular recombinant fusion proteins. More particularly, the invention relates to fusion proteins containing the fragment of a sequence of the soluble human TRAIL 5 protein in combination with a sequence of an immunostimulating peptide, pharmaceutical compositions containing them, their use in therapy, particularly as anticancer agents, and to polynucleotide sequences encoding the fusion proteins, expression vectors containing the polynucleotide sequences, and host cells containing these expression vectors.

TRAIL protein belonging to the cytokines family (Tumor Necrosis Factor-Related Apoptosis Inducing Ligand), also known as Apo2L (Apo2-ligand), is a potent activator of apoptosis in tumor cells and in cells infected by viruses. TRAIL is a ligand naturally occurring in the body. TRAIL protein, its amino acid sequence, coding DNA sequences and protein expression systems were disclosed for the first time in EP0835305A1.

TRAIL protein exerts its anticancer activity by binding to pro-apoptotic TRAIL surface receptors 1 and 2 (TRAIL-R1/R2) and subsequent activation of these receptors. These receptors, also known as DR4 and DR5 (death receptor 4 and death receptor 5), belong to the TNF receptor family and are overexpressed by different types of cancer cells. Activation of these receptors can induce external signaling pathway of apoptosis independent from suppressor gene p53, which by activated caspase-8 leads to the activation of executive caspases and thereby degradation of nucleic acids. Caspase-8 released upon TRAIL activation may also cause the release of Bid protein and thereby indirect activation of mitochondrial pathway, Bid protein being translocated to mitochondria, where it stimulates the release of cytochrome c, thus indirectly amplifying the apoptotic signal from death receptors.

TRAIL acts selectively on tumor cells essentially without inducing apoptosis in healthy cells which are resistant to this protein. Therefore, the enormous potential of TRAIL was recognized as an anticancer agent which acts on a wide range of different types of tumor cells, including hematologic malignancies and solid tumors, while sparing normal cells and exerting potentially relatively small side effects.

TRAIL protein is a type II membrane protein having the length of 281 amino acids, and its extracellular region comprising amino acid residues 114-281 upon cleavage by proteases forms soluble sTRAIL molecule of 20 kDa size, which is also biologically active. Both forms TRAIL and sTRAIL are capable of triggering apoptosis via interaction with TRAIL receptors present on target cells. Strong antitumor activity and very low systemic toxicity of soluble part of TRAIL molecule was demonstrated using cell lines tests.

Human clinical studies with recombinant human soluble TRAIL (rhTRAIL) having amino acid sequence corresponding to amino acids 114-281 of hTRAIL, known under the INN dulanermin, showed also its good tolerance and absence of dose limiting toxicity.

Fragment of TRAIL shorter than 114-281 was also found to be able to bind with membrane death receptors and induce apoptosis via these receptors, as recently reported for recombinant circularly permuted mutant of 122-281hTRAIL, for example in EP 1 688 498.

Toxic effects of recombinant TRAIL protein on liver cells reported up to now appeared to be associated with the presence of modification, i.e. polyhistidine tags, while untagged TRAIL showed no systemic toxicity.

However, in the course of further research and development it appeared that many cancer cells also showed primary or acquired resistance to TRAIL (see for example WO2007/022214). Although the mechanism of resistance to TRAIL has not been fully understood, it is believed that it may manifest itself at different levels of TRAIL-induced apoptosis pathway, ranging from the level of cell surface receptors to the executive caspases within the signaling pathway. This resistance limits the usefulness of TRAIL as an anticancer agent.

Furthermore, in clinical trials on patients the actual effectiveness of TRAIL as a monotherapy proved to be low. To overcome this low efficiency and the resistance of tumors to TRAIL, various combination therapies with radio- and chemo-therapeutic agents were designed, which resulted in synergistic apoptotic effect (WO2009/002947; A. Almasan and A. Ashkenazi, Cytokine Growth Factor Reviews 14 (2003) 337-348; R K Srivastava, Neoplasis, Vol 3, No 6, 2001, 535-546, Soria J C et al., J. Clin. Oncology, Vol 28, No 9 (2010), p. 1527-1533). The use of rhTRAIL for cancer treatment in combination with selected conventional chemotherapeutic agents (paclitaxel, carboplatin) and monoclonal anti-VEGF antibodies are described in WO2009/140469. However, such a combination necessarily implies well-known deficiencies of conventional chemotherapy or radiotherapy.

Constructed fusion protein containing sequences of angiogenesis inhibitor vasostatin and TRAIL linked with a metalloprotease cleavage site linker was described as exhibiting apoptosis-inducing effect in tumor cells by A. I. Guo et al in Chinese Journal of Biochemistry and Molecular Biology 2008, vol. 24(10), 925-930. Constructed fusion protein containing sequences Tumstatin183-230 of angiogenesis inhibitor tumstatin and TRAIL114-281 was described as exhibiting induction of apoptosis of pancreatic cancer cells by N. Ren et al in Academic Journal of Second Military Medical University 2008, vol. 28(5), 676-478.

US2005/244370 and corresponding WO2004/035794 disclose the construct of TRAIL95-281 as an effector domain linked by a peptide linker with extracellular part of another member of TNF family ligands CD40 as a cell surface binding domain. It is stated that activation of the construct is via binding of its CD40 part.

Moreover, the problem connected with TRAIL therapy has proved to be its low stability and rapid elimination from the body after administration.

Advantageous effect of cytokines in cancer therapy is also known. A member of the cytokines family is interferon, a protein that stimulates the immune system. Interferons are important anti-cancer agents or adjuncts anti-cancer therapeutics (Borden and Williams, Interferons, Cancer Medicine, 5th edition, 815-824, 2000). It has been shown that one of the effects of interferons is strong stimulation of multiple proapoptotic factors, including TRAIL ligand.

A representative of Type II inteferons group is interferon gamma (IFN-γ) which is a dimeric soluble cytokine. IFN-γ is secreted by NK, NKT, Th1, Tc, and dendritic cells. IFN-γ ligand binds to two types of IFN-γ receptor Rα and IFN-γ RB1 and activates the JAK-STAT pathway. One of its effects is the intense stimulation of human monocytes to produce TRAIL protein, which significantly affects their ability to eliminate cancer cells (Griffith et al, J. Exp. Med., 189:1343-1353, 1999).

Interferon gamma activates IFN gamma receptor, stimulating antibody-dependent toxicity and potentiates the process of connecting the cells with tumor cells. In addition, IFN gamma activates caspases, thereby inducing apoptosis in cancer cells. In addition, it has been demonstrated that in many tumor lines showing resistance to TRAIL-stimulated apoptosis interferon gamma acted synergistically, contributing to their sensitivity to TRAIL (Wang et al, Oncogene, 23: 928-935, 2004). However, existing therapies using IFN gamma were not sufficiently effective to find use in the treatment of cancer diseases.

Beneficial effects of interferon alpha on the induction of overproduction of TRAIL in myeloma, lymphomas and liver cancer cells has been also demonstrated (Chen and et al, Blood, 98: 2183-21192; Herzer et al, Cancer Res. 69(3): 855-862, 2009). Interferon alpha is considered to be a biological response modulator which strengthens natural responses of the organism to diseases. It affects both the cellular and humoral immunity. It stimulates the production of anti-cancer antibodies, activates the cytotoxic action of macrophages, NK cells and lymphocytes. INF alpha increases also the expression of HLA histocompatibility antigens on cancer cells, which facilitates their recognition by immune cells. It mediates the slowdown of growth and divisions of cancer cells, and consequently their death.

Interferon alpha has been used to treat various types of cancers, including hairy cell leukemia, melanoma, kidney cancer, myeloblastic and myelocytic leukemia, lymphoma, Kaposi's sarcoma and other neoplastic diseases of the blood (Folkman J., N. Engl. J. Med. 1995, 333: 1757-1763; Sidky Y A, Borden E C. Cancer Res. 1987. 47: 5155-5161; Iwagak H, Hizuta A, Yoshino T, et al, Anticancer Res. 1993, 13:13-15; Rubinger M, Plenderleith I H, Lertzman M, et al, Chest. 1995, 108:281-282). However, at the dose required to achieve therapeutic effect in patients, toxic effects such as neutropenia, flu-like symptoms, malaise, anorexia and liver dysfunction were observed. Because of these side effects, interferon alpha therapy is often interrupted, which makes this therapy ineffective. Moreover, the biological half-life of the majority of cytokines, including interferon-alpha, is short and lasts up to several hours, due to which frequent injections are needed. For various reasons, frequent use of the drug is inconvenient for the patient (especially in the long-term treatment). This resulted in the need of designing extended-release formulations of interferon-alpha.

Several attempts have been taken to improve interferon alpha properties. The attempt to extend the biological half-life of interferon by providing hetero-dimeric fusions with carrier proteins comprising linkers enabling proper folding of the expressed fusion proteins is disclosed for example in U.S. Pat. No. 7,943,733. Other attempts are based on resolved structure of the biologically active form of interferon, i.e. its naturally formed noncovalent homo-dimers which are formed by anti-parallel inter-locking of the two monomers at the receptor site a zinc ion ($Zn^{2+}$) (R. Radhakrishnan, Structure 1996, Vol. 4 No 12, 1453-1463). Constructs of homodimers of interferon alpha linked via glycine-serine linker are mentioned in patent application LT2010012, but their activity data are not provided.

IFNy is also known to act as noncovalently associated homodimer in which two identical polypeptide chains are oriented in an antiparallel manner to generate a symmetrical molecule (Ealick, S. E., Science (1991) 262, 698-702). Therefore, the possibility exists that IFNy dimeric forms could occupy the receptor binding site more efficient, but this hypothesis was not clinically confirmed.

Attempts to develop derivatives of alpha interferon that would be free of the above mentioned side effects resulted in the introduction to the treatment of long-acting pegylated alpha interferons. Pegylation is one of the popular methods of proteins administration into the body of mammals, aimed at reducing or overcoming side effects of the active substance. The principle of pegylation is creation of a protective barrier around the modified molecules, resulting in the extended time of the desired concentration of the substance (due to the change of pharmacokinetic and pharmacodynamic properties). Absorption time is elongated and the elimination from the body is longer.

Values of these parameters are dependent on the structure of polyethylene glycol (PEG) molecules: chain length, linearity, degree of branching, type and number of binding sites and on number of glycol molecules attached. [Delgado C, Francis G E, Fisher D., The uses and properties of PEG-linked proteins. Crit. Rev. Ther. Drug Carrier Syst. 1992; 9 (3-4): 249-304].

Pegylation does not affect the manner of binding of interferon to its receptor. Preclinical studies have demonstrated that pegylated interferon alpha binds to IFNα-2a receptor and exerts the same or higher biological activity in vitro, as confirmed in the tests on the tumor cell culture and on mice with implanted human renal carcinoma cells [Nieforth K, Nadeau R, Patel I H, Mould D. Use of an indirect pharmacodynamic stimulation model of MX protein induction to compare in vivo activity of interferon α-2a and a polyethylene glycol-modified derivative in healthy subjects, Clin. Pharmacol. Ther. 1996; 59: 636-46; Paul G, et al. Pegylated interferon—α-2b: Pharmacokinetics, pharmacodynamics, safety, and preliminary efficacy data. Clin. Pharmacol. Ther. 2000; 68: 556-67].

Despite promising data from animal model experiments, commercially available pegylated interferon-containing preparations PEGIntron® and PEGASYS® (G. Pasut, F. M. Veronese, Prog. Polym. Sci. 32 (2007) 933-961) with a 40 kDa branched and a 12 kDa linear PEG chains attached to IFNα, respectively, demonstrated safety profile qualitatively similar or even worse from the corresponding unmodified interferon molecules (Bukowski R. M. et al., *Cancer*, 95(2): 389-96 (2002); Bukowski R. M. et al., *Journal of Clinical Oncology*, 20(18):3841-3949 (2002); Motzer, R. J. et al., *J. Clin. Oncol.*, 19(5): 1312-9 (2001); Tong M. J., *Journal of Interferon and Cytokine Research*, 18:81-86 (1998); Yao G. B. et al., *Journal of Gastroenterology and Hepatolog.*, 15:1165-1170 (2000); Heathcote E. J. et al, *N. Engl. J. Med.*, 343(23):1673-80 (2000); Tong M. J. et al., *Hepatology;* 26(3):747-54 (1997)).

The most frequently observed side effects of pegylated IFNα therapy include: dose-dependent nausea, anorexia, stiffening of the muscles. In addition, longer therapy revealed dose-limiting, such as severe fatigue, neurotoxicity, liver malfunctioning and inhibition of bone marrow functions (PEG- Intron® at doses of 7.5 μg/kg and higher) (Bukowski R. M. et al., *Cancer;* 95(2):389-96 (2002)).

Therefore, despite the existence of clinically employed anti-cancer therapies based on both the TRAIL protein and proteins of the interferons family (also modified, in particular by pegy(ation), they are not sufficiently effective and have many well-known disadvantages, of which one of the most severe and restricting is limited effectiveness of treatment, lack of selectivity against cancer cells, side effects and primary or acquired resistance. There is still a need for improved cancer therapy based both on the activity of interferon and TRAIL protein, that would be both effective and selective in vivo against cancer cells. There remains an urgent and unmet need for new anticancer agents that would allow both to broaden the range of available agents and to find agents that are more effective (cytotoxic) and selective. There is also a need for new selective agents with increased stability and improved pharmacokinetics.

The present invention provides a solution of this problem by means of novel fusion proteins that incorporate a domain derived from TRAIL and a short effector peptide domain having the immune system stimulating activity, which effector peptide does not include TRAIL fragments, wherein the effector peptide potentiates or complements the action of TRAIL. Moreover, it turned out that in many cases the fusion proteins of the invention are more potent than soluble TRAIL and its variants consisting of fragments of its sequence, as well as more potent than respective effector peptides. In many cases, novel fusion proteins also overcome resistance to TRAIL. Moreover, the incorporation of the effector peptide results in prolonged half-life and increased retention of protein in the tumor and its enhanced efficiency. Additionally, in certain variants novel fusion proteins may be able to link PEG, which has protective effect against non-specific proteases and additionally alters pharmacokinetic and pharmacodynamic properties, particularly with respect to prolongation of the biological half-life.

DESCRIPTION OF FIGURES

The invention will now be described in detail with reference to the Figures of the drawing.

DETAILED DESCRIPTION OF THE INVENTION

Figure 1:
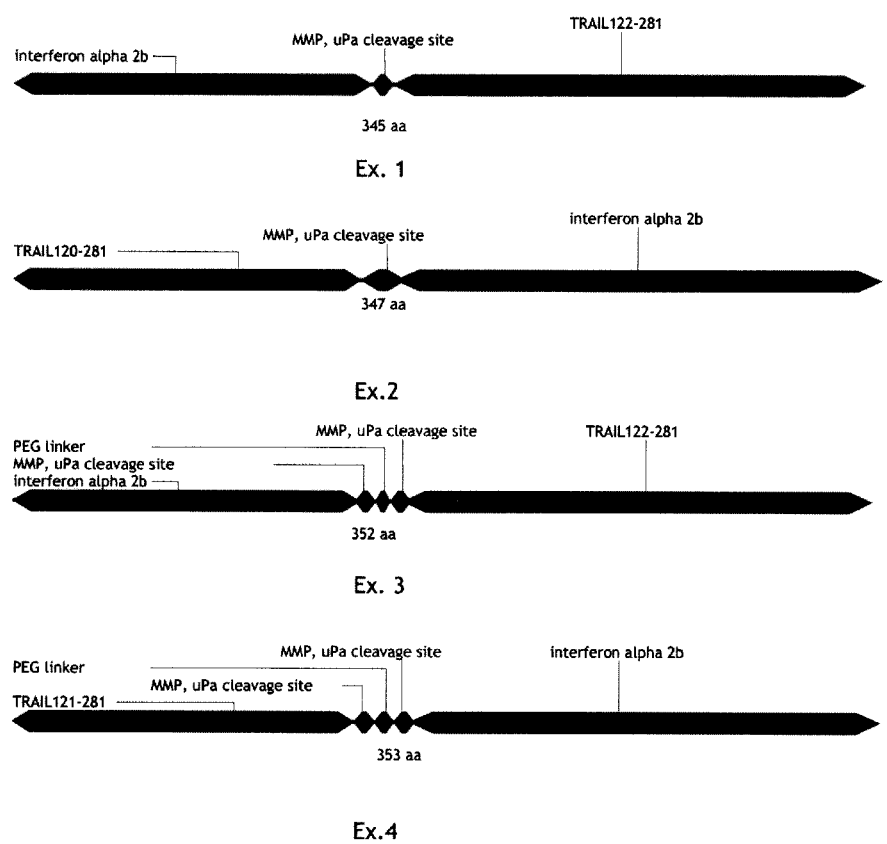
FIG. 1 presents schematic structures of fusion proteins of the invention according to Ex. 1, Ex.2, Ex. 3 and Ex. 4.

The invention relates to a fusion protein comprising:

domain (a) which is the functional fragment of a sequence of soluble hTRAIL protein, which fragment begins with an aminoacid at a position not lower than hTRAIL95, or a homolog of said functional fragment having at least 70% sequence identity, and domain (b) which is a sequence of an imunostimulating effector peptide, wherein the sequence of the domain (b) is attached at the C-terminus and/or N-terminus of domain (a).

The term "the functional soluble fragment of a sequence of soluble hTRAIL" should be understood as denoting any such fragment of soluble hTRAIL that is capable of inducing apoptotic signal in mammalian cells upon binding to its receptors on the surface of the cells.

It will be also appreciated by a skilled person that the existence of at least 70% homology of the TRAIL sequence is known in the art.

It should be understood that domain (b) of the effector peptide in the fusion protein of the invention is neither hTRAIL protein nor a part or fragment of hTRAIL protein.

The term "peptide" in accordance with the invention should be understood as a molecule built from plurality of amino acids linked together by means of a peptide bond. Thus, the term "peptide" according to the invention includes oligopeptides, polypeptides and proteins.

In the present invention the aminoacid sequences of peptides will be presented in a conventional manner adopted in the art, i.e. in the direction from N-terminus (N-end) of the peptide towards its C-terminus (C-end). Any sequence will thus have its N-terminus on the left side and C-terminus on the right side of its linear presentation.

The fusion protein of the invention may incorporate a single domain (b) of the effector peptide, attached at the C-terminus or N-terminus of domain (a).

In a particular embodiment, the domain (a) is a fragment of hTRAIL sequence, beginning with an amino acid from the range of hTRAIL95 to hTRAIL122, inclusive, and ending with the amino acid hTRAIL 281.

In particular, domain (a) may be selected from the group consisting of sequences corresponding to hTRAIL95-281, hTRAIL114-281, hTRAIL116-281, hTRAIL120-281, hTRAIL121-281 and hTRAIL122-281. It will be evident to those skilled in the art that hTRAIL95-281, hTRAIL114-281, hTRAIL116-281, hTRAIL120-281, hTRAIL121-281 and hTRAIL122-281 represent a fragment of human TRAIL protein starting with amino acid marked with the number 95, 114, 116, 120, 121 and 122, respectively, in the known sequence of hTRAIL published in GenBank under Accession No P50591.

In another particular embodiment, the domain (a) is a homolog of the functional fragment of soluble hTRAIL protein sequence beginning at amino acid position not lower than hTRAIL95 and ending at amino acid hTRAIL281, the sequence of which is at least in 70%, preferably in 85%, identical to original sequence.

In specific variants of this embodiment the domain (a) is a homolog of a fragment selected from the group consisting of sequences corresponding to hTRAIL95-281, hTRAIL114-281, hTRAIL116-281, hTRAIL120-281, hT I -281 and hTRAIL122-281.

It should be understood that a homolog of a hTRAIL fragment is a variation/modification of the amino acid sequence of this fragment, wherein at least one amino acid is changed, including 1 amino acid, 2 amino acids, 3 amino acids, 4 amino acids, 5 amino acids, 6 amino acids, and not more than 15% of amino acids, and wherein a fragment of the modified sequence has preserved functionality of the hTRAIL sequence, i.e. the ability of binding to cell surface death receptors and inducing apoptosis in mammalian cells. Modification of the amino acid sequence may include, for example, substitution, deletion, truncation and/or addition of amino acids.

Preferably, the homolog of hTRAIL fragment having modified sequence shows modified affinity to the death receptors DR4 (TRAIL-R1) or DR5 (TRAIL-R2) in comparison with the native fragment of hTRAIL.

The term "modified affinity" refers to increased affinity and/or affinity with altered receptor selectivity.

Preferably, the homolog of the fragment of hTRAIL having modified sequence shows increased affinity to the death receptors DR4 and DR5 compared to native fragment of hTRAIL.

Particularly preferably, the homolog of fragment of hTRAIL having modified sequence shows increased affinity to the death receptor DR5 in comparison with the death receptor DR4, i.e. an increased selectivity DR5/DR4.

Also preferably, the homolog of fragment of hTRAIL having modified sequence shows an increased selectivity towards the death receptors DR4 and/or DR5 in relation to the affinity towards the receptors DR1 (TRAIL-R3) and/or DR2 (TRAIL-R4).

Modifications of hTRAIL resulting in increased affinity and/or selectivity towards the death receptors DR4 and DR5 are known to those skilled in the art, for example from the publication Tur V, van der Sloot A M, Reis C R, Szegezdi E, Cool R H, Smali A, Serrano L, Quax W J. DR4-selective tumor necrosis factor-related apoptosis-inducing ligand (TRAIL) variants obtained by structure-based design. J. Biol. Chem. 2008 Jul. 18; 283(29):20560-8, which describes the D218H mutation having increased selectivity towards DR4, or Gasparian M E, Chernyak B V, Dolgikh D A, Yagolovich A V, Popova E N, Sycheva A M, Moshkovskii S A, Kirpichnikov M P. Generation of new TRAIL mutants DR5-A and DR5-B with improved selectivity to death receptor 5, Apoptosis. 2009 June; 14(6):778-87, which describes the D269H mutation having a reduced affinity towards DR4. hTRAIL mutants resulting in increased affinity towards one receptor selected from the DR4 and DR5 comparing with DR1 and DR2 receptors and increased affinity towards the receptor DR5 comparing with DR4 are also described in WO2009077857 and WO2009066174.

Suitable mutations are one or more mutations in the positions of native hTRAL selected from the group consisting of 131, 149, 159, 193, 199, 201, 204, 204, 212, 215, 218 and 251, in particular, mutations involving the substitution of an amino acid with a basic amino acid such as lysine, histidine or arginine, or amino acid such as glutamic acid or aspargic acid. Particularly one or more mutations selected from the group consisting of G131R, G131K, R1491, R149M, R149N, R149K, S159R, Q193H, Q193K, N199H, N199R, K201H, K201R, K204E, K204D, K204L, K204Y, K212R, S215E, S215H, S215K, S215D, D218Y, D218H, K251D, K251E and K251Q as described in WO2009066174, may be specified.

Suitable mutations are also one or more mutations in the positions of native hTRAL selected from the group consisting of 195, 269 and 214, particularly mutations involving the substitution of an amino acid with a basic amino acid such as lysine, histidine or arginine. Particularly one or more mutations selected from the group consisting of D269H, E195R, and T214R, as described in WO2009077857, may be specified.

In a particular embodiment, the domain (a) which is a homolog of the fragment of hTRAIL is selected from D218H mutant of the native TRAIL sequence, as described in WO2009066174, or the Y189N-R191K-Q193R-H264R-I266R-D269H mutant of the native TRAIL sequence, as described in Gasparian M E, Chernyak B V, Dolgikh D A, Yagolovich A V, Popova E N, Sycheva A M, Moshkovskii S A, Kirpichnikov M P., Apoptosis. 2009 June; 14(6):778-87.

The immunostimulating effector peptide of domain (b) may be a cytokine peptide which among others intensely stimulates human monocytes to produce TRAIL protein, thus significantly affecting the ability to eliminate cancer cells.

In one embodiment of the fusion protein of the invention, the effector peptide is a peptide having immunostimulating activity selected from the group consisting of SEQ. No. 17 (derived from INF alpha 2b), SEQ. No. 18 (derived from INF gamma), SEQ. No. 19 (a pseudodimer of INF gamma), SEQ. No. 46 (a pseudodimer of interferon alpha 2b) and SEQ. No. 47 (the consensus sequence of interferon alpha).

The effector peptide of the above group is the peptide that stimulates TRAIL overexpression, and specifically the 165-amino acid fragment of interferon alpha—subunit beta presented by SEQ. No. 17.

It is believed that the peptide comprising sequence of interferon alpha beta subunit incorporated into the fusion protein of the invention will effectively eliminate cancer cells.

Another effector peptide is a 124-aminoacid fragment of interferon gamma presented by SEQ. No. 18.

It is believed that the peptide comprising sequence of interferon gamma incorporated into the fusion protein of the invention will effectively eliminate cancer cells.

The effector peptide of the above group is a 263-aminoacid peptide constituting a fusion of two human interferon gamma subunits, forming single-chain pseudodimer of INF gamma, described by Landar'a et al. (J. Mol. Biol. 299: 169-179, 2000). The resulting single-chain protein variant retains the ability to bind to the suitable receptor and biological activity expected for interferon-gamma. This effector peptide is presented by SEQ. No. 19.

Another effector peptide of the above group is a 351-aminoacid peptide, a fusion of two human interferon alpha 2b subunits forming single-chain pseudodimer of INF alpha 2b wherein the second chain of IFN alpha 2b subunit sequence is reversed comparing to the native sequence (i.e. from C-terminus to N-terminus). The resulting effector peptide is characterized by two "native" C-terminal ends of interferon alpha 2b bound to each other. Monomers in naturally forming IFN alpha dimers are linked by their C-terminal ends. N-terminal ends, in turn, are responsible for interaction with the receptor and provide a proper environment for co-ordination of the process of dimerization of the zinc ion (glutamic acid residues 41 and 42). The resulting single-chain protein variant retains the ability to bind to the suitable receptor and biological activity expected for interferon-alpha. This effector peptide is presented by the SEQ. No. 46.

Another effector peptide is a 166-amino acid consensus sequence of interferon alpha presented by SEQ. No. 47. This consensus sequence is disclosed in U.S. Pat. No. 4,695,623.

It is believed that the peptide comprising the consensus sequence of interferon alpha incorporated into the fusion protein of the invention will effectively eliminate cancer cells.

Upon binding to TRAIL receptors present on the surface of cancer cells, the fusion protein will exert a double effect. Domain (a), that is a functional fragment of TRAIL or its homolog with preserved functionality, will exert its known agonistic activity—i.e. binding to death receptors on the cell surface and activation of the extrinsic pathway of apoptosis. After internalization of the fusion protein comprising immunostimulating peptide, the domain (b) will be able to potentially exert its action intracellularly in parallel to the activity of TRAIL domain. In this way, anti-cancer activity of TRAIL can be potentiated by activation of other elements and mechanisms such as stimulation of B cells to produce antibodies, stimulation of caspase 7 and 8 expression, or stimulation of overexpression of TRAIL.

In one of the embodiments of the invention, domain (a) and domain (b) are linked by at least one domain (c) comprising the sequence of a protease cleavage site recognized by proteases present in the cell environment, especially in the tumor cell environment. The linkage of the domain (a) with the domain (b) by at least one domain (c) means that between domains (a) and (b) more than one domain (c) may be present, in particular one or two domains (c).

A protease cleavage site can be selected from:
  a sequence recognized by metalloprotease MMP, in particular Pro Leu Gly Leu Ala Gly (PLGLAG in one-letter convention) designated as SEQ. No. 20,
  a sequence recognized by urokinase uPA, in particular Arg Val Val Arg (RVVR in one-letter convention) designated as SEQ.No. 21, and their combinations.

In one of the embodiments of the invention, the protease cleavage site is a combination of the sequence recognized by metalloprotease MMP and the sequence recognized by urokinase uPA, located next to each other in any order.

In one embodiment, the domain (c) is a combination of MMP/uPA (SEQ. No 20/Sekw. No. 21), that is the sequence Pro Leu Gly Leu Ala Gly Arg Val Val Arg (PLGLAGRVVR in one letter convention), or a combination of uPA/MMP (SEQ. No 21/SEQ. No. 20), that is the sequence Arg Val Val Arg Pro Leu Gly Leu Ala Gly (RVVRPLGLAG in one letter convention). Such combinations may be repeated, preferably twice.

Proteases metalloprotease MMP and urokinase uPA are overexpressed in the tumor environment. The presence of the sequence recognized by the proteases enables cleavage of the domain (a) from the domain (b) upon internalization of the construct, i.e. the release of the functional domain (b) and thus its activation.

The presence of the protease cleavage site, by allowing quick release of the effector peptide, increases the chances of transporting the peptide to the place of its action before random degradation of the fusion protein by proteases present in the cell occurs.

In another embodiment, between the domains (a) and (b) there is additionally incorporated domain (d) of a sequence suitable for attachment of a PEG molecule (PEG linker) to the fusion protein of the invention.

Such a PEG linker is for example a known sequence Ala Ser Gly Cys Gly Pro Glu (ASGCGPE in a one-letter convention), designated as the SEQ. No. 22. PEG linker can be also chosen from among Ala Ala Cys Ala Ala (AACAA in a one-letter convention), Ser Gly Gly Cys Gly Gly Ser (SGGCGGS in a one-letter convention) and Ser Sly Cys Sly Ser (SGCGS in a one-letter convention), designated as, respectively, SEQ. No. 23, SEQ. No. 24 and SEQ. No. 25.

In one of the embodiments, the protein of the invention comprises both domain (c) and domain (d).

In a preferred embodiment, domain (d) is located between two domains (c), in particular between two domains (c), which are selected from the protease cleavage site and a combination of protease cleavage sites, in particular, the sequence recognized by metalloproteases MMP (SEQ. No. 20), the sequence recognized by urokinase uPA (SEQ. No. 21), and the combination MMP/uPA (SEQ. No. 20/SEQ. No. 21) or uPA/MMP (SEQ. No. 21/SEQ. No. 20).

Thus, in one embodiment of the fusion protein of the invention, the protease cleavage site is a combination of the sequence recognized by metalloprotease MMP and the sequence recognized by urokinase uPA, in any order, separated by the PEG linker sequence discussed above.

It should be understood that in the case when the fusion protein has both the domain (d) of the PEG linker and the domains (c) of the cleavage site between the domains (a) and (b), then the domains (c) are located in such a way that after cleavage of the construct the domain (d) is disconnected from the domains (a) and (b). These two domains (c) may contain both single protease cleavage site and combinations thereof, as defined above. In other words, if the fusion protein contains both domain (d) comprising PEG linker and cleavage site domains (c), then domain (d) is located between domains (c). The invention does not comprise such a variant in which domain (d) would be located between domain (c) and domain (a) or between domain (c) and domain (b), that is the variant wherein after cleavage of the construct the sequence suitable for attachment to the fusion protein of the invention of a PEG molecule (d) would remain attached to domain (a) or domain (b).

PEG molecules useful for attachment to the fusion protein may be selected from linear and branched PEG molecules. Particularly useful are linear PEG molecule having a molecular weight between 4000 and 20000.

Apart from the main functional elements of the fusion protein, the cleavage site domain(s) and the PEG linker sequence, the fusion proteins of the invention may contain a neutral sequence/sequences of a flexible steric glycine-serine linker (spacer). Such linkers/spacers are well known and described in the literature. Their incorporation into the sequence of the fusion protein is intended to provide the correct folding of proteins produced by the process of its overexpression in the host cells.

Flexible steric linker may be selected from any combination of glycine and serine residues. In particular, flexible linker may be selected from the group consisting of Gly Ser Gly Gly Gly (GSGGG in one letter convention), Gly Gly Gly Ser (GGGS in one letter convention), Xaa Gly Gly Ser (XGGS in one letter convention) wherein Xaa designates any aminoacid or is absent, and Gly Gly Ser Gly (GGSG in one letter convention) designated as, respectively SEQ. No. 26, SEQ. No. 27 and SEQ. No. 28) and SEQ. No. 50.

Particular embodiments of the fusion protein of the invention are fusion proteins comprising an immunostimulating peptide selected from the group consisting of the proteins represented by SEQ. No. 1, SEQ. No. 2, SEQ. No. 3, SEQ. No. 4, and SEQ. No. 45.

Other specific embodiment of the fusion protein of the invention is fusion protein comprising an immunostimulating peptide represented by SEQ. No. 44.

Other specific embodiments of the fusion protein of the invention are fusion proteins comprising an immunostimulating peptide, selected from the group consisting of the proteins represented by SEQ. No. 5, SEQ. No. 6, SEQ. No. 7, SEQ. No. 8, SEQ. No. 9, SEQ. No. 10 and SEQ. No. 11.

Other specific embodiments of the fusion protein of the invention are fusion proteins comprising an immunostimulating peptide, selected from the group consisting of the proteins represented by SEQ. No. 12, SEQ. No. 13, SEQ. No. 14 and SEQ. No. 15.

A detailed description of the structure of representative fusion proteins mentioned above are shown in FIGS. 1 to 3 and in FIG. 4, and in the Examples presented herein below.

In accordance with the present invention, "a fusion protein" means a single protein molecule containing two or more proteins or fragments thereof, covalently linked via peptide bond within their respective peptide chains, without additional chemical linkers.

The fusion protein can also be alternatively described as a protein construct or a chimeric protein. According to the present invention, the terms "construct" or "chimeric protein", if used, should be understood as referring to the fusion protein as defined above.

For a person skilled in the art it will be apparent that the fusion protein thus defined can be synthesized by known methods of chemical synthesis of peptides and proteins.

The fusion protein can be synthesized by methods of chemical peptide synthesis, especially using the techniques of peptide synthesis in solid phase using suitable resins as carriers. Such techniques are conventional and known in the art, and described inter alia in the monographs, such as for example Bodanszky and Bodanszky, The Practice of Peptide Synthesis, 1984, Springer-Verlag, New York, Stewart et al., Solid Phase Peptide Synthesis, 2nd Edition, 1984, Pierce Chemical Company.

The fusion protein can be synthesized by the methods of chemical synthesis of peptides as a continuous protein. Alternatively, the individual fragments (domains) of protein may be synthesized separately and then combined together in one continuous peptide via a peptide bond, by condensation of the amino terminus of one peptide fragment from the carboxyl terminus of the second peptide. Such techniques are conventional and well known.

For verification of the structure of the resulting peptide known methods of the analysis of amino acid composition of peptides may be used, such as high resolution mass spectrometry technique to determine the molecular weight of the peptide. To confirm the peptide sequence protein sequencers can also be used, which sequentially degrade the peptide and identify the sequence of amino acids.

Preferably, however, the fusion protein of the invention is a recombinant protein, generated by methods of gene expression of a polynucleotide sequence encoding the fusion protein in host cells.

A further aspect of the invention is the polynucleotide sequence, particularly DNA sequence encoding a fusion protein as defined above.

Preferably, the polynucleotide sequence, particularly DNA, according to the invention, encoding the fusion protein as defined above, is a sequence optimized for expression in *E. coli*.

Another aspect of the invention is also an expression vector containing the polynucleotide sequence, particularly DNA sequence of the invention as defined above.

Another aspect of the invention is also a host cell comprising an expression vector as defined above.

A preferred host cell for expression of fusion proteins of the invention is an *E. coli* cell.

Methods for generation of recombinant proteins, including fusion proteins, are well known. In brief, this technique consists in generation of polynucleotide molecule, for example DNA molecule encoding the amino acid sequence of the target protein and directing the expression of the target protein in the host. Then, the target protein encoding polynucleotide molecule is incorporated into an appropriate expression vector, which ensures an efficient expression of the polypeptide. Recombinant expression vector is then introduced into host cells for transfection/transformation, and as a result a transformed host cell is produced. This is followed by a culture of transformed cells to overexpress the target protein, purification of obtained proteins, and optionally cutting off by cleavage the tag sequences used for expression or purification of the protein.

Suitable techniques of expression and purification are described, for example in the monograph Goeddel, Gene Expression Technology, Methods in Enzymology 185, Academic Press, San Diego, Calif. (1990), and A. Staron et al., Advances Mikrobiol., 2008, 47, 2, 1983-1995.

Cosmids, plasmids or modified viruses can be used as expression vectors for the introduction and replication of DNA sequences in host cells. Typically plasmids are used as expression vectors. Suitable plasmids are well known and commercially available.

Expression vector of the invention comprises a polynucleotide molecule encoding the fusion protein of the invention and the necessary regulatory sequences for transcription and translation of the coding sequence incorporated into a suitable host cell. Selection of regulatory sequences is dependent on the type of host cells and can be easily carried out by a person skilled in the art. Examples of such regulatory sequences are transcriptional promoter and enhancer or RNA polymerase binding sequence, ribosome binding sequence, containing the transcription initiation signal, inserted before the coding sequence, and transcription terminator sequence, inserted after the coding sequence. Moreover, depending on the host cell and the vector used, other sequences may be introduced into the expression vector, such as the origin of replication, additional DNA restriction sites, enhancers, and sequences allowing induction of transcription.

The expression vector will also comprise a marker gene sequence, which confers defined phenotype to the transformed cell and enables specific selection of transformed cells. Furthermore, the vector may also contain a second marker sequence which allows to distinguish cells transformed with recombinant plasmid containing inserted coding sequence of the target protein from those which have taken up the plasmid without insert. Most often, typical antibiotic resistance markers are used, however, any other reporter genes known in the field may be used, whose presence in a cell (in vivo) can be easily determined using autoradiography techniques, spectrophotometry or bio- and chemiluminescence. For example, depending on the host cell, reporter genes such as β-galactosidase, β-gluckuronidase, luciferase, chloramphenicol acetyltransferase or green fluorescent protein may be used.

Furthermore, the expression vector may contain signal sequence, transporting proteins to the appropriate cellular compartment, e.g. periplasma, where folding is facilitated.

Additionally a sequence encoding a label/tag, such as HisTag attached to the N-terminus or GST attached to the C-terminus, may be present, which facilitates subsequent purification of the protein produced using the principle of affinity, via affinity chromatography on a nickel column. Additional sequences that protect the protein against proteolytic degradation in the host cells, as well as sequences that increase its solubility may also be present.

Auxiliary element attached to the sequence of the target protein may block its activity, or be detrimental for another reason, such as for example due to toxicity. Such element must be removed, which may be accomplished by enzymatic or chemical cleavage. In particular, a six-histidine tag HisTag or other markers of this type attached to allow protein purification by affinity chromatography should be removed, because of its described effect on the liver toxicity of soluble TRAIL protein. Heterologous expression systems based on various well-known host cells may be used, including prokaryotic cells: bacterial, such as *Escherichia coli* or *Bacillus subtilis*, yeasts such as *Saccharomyces cervisiae* or *Pichia pastoris*, and eukaryotic cell lines (insect, mammalian, plant).

Preferably, due to the ease of culturing and genetic manipulation, and a large amount of obtained product, the *E. coli* expression system is used. Accordingly, the polynucleotide sequence containing the target sequence encoding the fusion protein of the invention will be optimized for expression in *E. coli*, i.e. it will contain in the coding sequence codons optimal for expression in *E. coli*, selected from the possible sequence variants known in the state of art. Furthermore, the expression vector will contain the above described elements suitable for *E. coli* attached to the coding sequence.

Accordingly, in a preferred embodiment of the invention a polynucleotide sequence comprising a sequence encoding a fusion protein of the invention, optimized for expression in *E. coli* is selected from the group of polynucleotide sequences consisting of:

SEQ. No. 29 SEQ. No. 30; SEQ. No. 31; SEQ. No. 32; SEQ. No. 33; SEQ. No. 34; SEQ. No. 35; SEQ. No. 36; SEQ. No. 37; SEQ. No. 38; SEQ. No. 39; SEQ. No. 40; SEQ. No. 41, SEQ. No. 42, SEQ. No. 43, SEQ. No. 48 and SEQ. No. 49, which encode a fusion protein having an amino acid sequence corresponding to amino acid sequences selected from the group consisting of amino acid sequences, respectively:

SEQ. No. 1; SEQ. No. 2; SEQ. No. 3; SEQ. No. 4; SEQ. No. 5; SEQ. No. 6; SEQ. No. 7; SEQ. No. 8; SEQ. No. 9; SEQ. No. 10; SEQ. No. 11; SEQ. No. 12; SEQ. No. 13; SEQ. No. 14 and SEQ. No. 15., SEQ. No. 44 and SEQ. No. 45. In a preferred embodiment, the invention provides also an expression vector suitable for transformation of *E. coli*, comprising the polynucleotide sequence selected from the group of polynucleotide sequences SEQ. No. 29 to SEQ. No. 43, SEQ. No. 48 and SEQ. No. 49 indicated above, as well as *E. coli* cell transformed with such an expression vector.

Transformation, i.e. introduction of a DNA sequence into bacterial host cells, particularly *E. coli*, is usually performed on the competent cells, prepared to take up the DNA for example by treatment with calcium ions at low temperature (4° C.), and then subjecting to the heat-shock (at 37-42° C.) or by electroporation.

Such techniques are well known and are usually determined by the manufacturer of the expression system or are described in the literature and manuals for laboratory work, such as Maniatis et al., Molecular Cloning. Cold Spring Harbor, N.Y., 1982).

The procedure of overexpression of fusion proteins of the invention in *E. coli* expression system will be further described below.

The invention also provides a pharmaceutical composition containing the fusion protein of the invention as defined above as an active ingredient and a suitable pharmaceutically acceptable carrier, diluent and conventional auxiliary components. The pharmaceutical composition will contain an effective amount of the fusion protein of the invention and pharmaceutically acceptable auxiliary components dissolved or dispersed in a carrier or diluent, and preferably will be in the form of a pharmaceutical composition formulated in a unit dosage form or formulation containing a plurality of doses. Pharmaceutical forms and methods of their formulation as well as other components, carriers and diluents are known to the skilled person and described in the literature. For example, they are described in the monograph Remington's Pharmaceutical Sciences, ed. 20, 2000, Mack Publishing Company, Easton, USA.

The terms "pharmaceutically acceptable carrier, diluent, and auxiliary ingredient" comprise any solvents, dispersion media, surfactants, antioxidants, stabilizers, preservatives (e.g. antibacterial agents, antifungal agents), isotonicity agents, known in the art. The pharmaceutical composition of the invention may contain various types of carriers, diluents and excipients, depending on the chosen route of administration and desired dosage form, such as liquid, solid and aerosol forms for oral, parenteral, inhaled, topical, and whether that selected form must be sterile for administration route such as by injection. The preferred route of administration of the pharmaceutical composition according to the invention is parenteral, including injection routes such as intravenous, intramuscular, subcutaneous, intraperitoneal, intratumor, or by single or continuous intravenous infusions.

In one embodiment, the pharmaceutical composition of the invention may be administered by injection directly to the tumor. In another embodiment, the pharmaceutical composition of the invention may be administered intravenously.

In yet another embodiment, the pharmaceutical composition of the invention can be administered subcutaneously or intraperitoneally. A pharmaceutical composition for parenteral administration may be a solution or dispersion in a pharmaceutically acceptable aqueous or non-aqueous medium, buffered to an appropriate pH and isoosmotic with body fluids, if necessary, and may also contain antioxidants, buffers, bacteriostatic agents and soluble substances, which make the composition compatible with the tissues or blood of recipient. Other components, which may included in the composition, are for example water, alcohols such as ethanol, polyols such as glycerol, propylene glycol, liquid polyethylene glycol, lipids such as triglycerides, vegetable oils, liposomes. Proper fluidity and the particles size of the substance may be provided by coating substances, such as lecithin, and surfactants, such as hydroxypropyl-celulose polysorbates, and the like.

Suitable isotonicity agents for liquid parenteral compositions are, for example, sugars such as glucose, and sodium chloride, and combinations thereof.

Alternatively, the pharmaceutical composition for administration by injection or infusion may be in a powder form, such as a lyophilized powder for reconstitution immediately prior to use in a suitable carrier such as, for example, sterile pyrogen-free water.

The pharmaceutical composition of the invention for parenteral administration may also have the form of nasal administration, including solutions, sprays or aerosols. Preferably, the form for intranasal administration will be an aqueous solution and will be isotonic or buffered o maintain the pH from about 5.5 to about 6.5, so as to maintain a character similar to nasal secretions. Moreover, it will contain preservatives or stabilizers, such as in the well-known intranasal preparations.

The composition may contain various antioxidants which delay oxidation of one or more components. Furthermore, in order to prevent the action of micro-organisms, the composition may contain various antibacterial and anti fungal agents, including, for example, and not limited to, parabens, chlorobutanol, thimerosal, sorbic acid, and similar known substances of this type. In general, the pharmaceutical composition of the invention can include, for example at least about 0.01 wt % of active ingredient. More particularly, the composition may contain the active ingredient in the amount from 1% to 75% by weight of the composition unit, or for example from 25% to 60% by weight, but not limited to the indicated values. The actual amount of the dose of the composition according to the present invention administered to patients, including man, will be determined by physical and physiological factors, such as body weight, severity of the condition, type of disease being treated, previous or concomitant therapeutic interventions, the patient and the route of administration. A suitable unit dose, the total dose and the concentration of active ingredient in the composition is to be determined by the treating physician.

The composition may for example be administered at a dose of about 1 microgram/kg of body weight to about 1000 mg/kg of body weight of the patient, for example in the range of 5 mg/kg of body weight to 100 mg/kg of body weight or in the range of 5 mg/kg of body weight to 500 mg/kg of body weight. The fusion protein and the compositions containing it exhibit anticancer or antitumor and can be used for the treatment of cancer diseases. The invention also provides the use of the fusion protein of the invention as defined above for treating cancer diseases in mammals, including humans. The invention also provides a method of treating cancer diseases in mammals, including humans, comprising administering to a subject in need of such treatment an anticancer effective amount of the fusion protein of the invention as defined above, optionally in the form of appropriate pharmaceutical composition.

The fusion protein of the invention can be used for the treatment of hematologic malignancies, such as leukemia, granulomatosis, myeloma and other hematologic malignancies. The fusion protein can also be used for the treatment of solid tumors, such as breast cancer, lung cancer, including non-small cell lung cancer, colon cancer, pancreatic cancer, ovarian cancer, bladder cancer, prostate cancer, kidney cancer, brain cancer, and the like. Appropriate route of administration of the fusion protein in the treatment of cancer wilt be in particular parenteral route, which consists in administering the fusion protein of the invention in the form of injections or infusions, in the composition and form appropriate for this administration route. The invention will be described in more detail in the following general procedures and examples of specific fusion proteins.

General Procedure for Overexpression of the Fusion Protein
Preparation of Plasmid Amino acid sequence of the target fusion protein was used as a template to generate a DNA sequence encoding it, comprising codons optimized for expression in *Escherichia coli*. Such a procedure allows to increase the efficiency of a further step of target protein synthesis in *Escherichia coli*. Resulting nucleotide sequence was then automatically synthesized. Additionally, the cleavage sites of restriction enzymes NdeI (at the 5'-end of leading strand) and XhoI (at the 3'end of leading strand) were added to the resulting gene encoding the target protein. These were used to clone the gene into the vector pET28a (Novagen). They may be also be used for cloning the gene encoding the protein to other vectors. Target protein expressed from this construct was equipped at the N-terminus with a polyhistidine tag (six histidines), preceded by a site recognized by thrombin, which subsequently served to its purification via affinity chromatography. The correctness of the resulting construct was confirmed firstly by restriction analysis of isolated plasmids using the enzymes NdeI and XhoI, followed by automatic sequencing of the entire reading frame of the target protein. The primers used for sequencing were complementary to the sequences of T7 promoter (5'-TAATACGACTCACTATAGG-3') (SEQ ID NO 51) and T7 terminator (5'GCTAGTTATTGCTCAGCGG-3') (SEQ ID NO 52) present in the vector. Resulting plasmid was used for overexpression of the target fusion protein in a commercial *E. coli* strain, which was transformed according to the manufacturer's recommendations. Colonies obtained on the selection medium (LB agar, kanamycin 50 µg/ml, 1% glucose) were used for preparing an overnight culture in LB liquid medium supplemented with kanamycin (50 µg/ml) and 1% glucose. After about 15 h of growth in shaking incubator, the cultures were used to inoculate the appropriate culture.

Overexpression and Purification of Fusion Proteins—General Procedure A

LB medium with kanamycin (30 µg/ml) and 100 µM zinc sulfate was inoculated with overnight culture. The culture was incubated at 37° C. until the optical density (OD) at 600 nm reached 0.60-0.80. Then IPTG was added to the final concentration in the range of 0.25-1 mM. After incubation (3.5-20 h) with shaking at 25° C. the culture was centrifuged for 25 min at 6,000 g. Bacterial pellets were resuspended in a buffer containing 50 mM $KH_2PO_4$, 0.5 M NaCl, 10 mM imidazole, pH 7.4. The suspension was sonicated on ice for 8 minutes (40% amplitude, 15-second pulse, 10 s interval). The resulting extract was clarified by centrifuging for 40 minutes at 20000 g, 4° C. Ni-Sepharose (GE Healthcare) resin was pre-treated by equilibration with buffer, which was used for preparation of the bacterial cells extract. The resin was then incubated overnight at 4° C. with the supernatant obtained after centrifugation of the extract. Then it was loaded into chromatography column and washed with 15 to 50 volumes of buffer 50 mM $KH_2PO_4$, 0.5 M NaCl, 20 mM imidazole, pH 7.4. The obtained protein was eluted from the column using imidazole gradient in 50 mM $KH_2PO_4$ buffer with 0.5 M NaCl, pH 7.4. Obtained fractions were analyzed by SDS-PAGE. Appropriate fractions were combined and dialyzed overnight at 4° C. against 50 mM Tris buffer, pH 7.2, 150 mM NaCl, 500 mM L-arginine, 0.1 mM $ZnSO_4$, 0.01% Tween 20, and at the same time 10 Histag was cleaved with thrombin (1:50). After the cleavage, thrombin was separated from the target fusion protein using Benzamidine Sepharose™ resin. The purity of the product was analyzed by SDS-PAGE electrophoresis (Maniatis et al, Molecular Cloning. Cold Spring Harbor, N.Y., 1982).

Overexpression and Purification of Fusion Proteins—General Procedure B

LB medium with kanamycin (30 µg/ml) and 100 µM zinc sulfate was inoculated with overnight culture. Cultures were incubated at 37° C. until optical density (OD) at 600 nm reached 0.60-0.80. Then IPTG was added to the final concentration in the range 0.5-1 mM. After 20 h incubation with shaking at 25° C. the culture was centrifuged for 25 min at 6000 g. Bacterial cells after overexpression were disrupted in a French Press in a buffer containing 50 mM $KH_2PO_4$, 0.5 M NaCl, 10 mM imidazole, 5 mM betamercaptoethanol, 0.5 mM PMSF (phenylmethyl-sulphonyl fluoride), pH 7.8. Resulting extract was clarified by centrifugation for 50 minutes at 8000 g. The obtained supernatant was incubated overnight with Ni-Sepharose resin. Then the resin with bound protein was packed into the chromatography column. To wash-out the fractions containing non-binding proteins, the column was washed with 15 to 50 volumes of buffer 50 mM KH$_2$PO$_4$, 0.5 M NaCl, 10 mM imidazole, 5 mM beta-mercaptoethanol, 0.5 mM PMSF (phenyl-methylsulphonyl fluoride), pH 7.8. Then, to wash-out the majority of proteins binding specifically with the bed, the column was washed with a buffer containing 50 mM KH2PO4, 0.5 M NaCl, 500 mM imidazole, 10% glycerol, 0.5 mM PMSF, pH 7.5. Obtained fractions were analyzed by SDS-PAGE (Maniatis et al, Molecular Cloning. Cold Spring Harbor, N.Y., 1982). The fractions containing the target protein were combined and cleaved with thrombin (1 U per 4 mg of protein, 8 h at 16° C.) to remove polyhistidine tag. Then the fractions were dialyzed against formulation buffer (500 mM L-arginine, 50 mM Tris, 2.5 mM ZnSO$_4$, pH 7.4).

EXAMPLE 1

The Fusion Protein of SEQ. No. 1

The protein of SEQ. No. 1 is a fusion protein having the length of 345 amino acids and the mass of 39.8 kDa, in which at the N-terminus of the sequence TRAIL122-281 a 165-amino acid subunit 2b of human interferon alpha (SEQ. No. 17) is attached as an effector peptide. Between the effector peptide and the sequence of TRAIL there are incorporated sequentially next to each other sequences of protease cleavage sites recognized by metalloprotease MMP (SEQ. No. 20) and urokinase uPA (SEQ. No. 21) due to which the effector peptide will undergo cleavage in the tumour environment upon internalization of the fusion protein.

Structure of the fusion protein is shown schematically in FIG. 1 and its amino acid sequence and the DNA encoding sequence comprising codons optimized for expression in *E. coli* are, respectively, SEQ. No. 1 and SEQ. No. 29 as shown in the attached Sequence Listing.

The amino acid sequence SEQ. No. 1 of the structure described above was used as a template to generate its coding DNA sequence SEQ. No. 29. A plasmid containing the coding sequence of DNA was generated and overexpression of the fusion protein was carried out in accordance with the general procedures described above. Overexpression was performed according to the general procedure A, using *E. coli* BL21 (DE3) and Tuner(DE3)pLysS strains from Novagen. The protein was separated by electrophoresis in accordance with the general procedure described above.

EXAMPLE 2

The Fusion Protein of SEQ. No. 2

The protein of SEQ. No. 2 is a fusion protein having the length of 347 amino acids and the mass of 40 kDa, in which at the C-terminus of the sequence TRAIL120-281 a 165-amino acid subunit 2b of human interferon alpha (SEQ. No. 17) is attached as an effector peptide. Between the effector peptide and the sequence of TRAIL there are incorporated sequentially next to each other sequences of protease cleavage sites recognized by metalloprotease MMP (SEQ. No. 20) and urokinase uPA (SEQ. No. 21) due to which the effector peptide will undergo cleavage in the tumor environment upon internalization of the fusion protein.

Structure of the fusion protein is shown schematically in FIG. 1 and its amino acid sequence and the DNA encoding sequence comprising codons optimized for expression in *E. coli* are, respectively, SEQ. No. 2 and SEQ. No. 30 as shown in the attached Sequence Listing.

The amino acid sequence SEQ. No. 2 of the structure described above was used as a template to generate its coding DNA sequence SEQ. No. 30. A plasmid containing the coding sequence of DNA was generated and overexpression of the fusion protein was carried out in accordance with the general procedures described above. Overexpression was performed according to the general procedure A, using *E. coli* BL21 (DE3) strain from Novagen. The protein was separated by electrophoresis in accordance with the general procedure described above.

EXAMPLE 3

The Fusion Protein of SEQ. No. 3

The protein of SEQ. No. 3 is a fusion protein having the length of 352 amino acids and the mass of 40.4 kDa, in which at the N-terminus of the sequence TRAIL122-281 a 165-amino acid subunit 2b of human interferon alpha (SEQ. No. 17) is attached as an effector peptide. Between the effector peptide and the sequence of TRAIL there are incorporated two combinations of sequences of protease cleavage sites recognized by metalloprotease MMP (SEQ. No. 20) and urokinase uPA (SEQ. No. 21) due to which the effector peptide will undergo cleavage in the tumour environment upon internalization of the fusion protein. Between these two combinations of SEQ. No. 20 and SEQ. No. 21 the fusion protein incorporates additionally linker for pegylation (SEQ. No. 22).

Structure of the fusion protein is shown schematically in FIG. 1 and its amino acid sequence and the DNA encoding sequence comprising codons optimized for expression in *E. coli* are, respectively, SEQ. No. 3 and SEQ. No. 31 as shown in the attached Sequence Listing.

The amino acid sequence SEQ. No. 3 presented above was used as a template to generate its coding DNA sequence SEQ. No 31 presented above. A plasmid containing the coding sequence of DNA was generated and overexpression of the fusion protein was carried out in accordance with the general procedures described above. Overexpression was performed according to the general procedure B, using *E.coli* strain BL21 (DE3) from Novagen. The protein was separated by electrophoresis in accordance with the general procedure described above.

EXAMPLE 4

The Fusion Protein of SEQ. No. 4

The protein of SEQ. No. 4 is a fusion protein having the length of 353 amino acids and the mass of 40.5 kDa, in which at the C-terminus of the sequence TRAIL121-281 a 165-amino acid subunit 2b of human interferon alpha (SEQ. No. 17) is attached as an effector peptide. Between the effector peptide and the sequence of TRAIL there are incorporated two combinations of sequences of protease cleavage sites recognized by metalloprotease MMP (SEQ. No. 20) and urokinase uPA (SEQ. No. 21) due to which the effector peptide will undergo cleavage in the tumour environment upon internalization of the fusion protein. Between these two combinations of SEQ. No. 20 and SEQ. No. 21 the fusion protein incorporates additionally the linker for pegylation (SEQ. No. 22).

Structure of the fusion protein is shown schematically in FIG. 1 and its amino acid sequence and the DNA encoding sequence comprising codons optimized for expression in *E. coli* are, respectively, SEQ. No. 4 and SEQ. No. 32 as shown in the attached Sequence Listing.

The amino acid sequence SEQ. No. 4 presented above was used as a template to generate its coding DNA sequence SEQ. No 32 presented above. A plasmid containing the coding sequence of DNA was generated and overexpression of the fusion protein was carried out in accordance with the general procedures described above. Overexpression was performed according to the general procedure B, using *E. coli* BL21DE3pLysSRIL strain from Stratagene and *E. coli* Tuner (DE3) z from Novagen. The protein was separated by electrophoresis in accordance with the general procedure described above.

EXAMPLE 5

The Fusion Protein of SEQ. No. 5

The protein of SEQ. No. 5 is a fusion protein having the length of 300 amino acids and the mass of 34.7 kDa, in which at the N-terminus of the sequence TRAIL116-281 a fragment of human interferon gamma (SEQ. No. 18) is attached as an effector peptide. Between the effector peptide and the sequence of TRAIL the protein contains sequences of protease cleavage sites recognized by metalloprotease MMP (SEQ. No. 20) and urokinase uPA (SEQ. No. 21).

Figure 2:
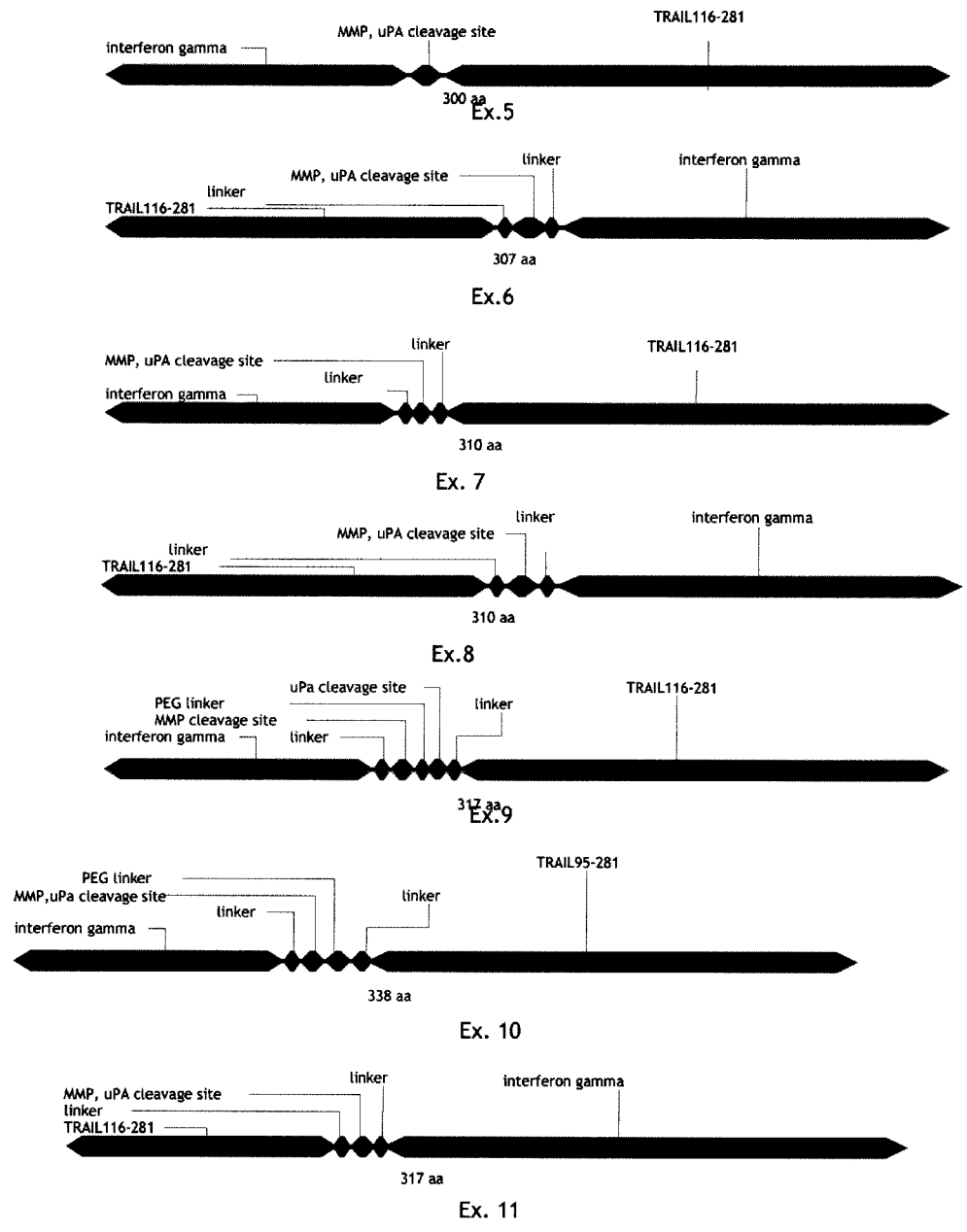
FIG. 2 presents schematic structures of fusion proteins of the invention according to Ex. 5, Ex. 6, Ex. 7, Ex. 8, Ex. 9, Ex. 10 and Ex. 11.

Structure of the fusion protein is shown schematically in FIG. 2 and its amino acid sequence and the DNA encoding sequence comprising codons optimized for expression in *E. coli* are, respectively, SEQ. No. 5 and SEQ. No. 33 as shown in the attached Sequence Listing.

The amino acid sequence SEQ. No. 5 of the structure described above was used as a template to generate its coding DNA sequence SEQ. No. 33. A plasmid containing the coding sequence of DNA was generated and overexpression of the fusion protein was carried out in accordance with the general procedures described above. Overexpression was performed according to the general procedure A, using *E. coli* Tuner (DEV strain from Novagen. The protein was separated by electrophoresis in accordance with the general procedure described above.

EXAMPLE 6

The Fusion Protein of SEQ. No. 6

The protein of SEQ. No. 6 is a fusion protein having the length of 307 amino acids and the mass of 35.1 kDa, in which at the C-terminus of the sequence TRAIL116-281 a fragment of human interferon gamma (SEQ. No. 18) is attached as an effector peptide. Between the effector peptide and the sequence of TRAIL the protein contains sequences of protease cleavage sites recognized by metalloprotease MMP (SEQ. No. 20) and urokinase uPA (SEQ. No. 21).

The protein comprises also flexible linkers: flexible glycine-serine linker (SEQ. No. 27) between the sequence of TRAIL and metalloprotease MMP cleavage site; and flexible glycine-serine linker (SEQ. No. 28) between the urokinase uPa cleavage site and the effector sequence.

Structure of the fusion protein is shown schematically in FIG. 2 and its amino acid sequence and the DNA encoding sequence comprising codons optimized for expression in *E. coli* are, respectively, SEQ. No. 6 and SEQ. No. 34 as shown in the attached Sequence Listing.

The amino acid sequence SEQ. No. 6 of the structure described above was used as a template to generate its coding DNA sequence SEQ. No. 34. A plasmid containing the coding sequence of DNA was generated and overexpression of the fusion protein was carried out in accordance with the general procedures described above. Overexpression was performed according to the general procedure A, using *E. coli* Tuner(DE3) strain from Novagen. The protein was separated by electrophoresis in accordance with the general procedure described above.

EXAMPLE 7

The Fusion Protein of SEQ. No. 7

The protein of SEQ. No. 7 is a fusion protein having the length of 310 amino acids and the mass of 35.5 kDa, in which at the N-terminus of the sequence TRAIL116-281 a fragment of human interferon gamma (SEQ. No. 18) is attached as an effector peptide. Between the effector peptide and the sequence of TRAIL the protein contains sequences of protease cleavage sites recognized by metalloprotease MMP (SEQ. No. 20) and urokinase uPA (SEQ. No. 21).

The protein comprises also flexible linkers: flexible glycine-serine linker of SEQ. No. 26 between the sequence of effector peptide and metalloprotease MMP cleavage site; and flexible glycine-serine linker SEQ. No. 26 between the urokinase uPa cleavage site and TRAIL sequence.

Structure of the fusion protein is shown schematically in FIG. 2 and its amino acid sequence and the DNA encoding sequence comprising codons optimized for expression in *E. coli* are, respectively, SEQ. No. 7 and SEQ. No. 35 as shown in the attached Sequence Listing.

The amino acid sequence SEQ. No. 7 of the structure described above was used as a template to generate its coding DNA sequence SEQ. No. 35. A plasmid containing the coding sequence of DNA was generated and overexpression of the fusion protein was carried out in accordance with the general procedures described above. Overexpression was performed according to the general procedure A, using *E. coli* Tuner(DE3) strain from Novagen. The protein was separated by electrophoresis in accordance with the general procedure described above.

EXAMPLE 8

The Fusion Protein of SEQ. No. 8

The protein of SEQ. No. 8 is a fusion protein having the length of 310 amino acids and the mass of 35.3 kDa, in which at the C-terminus of the sequence TRAIL116-281 a fragment of human interferon gamma (SEQ. No. 18) is attached as an effector peptide. Between the effector peptide and the sequence of TRAIL the protein contains sequences of protease cleavage sites recognized by metalloprotease MMP (SEQ. No. 20) and urokinase uPA (SEQ. No. 21).

The protein comprises also flexible linkers: flexible glycine-serine linker GSGGG (SEQ. No. 26) between the sequence of effector peptide and metalloprotease MMP cleavage site; and flexible glycine-serine linker GSGGG (SEQ. No. 26) between the urokinase uPa cleavage site and TRAIL sequence.

Structure of the fusion protein is shown schematically in FIG. 2 and its amino acid sequence and the DNA encoding sequence comprising codons optimized for expression in *E. coli* are, respectively, SEQ. No. 8 and SEQ. No. 36 as shown in the attached Sequence Listing.

The amino acid sequence SEQ. No. 8 of the structure described above was used as a template to generate its coding DNA sequence SEQ. No. 36. A plasmid containing the coding sequence of DNA was generated and overexpression of the fusion protein was carried out in accordance with the general procedures described above. Overexpression was performed according to the general procedure A, using *E. coli* Tuner(DE3) strain from Novagen. The protein was separated by electrophoresis in accordance with the general procedure described above

EXAMPLE 9

The Fusion Protein of SEQ. No. 9

The protein of SEQ. No. 9 is a fusion protein having the length of 317 amino acids and the mass of 35.9 kDa, in which at the N-terminus of the sequence TRAIL116-281 a fragment of human interferon gamma (SEQ. No. 18) is attached as an effector peptide. Between the effector peptide and the sequence of TRAIL there is incorporated the combination of protease cleavage sites recognized by metalloprotease MMP (SEQ. No. 20) and urokinase uPA (SEQ. No. 21) due to which the effector peptide will undergo cleavage in the tumour environment upon internalization of the fusion protein. Between the SEQ. No. 20 and SEQ. No. 21 the fusion protein contains additionally the linker for pegylation (SEQ. No. 22).

The protein comprises also flexible linkers: flexible glycine-serine linker GSGGG (SEQ. No. 26) between the sequence of effector peptide and metalloprotease MMP cleavage site; and flexible glycine-serine linker GSGGG (SEQ. No. 26) between the urokinase uPa cleavage site and TRAIL sequence.

Structure of the fusion protein is shown schematically in FIG. 2 and its amino acid sequence and the DNA encoding sequence comprising codons optimized for expression in *E. coli* are, respectively, SEQ. No. 9 and SEQ. No. 37 as shown in the attached Sequence Listing.

The amino acid sequence SEQ. No. 9 of the structure described above was used as a template to generate its coding DNA sequence SEQ. No. 37. A plasmid containing the coding sequence of DNA was generated and overexpression of the fusion protein was carried out in accordance with the general procedures described above. Overexpression was performed according to the general procedure A, using *E. coli* Rosetta (DE3) strain from Novagen. The protein was separated by electrophoresis in accordance with the general procedure described above.

EXAMPLE 10

The Fusion Protein of SEQ. No. 10

The protein of SEQ. No. 10 is a fusion protein having the length of 338 amino acids and the mass of 38.3 kDa, in which at the N-terminus of the sequence TRAIL95-281 a fragment of human interferon gamma (SEQ. No. 18) is attached as an effector peptide. Between the effector peptide and the sequence of TRAIL the fusion protein contains the sequences of protease cleavage sites recognized by metalloprotease MMP (SEQ. No. 20) and urokinase uPA (SEQ. No. 21) due to which the effector peptide will undergo cleavage in the tumor environment upon internalization of the fusion protein. Next to the SEQ. No. 21 the fusion protein contains additionally the linker for pegylation (SEQ. No. 22).

The protein comprises also flexible linkers: between the sequence of effector peptide and metalloprotease MMP cleavage site the flexible glycine-serine linker GSGGG (SEQ. No. 26); and between the linker for pegylation and TRAIL sequence the flexible glycine-serine linker GSGGG (SEQ. No. 26).

Structure of the fusion protein is shown schematically in FIG. 2 and its amino acid sequence and the DNA encoding sequence comprising codons optimized for expression in *E. coli* are, respectively, SEQ. No. 10 and SEQ. No. 38 as shown in the attached Sequence Listing.

The amino acid sequence SEQ. No. 10 of the structure described above was used as a template to generate its coding DNA sequence SEQ. No. 38. A plasmid containing the coding sequence of DNA was generated and overexpression of the fusion protein was carried out in accordance with the general procedures described above. Overexpression was performed according to the general procedure A, using *E. coli* BL21 (DE3) and Tuner(DE3)pLysS strains from Novagen. The protein was separated by electrophoresis in accordance with the general procedure described above.

EXAMPLE 11

The Fusion Protein of SEQ. No. 11

The protein of SEQ. No. 11 is a fusion protein having the length of 317 amino acids and the mass of 35.9 kDa, in which at the C-terminus of the sequence TRAIL116-281 a fragment of human interferon gamma (SEQ. No. 18) is attached as an effector peptide. Between the effector peptide and the sequence of TRAIL the protein contains sequences of protease cleavage sites recognized by metalloprotease MMP (SEQ. No. 20) and urokinase uPA (SEQ. No. 21) due to which the effector peptide will undergo cleavage in the tumour environment upon internalization of the fusion protein. Between SEQ. No. 20 and SEQ. No. 21 the fusion protein contains additionally linker for pegylation (SEQ. No. 22).

The protein comprises also flexible linkers: flexible glycine-serine linker GSGGG (SEQ. No. 26) between the sequence of effector peptide and metalloprotease MMP cleavage site; and flexible glycine-serine linker GSGGG (SEQ. No. 26) between the urokinase uPa cleavage site and TRAIL sequence.

Structure of the fusion protein is shown schematically in FIG. 2 and its amino acid sequence and the DNA encoding sequence comprising codons optimized for expression in *E. coli* are, respectively, SEQ. No. 11 and SEQ. No. 39 as shown in the attached Sequence Listing.

The amino acid sequence SEQ. No. 11 of the structure described above was used as a template to generate its coding DNA sequence SEQ. No. 39. A plasmid containing the coding sequence of DNA was generated and overexpression of the fusion protein was carried out in accordance with the general procedures described above. Overexpression was performed according to the general procedure A, using *E. coli* BL21 (DE3) and *E. coli* Tuner(DE3)pLysS strains from Novagen. The protein was separated by electrophoresis in accordance with the general procedure described above.

EXAMPLE 12

The Fusion Protein of SEQ. No. 12

The protein of SEQ. No. 12 is a fusion protein having the length of 449 amino acids and the mass of 51.8 kDa, in which at the N-terminus of the sequence TRAIL116-281 a single chain pseudodimer of human interferon gamma (SEQ. No. 19) is attached as an effector peptide. Between the effector peptide and the sequence of TRAIL the protein contains sequences of protease cleavage sites recognized by metalloprotease MMP (SEQ. No. 20) and urokinase uPA (SEQ. No. 21) due to which the effector peptide will undergo cleavage in the tumour environment upon internalization of the fusion protein.

The protein comprises also flexible linkers: flexible glycine-serine linker GSGGG (SEQ. No. 26) between the sequence of effector peptide and metalloprotease MMP cleavage site; and flexible glycine-serine linker GSGGG (SEQ. No. 26) between the urokinase uPa cleavage site and TRAIL sequence.

Figure 3:
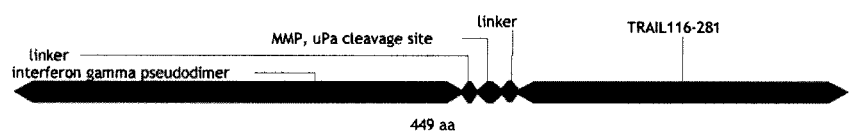
FIG. 3 presents schematic structures of fusion proteins of the invention according to Ex. 12, Ex. 13, Ex. 14 and Ex. 15.
Figure 3:
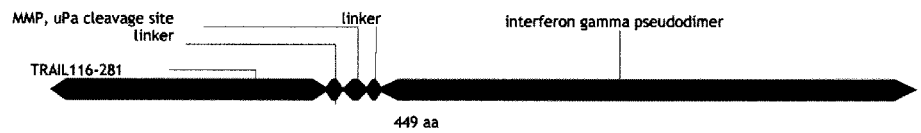
Figure 3:
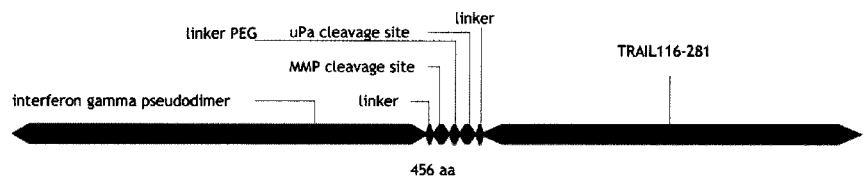
Figure 3:
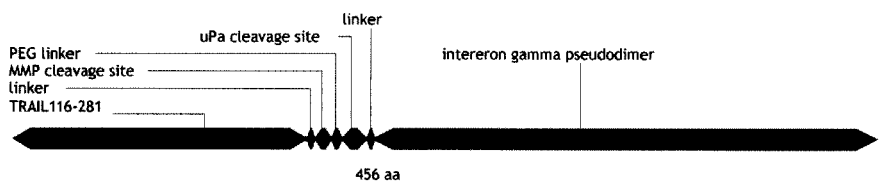

Structure of the fusion protein is shown schematically in FIG. 3 and its amino acid sequence and the DNA encoding sequence comprising codons optimized for expression in *E. coli* are, respectively, SEQ. No. 12 and SEQ. No. 40 as shown in the attached Sequence Listing.

The amino acid sequence SEQ. No. 12 of the structure described above was used as a template to generate its coding DNA sequence SEQ. No. 40. A plasmid containing the coding sequence of DNA was generated and overexpression of the fusion protein was carried out in accordance with the general procedures described above. Overexpression was performed according to the general procedure A, using *E. coli* BL21 (DE3) and *E. coli* Tuner(DE3)pLysS strains from Novagen. The protein was separated by electrophoresis in accordance with the general procedure described above.

EXAMPLE 13

The Fusion Protein of SEQ. No. 13

The protein of SEQ. No. 13 is a fusion protein having the length of 449 amino acids and the mass of 51.8 kDa, in which at the C-terminus of the sequence TRAIL116-281 a single chain pseudodimer of human interferon gamma (SEQ. No. 19) is attached as an effector peptide. Between the effector peptide and the sequence of TRAIL there are incorporated sequentially sequences of protease cleavage sites recognized by metalloprotease MMP (SEQ. No. 20) and urokinase uPA (SEQ. No. 21) due to which the effector peptide will undergo cleavage in the tumor environment upon internalization of the fusion protein.

The protein comprises also flexible linkers: flexible glycine-serine linker GSGGG (SEQ. No. 26) between the sequence of effector peptide and urokinase uPa cleavage site; and flexible glycine-serine linker GSGGG (SEQ. No. 26) between the metalloprotease MMP cleavage site and TRAIL sequence.

Structure of the fusion protein is shown schematically in FIG. 3 and its amino acid sequence and the DNA encoding sequence comprising codons optimized for expression in *E. coli* are, respectively, SEQ. No. 13 and SEQ. No. 41 as shown in the attached Sequence Listing.

The amino acid sequence SEQ. No. 13 presented above was used as a template to generate its coding DNA sequence SEQ. No 41 presented above. A plasmid containing the coding sequence of DNA was generated and overexpression of the fusion protein was carried out in accordance with the general procedures described above. Overexpression was performed according to the general procedure B, using *E. coli* B.21 (DE3) strain from Novagen and *E. coli* L21DE3pLysSRIL strain from Stratagene. The protein was separated by electrophoresis in accordance with the general procedure described above.

EXAMPLE 14

The Fusion Protein of SEQ. No. 14

The protein of SEQ. No. 14 is a fusion protein having the length of 456 amino acids and the mass of 52.4 kDa, in which at the N-terminus of the sequence TRAIL116-281 a single chain pseudodimer of human interferon gamma (SEQ. No. 19) is attached as an effector peptide. Between the effector peptide and the sequence of TRAIL there are incorporated sequences of protease cleavage sites recognized by metalloprotease MMP (SEQ. No. 20) and urokinase uPA (SEQ. No. 21) due to which the effector peptide will undergo cleavage in the tumour environment upon internalization of the fusion protein. Between the sequences SEQ. No. 20 and SEQ. No. 21 the fusion protein contains additionally linker for pegylation (SEQ. No. 22).

The protein comprises also flexible linkers: flexible glycine-serine linker GSGGG (SEQ. No. 26) between the sequence of effector peptide and urokinase uPa cleavage site; and flexible glycine-serine linker GSGGG (SEQ. No. 26) between the metalloprotease MMP cleavage site and TRAIL sequence.

Structure of the fusion protein is shown schematically in FIG. 3 and its amino acid sequence and the DNA encoding sequence comprising codons optimized for expression in *E. coli* are, respectively, SEQ. No. 14 and SEQ. No. 42 as shown in the attached Sequence Listing.

The amino acid sequence SEQ. No. 14 presented above was used as a template to generate its coding DNA sequence SEQ. No 42 presented above. A plasmid containing the coding sequence of DNA was generated and overexpression of the fusion protein was carried out in accordance with the general procedures described above. Overexpression was performed according to the general procedure B, using *E. coli* B.21 (DE3) strain from Novagen and *E. coli* BL21DE3pLysS8/L strain from Stratagene. The protein was separated by electrophoresis in accordance with the general procedure described above.

EXAMPLE 15

The Fusion Protein of SEQ. No. 15

The protein of SEQ. No. 15 is a fusion protein having the length of 456 amino acids and the mass of 52.4 kDa, in which at the C-terminus of the sequence TRAIL116-281 a single chain pseudodimer of human interferon gamma (SEQ. No. 19) is attached as an effector peptide. Between the sequence of TRAIL and the effector peptide the fusion protein contains sequences of protease cleavage sites recognized by metalloprotease MMP (SEQ. No. 20) and urokinase uPA (SEQ. No. 21) due to which the effector peptide will undergo cleavage in the tumour environment upon internalization of the fusion protein. Between the sequences SEQ. No. 20 and SEQ. No. 21 the fusion protein contains additionally the linker for pegylation (SEQ. No. 22).

The protein comprises also flexible linkers: flexible glycine-serine linker GSGGG (SEQ. No. 26) between the sequence of effector peptide and urokinase uPa cleavage site; and flexible glycine-serine linker GSGGG (SEQ. No. 26) between the sequence of TRAIL and the metalloprotease MMP cleavage site.

Structure of the fusion protein is shown schematically in FIG. 3 and its amino acid sequence and the DNA encoding sequence comprising codons optimized for expression in *E.* coli are, respectively, SEQ. No. 15 and SEQ. No. 43 as shown in the attached Sequence Listing.

The amino acid sequence SEQ. No. 15 presented above was used as a template to generate its coding DNA sequence SEQ. No. 43 presented above. A plasmid containing the coding sequence of DNA was generated and overexpression of the fusion protein was carried out in accordance with the general procedures described above. Overexpression was performed according to the general procedure B, using *E. coli* B.21 (DE3) strain from Novagen and *E. coli* L21DE3pLysSRIL strain from Stratagene. The protein was separated by electrophoresis in accordance with the general procedure described above.

EXAMPLE 16

The Fusion Protein of SEQ. No. 44

The protein of SEQ. No. 44 is a fusion protein having the length of 538 amino acids and the mass of 62.4 kDa, in which at the N-terminus of the sequence TRAIL122-281 a single chain pseudodimer of human interferon alpha 2b (SEQ. No. 46) is attached as an effector peptide. Between the sequence of the effector peptide and the sequence of TRAIL there are incorporated two combinations of sequences of protease cleavage sites recognized by metalloprotease MMP (SEQ. No. 20) and urokinase uPA (SEQ. No. 21) due to which the effector peptide will undergo cleavage in the tumour environment upon internalization of the fusion protein. Between the two combinations of sequences SEQ. No. 20 and SEQ. No. 21 the fusion protein contains additionally linker for pegylation (SEQ. No. 22).

Figure 4:
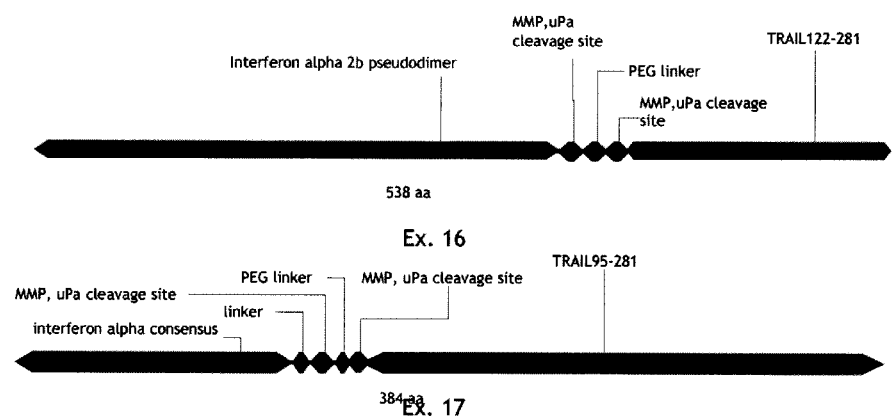
FIG. 4 presents schematic structures of fusion proteins of the invention according to Ex. 16 and Ex. 17.

Structure of the fusion protein is shown schematically in FIG. 4 and its amino acid sequence and the DNA encoding sequence comprising codons optimized for expression in *E. coli* are, respectively, SEQ. No. 44 and SEQ. No. 48 as shown in the attached Sequence Listing.

The amino acid sequence SEQ. No. 44 presented above is used as a template to generate its coding DNA sequence SEQ. No 48 presented above. A plasmid containing the coding sequence of DNA can be generated and overexpression of the fusion protein carried out in accordance with the general procedures described above. Overexpression can be performed according to the general procedure B, using *E. coli* B.21 (DE3) strain from Novagen and *E. coli* L21DE3pLysSRIL strain from Stratagene. The protein can be separated by electrophoresis in accordance with the general procedure described above.

EXAMPLE 17

The Fusion Protein of SEQ. No. 45

The protein of SEQ. No. 45 is a fusion protein having the length of 384 amino acids and the mass of 44 kDa, in which at the N-terminus of the sequence TRAIL95-281 a consensus sequence of human interferon alpha (SEQ. No. 47) is attached as an effector peptide. Between the sequence of the effector peptide and the sequence of TRAIL there are incorporated two combinations of sequences of protease cleavage sites recognized by metalloprotease MMP (SEQ. No. 20) and urokinase uPA (SEQ. No. 21) due to which the effector peptide will undergo cleavage in the tumour environment upon internalization of the fusion protein. Between the combinations of sequences SEQ. No. 20 and SEQ. No. 21 the fusion protein contains additionally linker for pegylation (SEQ. No. 22). The protein comprises also flexible glycine-serine linker GGSG (SEQ. No. 50) between the sequence of effector peptide and metalloprotease MMP cleavage site.

Structure of the fusion protein is shown schematically in FIG. 4 and its amino acid sequence and the DNA encoding sequence comprising codons optimized for expression in *E. coli* are, respectively, SEQ. No. 45 and SEQ. No. 49 as shown in the attached Sequence Listing.

The amino acid sequence SEQ. No. 45 presented above is used as a template to generate its coding DNA sequence SEQ. No 49 presented above. A plasmid containing the coding sequence of DNA can be generated and overexpression of the fusion protein carried out in accordance with the general procedures described above. Overexpression can be performed according to the general procedure B, using *E. coli* B.21 (DE3) strain from Novagen and *E. coli* L21DE3pLysSRIL strain from Stratagene. The protein can separated by electrophoresis in accordance with the general procedure described above.

EXAMPLE 18

Examination of Anti-Tumor Activity of the Fusion Proteins

Examination of anti-tumor activity of the fusion proteins was carried out in vitro in a cytotoxicity assay on tumor cell lines and in vivo in mice. For comparison purposes, rhTRAIL114-281 protein and placebo were used.

1. Measurement of Circular Dichroism

Quality of the preparations of fusion proteins in terms of their structure was determined by circular dichroism (CD) for Ex. 3, Ex. 5, Ex. 12 and Ex. 14.

Circular dichroism is used for determination of secondary structures and conformation of protein. CD method uses optical activity of the protein structures, manifested in rotating the plane of polarization of light and the appearance of elliptical polarization. CD spectrum of proteins in far ultraviolet (UV) provides precise data on the conformation of the main polypeptide chain.

Samples of the protein to be analysed after formulation into a buffer consisting of 50 mM Tris-HCl pH 8.0, 100 mM NaCl, 10% glycerol, 0.1 mM $ZnCl_2$, 80 mM saccharose, 5 mM DTT were dialysed in the dialysis bags (Sigma-Aldrich) with cut off 12 kDa. Dialysis was performed against 100 fold excess (v/v) of buffer comparing to the protein preparations with stirring for several hours at 4° C. After dialysis was completed, each preparation was centrifuged (25 000 rpm, 10 min., 4° C.) and the appropriate supernatants were collected. Protein concentration in the samples thus obtained was determined by Bradford method.

Measurement of circular dichroism for proteins in the concentration range of 0.1-2.7 mg/ml was performed on Jasco J-710 spectropolarimeter, in a quartz cuvette with optical way 0.2 mm or 1 mm. The measurement was performed under the flow of nitrogen at 7 l/min, which allowed to perform of the measurement in the wavelength range from 195 to 250 nm. Parameters of the measurement: spectral resolution of −1 nm; half width of the light beam 1 nm; sensitivity 20 mdeg, the averaging time for one wavelength −8 s, scan speed 10 nm/min.

Figure 5:
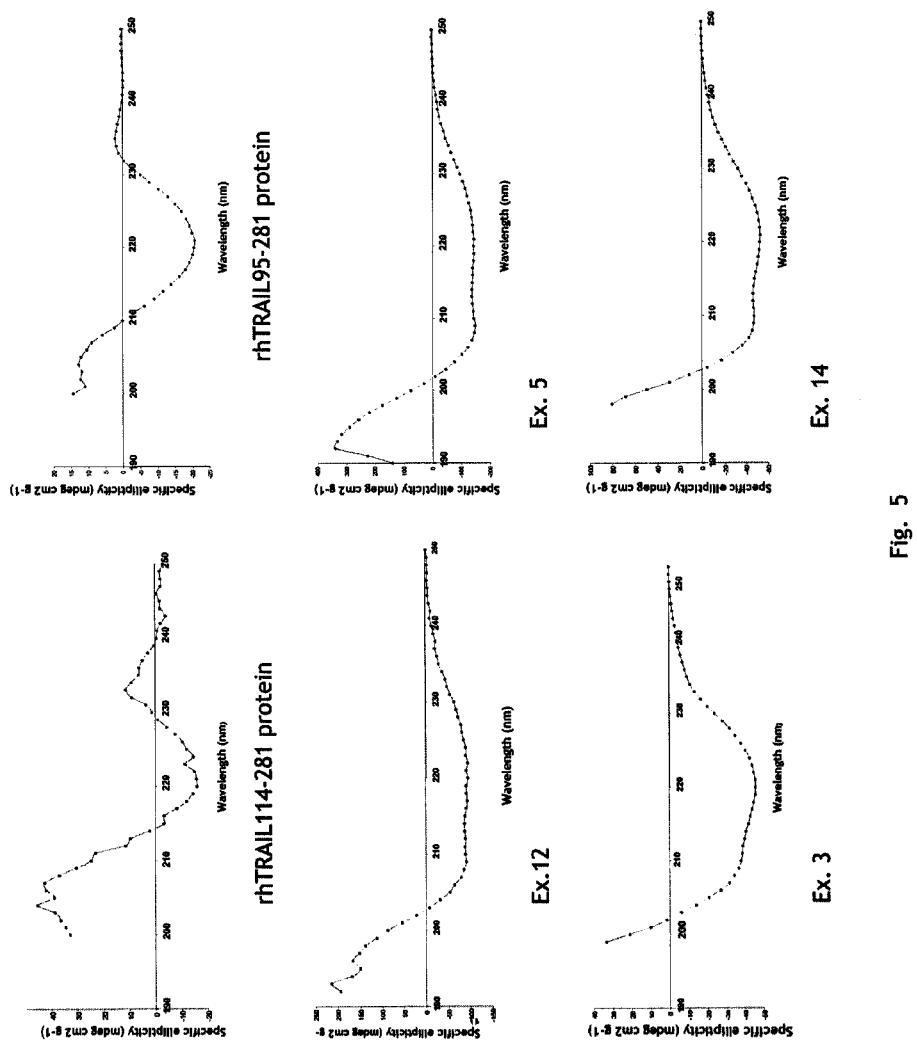
FIG. 5 shows circular dichroism spectra for rhTRAIL114-281, rhTRAIL95-281 and fusion proteins of Ex. 12, Ex. 5, Ex. 3 and Ex. 14 expressed in specific ellipticity.

The results were presented as the average of three measurements. Circular dichroism spectra for rhTRAIL114-281, rhTRAIL95-281 and proteins of Ex. 12, Ex. 5, Ex. 3 and Ex. 14 are presented in FIG. 5.

Obtained spectra were analyzed numerically in the range of 193-250 nm using CDPro software. Points for which the voltage at the photomultiplier exceeded 700 V were omitted, due to too low signal to noise ratio in this wavelength range.

The data obtained served for calculations of particular secondary structures content in the analyzed proteins with use of CDPro software (Table 1).

TABLE 1

Content of secondary structures in the analyzed proteins

| Protein | NRMSD (Exp-Cal) | α-helix | β-sheet | Schift | Disorder |
|---|---|---|---|---|---|
| Ex. 3 | 0.018 | 98.0% | 1.5% | 0.0% | 0.5% |
| Ex. 5 | 0.048 | 45.6% | 8.2% | 18.8% | 27.4% |
| Ex. 12 | 0.104 | 39.3% | 17.3% | 15.0% | 28.4% |
| Ex. 14 | 0.01 | 100.0% | 0.0% | 0.0% | 0.0% |
| hrTRAIL* | | 1.94% | 50.97% | 7.74% | 39.35% |
| hrTRAIL114-281 | 0.389 | 4.9% | 33.7% | 23.1% | 38.3% |
| hrTRAIL 95 | 0.074 | 0.0% | 21.6% | 16.0% | 62.4% |

*value obtained on the basis on crystalline structure 1D4V

Controls (rhTRAIL114-281 and rhTRAIL95-281) show CD spectrum characteristic for the proteins with predominantly type β-sheet structures (sharply outlined ellipticity minimum at the wavelength 220 nm). This confirms the calculation of secondary structure components, which suggests a marginal number of α-helix elements.

The obtained result is also consistent with data from the crystal structure of TRAIL protein, wherein beta elements constitute more than half of its composition.

In the case of fused proteins of Ex. 3, Ex. 5, Ex. 12 and Ex. 14, dichroism spectra are characterized by two minima at wavelengths 208 and 220 nm, which is characteristic for proteins with mixed secondary structure of alpha/beta type. Interferon molecules attached to TRAIL in the fused proteins form predominantly alpha-helical structures, therefore the mixed nature of secondary structures in the analyzed chimeric proteins can confirm the presence of properly folded elements of both TRAIL and interferon.

In the case of preparations according to Ex. 3. and Ex. 14, almost 100% of alpha-type structures was found. Such a content of alpha type structures is due to narrow range of wavelength used in analysis, which is a consequence of the selection of formulations optimal for methods and materials (high amount of noise in the far-UV). The absence of sharply outlined range of 180-200 nm in the analyzed region of the spectrum can cause that content of α-helix structures is overestimated.

2. Tests on Cell Lines in Vitro

Cell Lines

TABLE 2

Adherent cell lines

| Cell line | Cancer type | Medium | number of cells per well (thousands) |
|---|---|---|---|
| Colo 205 ATCC #CCL-222 | human colorectal cancer | RPMI + 10% FBS + penicillin + streptomycin | 5 |
| HT-29 ATCC # CCL-2 | human colorectal cancer | McCoy's + 10% FBS + penicillin + streptomycin | 5 |
| DU-145 ATCC # HTB-81 | human prostate cancer | RPMI + 10% FBS + penicillin + streptomycin | 3 |
| PC-3 ATCC # CRL-1435 | human prostate cancer | RPMI + 10% FBS + penicillin + streptomycin | 4 |
| MCF-7 ATCC #HTB-22 | human breast cancer | MEM + 10% FBS + penicillin + streptomycin | 4, 5 |
| MDA-MB-231 ATCC # HTB-26 | human breast cancer | DMEM + 10% FBS + penicillin + streptomycin | 4, 5 |
| UM-UC-3 ATCC # CLR-1749 | human bladder cancer | MEM + 10% FBS + penicillin + streptomycin | 3, 5 |
| SW780 ATCC #CRL-2169 | human bladder cancer | DMEM + 10% FBS + penicillin + streptomycin | 3 |
| SW620 ATCC #CCL-227 | human colorectal cancer | DMEM + 10% FBS + penicillin + streptomycin | 5 |
| BxPC-3 ATCC #CRL-1687 | human pancreatic cancer | RPMI + 10% FBS + penicillin + streptomycin | 4, 5 |
| SK-OV-3 ATCC # HTB-77 | human ovarian cancer | McCoy's + 10% FBS + penicillin + streptomycin | 4 |
| NIH: OVCAR-3 ATCC #HTB-161 | human ovarian cancer | RPMI + 20% FBS + 0.01 mg/ml insulin + penicillin + streptomycin | 7 |
| HepG2 ATCC # HB-8065 | human liver hepatoma | MEM + 10% FBS + penicillin + streptomycin | 7 |
| 293 ATCC # CLR-1573 | Human embrional kidney cells | MEM + 10% FBS + penicillin + streptomycin | 4 |
| ACHN ATCC #CCL-222 | human kidney cancer | MEM + 10% FBS + penicillin + streptomycin | 4 |
| CAKI 2 ATCC # HTB-47 | human kidney cancer | McCoy's + 10% FBS + penicillin + streptomycin | 3, 5 |
| NCI-H69AR ATCC #CRL-11351 | human small cell lung cancer | RPMI + 10% FBS + penicillin + streptomycin | 10 |
| HT144 ATCC # HTB-63 | human melanoma cells | McCoy's + 10% FBS + penicillin + streptomycin | 7 |
| NCI-H460 ATCC #HTB-177 | human lung cancer | MEM + 10% FBS + penicillin + streptomycin | 2, 5 |
| LNCaP ATCC # CRL-1740 | human prostate cancer | RPMI + 10% FBS + penicillin + streptomycin | 4, 5 |

TABLE 3

| Cell line | Cancer type | Medium | Number of cells per well (thousands) |
|---|---|---|---|
| NCI-H69 ATCC# HTB-119 | human small cell lung cancer | RPMI + 10% FBS + penicillin + streptomycin | 22 |
| Jurkat A3 ATCC#CRL-2570 | human leukaemia | RPMI + 10% FBS + penicillin + streptomycin | 10 |
| HL60 ATCC# CCL-240 | human leukaemia | RPMI + 20% FBS + penicillin + streptomycin | 10 |
| CCRF-CEM ATCC# CCL-119 | human leukaemia | RPMI + 20% FBS + penicillin + streptomycin | 10 |

MTT Cytotoxicity Test

MTT assay is a colorimetric assay used to measure proliferation, viability and cytotoxicity of cells. It consists in decomposition of a yellow tetrazolium salt MTT (4,5-dimethyl-2-thiazolyl)-2,5-diphenyltetrazolium bromide) to the water-insoluble purple dye formazan by mitochondrial enzyme succinate-tetrazolium reductase 1. MTT reduction occurs only in living cells. Data analysis consists in determining $IC_{50}$ concentration of the protein (in ng/ml), at which the 50% reduction in the number of cells occurs in the population treated compared to control cells. Results were analyzed using GraphPad Prism 5.0 software. The test was performed according to the literature descriptions (Celis, J E, (1998). Cell Biology, a Laboratory Handbook, second edition, Academic Press, San Diego; Yang, Y., Koh, L W, Tsai, J H., (2004); Involvement of viral and chemical factors with oral cancer in Taiwan, Jpn J Clin Oncol, 34 (4), 176-183).

Cell culture medium was diluted to a defined density ($10^4$-$10^5$ cells per 100 µl). Then 100 µl of appropriately diluted cell suspension was applied to a 96-well plate in triplicates. Thus prepared cells were incubated for 24 h at 37° C. in 5% or 10% $CO_2$, depending on the medium used, and then to the cells (in 100 µl of medium) further 100 µl of the medium containing various concentrations of tested proteins were added. After incubation of the cells with tested proteins over the period of next 72 hours, which is equivalent to 3-4 times of cell division, the medium with the test protein was added with 20 ml of MTT working solution [5 mg/ml], and incubation was continued for 3 h at 37° C. in 5% $CO_2$. Then the medium with MTT solution was removed, and formazan crystals were dissolved by adding 100 µl of DMSO. After stirring, the absorbance was measured at 570 nm (reference filter 690 nm).

EZ4U Cytotoxicity Test

EZ4U (Biomedica) test was used for testing cytotoxic activity of the proteins in nonadherent cell lines. The test is a modification of the MTT wherein formazan formed in the reduction of tetrazolium salt is water-soluble. Cell viability study was carried out after continuous 72-hour incubation of the cells with protein (seven concentrations of protein, each in triplicates). On this basis $IC_{50}$ values were determined (as an average of two independent experiments) using the GraphPad Prism 5 software.

The results of in vitro cytotoxicity tests are summarized in Table 4 and Table 5, as $IC_{50}$ values (ng/ml), which corresponds to a protein concentration at which the cytotoxic effect of fusion proteins is observed at the level of 50% with respect to control cells treated only with solvent. Each experiment represents the average value of at least two independent experiments performed in triplicates. As a criterion of lack of activity of protein preparations the $IC_{50}$ limit of 2000 ng/ml was adopted. Fusion proteins with an $IC_{50}$ value above 2000 were considered inactive.

Cells for this test were selected so as to include the tumor cell lines naturally resistant to TRAIL protein (the criterion of natural resistance to TRAIL: $IC_{50}$ for TRAIL protein>2000), tumor cell lines sensitive to TRAIL protein and resistant to doxorubicin line MES-SA/DX5 as a cancer line resistant to conventional anticancer medicaments.

Undifferentiated HUVEC cell line was used as a healthy control cell line for assessment of the effect/toxicity of the fusion proteins in non-cancer cells.

The results obtained confirm the possibility of overcoming the resistance of the cell lines to TRAIL by administration of certain fusion proteins of the invention to cells naturally resistant to TRAIL. When fusion proteins of the invention into the cells sensitive to TRAIL were administered, in some cases a clear and strong potentiation of the potency of action was observed, manifesting in reduced $IC_{50}$ values of the fusion protein compared with $IC_{50}$ for the TRAIL alone. Furthermore, cytotoxic activity of the fusion protein of the invention in the cells resistant to classical anti-cancer medicament doxorubicin was obtained, and in some cases was stronger than activity of TRAIL alone.

The $IC_{50}$ values above 2000 obtained for the non-cancer cell lines show the absence of toxic effects associated with the use of proteins of the invention for healthy cells, which indicates potential low systemic toxicity of the protein.

Determination of Cytotoxic Activity of Selected Protein Preparations Against Extended Panel of Tumour Cell Lines Table 5 presents the results of the tests of cytotoxic activity in vitro for selected fusion proteins of the invention against a broad panel of tumour cells from different organs, corresponding to the broad range of most common cancers. Obtained $IC_{50}$ values confirm high cytotoxic activity of fusion proteins and thus their potential utility in the treatment of cancer.

TABLE 4

Cytotoxic activity of fusion proteins of the invention

Continuous incubation of preparations with cells over 72 h (MTT test, ng/ml)

| Protein | MES-SA $IC_{50}$ | ±SD | MES-SA/Dx5 $IC_{50}$ | ±SD | HCT116 $IC_{50}$ | ±SD | SK-MES-1 $IC_{50}$ | ±SD | A549 $IC_{50}$ | ±SD | MCF10A $IC_{50}$ | ±SD |
|---|---|---|---|---|---|---|---|---|---|---|---|---|
| rhTRAIL95-281 | >2000 | | 32.2 | 2.40 | 173 | 31.3 | 12.2 | 2.33 | >2000 | | >2000 | |
| Ex. 1 | 196.5 | 11.74 | 46.9 | 0.16 | 210.7 | 102.67 | 108.2 | 28.43 | >2000 | | >2000 | |
| Ex. 3 | 68.31 | 3.5 | 26.54 | 5.2 | 37.97 | 1.9 | 17.91 | 34.1 | 872.2 | 85.3 | >2000 | |
| Ex. 5 | 57.18 | 40.8 | 14.11 | 6.7 | 72.1 | 36.1 | 53.84 | 30.9 | 1326 | 888.2 | >2000 | |
| Ex. 12 | 1.33 | 0.54 | 2.73 | 2.23 | 1.90 | 0.22 | 1.82 | 1.00 | 526 | 107.4 | >2000 | |
| Ex. 14 | 0.09 | 0.01 | 0.059 | 0.08 | 2.10 | 0.33 | 0.06 | 0.01 | 672.80 | 8.20 | >2000 | |

TABLE 5

Analysis of cytotoxic activity of selected protein preparations against broad panel of tumour cell lines

| Cell line | COLO 205 mean | SD | HT 29 mean | SD | SW 620 mean | SD | MCF 7 mean | SD |
|---|---|---|---|---|---|---|---|---|
| rhTRAIL95-281 | 24.9 | 17.68 | 10000 | | 10000 | | 10000 | |
| Ex. 14 | 2.916 | 0.70 | 131.5 | 33.23 | 562.5 | 371.7 | 3901 | 2745.7 |

| Cell line | SW 780 mean | SD | UM-UC-3 mean | SD | 293 mean | SD | CAKI 2 mean | SD |
|---|---|---|---|---|---|---|---|---|
| rhTRAIL95-281 | 120 | 42.43 | 2242 | 1367 | 10000 | | 10000 | |
| Ex. 14 | 0.766 | 1.04 | 3.154 | 0.21 | 10000 | 0.0 | 6594 | 3661.4 |

| Cell line | NCI-H460 mean | SD | BxPC3 mean | SD | HepG2 mean | SD | HT 144 mean | SD |
|---|---|---|---|---|---|---|---|---|
| rhTRAIL95-281 | 5889 | 111.0 | 64.71 | 31.81 | 10000 | | 1734 | 218.5 |
| Ex. 14 | 0.547 | 0.25 | 0.137 | 0.11 | 10000 | 0.00 | 0.13 | 0.02 |

| Cell line | COLO 205 mean | SD | HT 29 mean | SD | SW 620 mean | SD | MCF 7 mean | SD |
|---|---|---|---|---|---|---|---|---|
| rhTRAIL95-281 | 24.9 | 17.68 | 10000 | | 10000 | | 10000 | |
| Ex. 5 | 5.717 | 1.69 | 159.6 | 7.64 | 683.5 | 477.3 | 867.5 | 108.2 |

| Cell line | SW 780 mean | SD | UM-UC-3 mean | SD | 293 mean | SD | CAKI 2 mean | SD |
|---|---|---|---|---|---|---|---|---|
| rhTRAIL95-281 | 120 | 42.43 | 2242 | 1367 | 10000 | | 10000 | |
| Ex. 5 | 18.68 | 2.37 | 21.29 | 2.10 | 1126 | 291.0 | 2799 | 371.2 |

| Cell line | NCI-H460 mean | SD | BxPC3 mean | SD | HepG2 mean | SD | HT 144 mean | SD |
|---|---|---|---|---|---|---|---|---|
| rhTRAIL95-281 | 5889 | 111.0 | 64.71 | 31.81 | 10000 | | 1734 | 218.5 |
| Ex. 5 | 22.95 | 2.57 | 17.6 | 0.85 | 1174 | 58.69 | 26.85 | 2.94 |

| Cell line | MDA-M8-231 mean | SD | DU 145 mean | SD | LNCaP mean | SD | PC 3 mean | SD |
|---|---|---|---|---|---|---|---|---|
| rhTRAIL95-281 | 10000 | | 10000 | | 2052 | 466.0 | 10000 | |
| Ex. 14 | 6.38 | 3.21 | 34.75 | 12.37 | 1378 | 377.60 | 1325 | |

| Cell line | SK-OV-3 mean | SD | OV-CAR-3 mean | SD | H69AR mean | SD | NCI-H69 mean | SD |
|---|---|---|---|---|---|---|---|---|
| rhTRAIL95-281 | 10000 | | 93.1 | 8.34 | 10000 | | 10000 | |
| Ex. 14 | 8172 | 2585.9 | 0.007 | 0.01 | 3889 | 864.79 | 10000 | |

TABLE 5-continued

Analysis of cytotoxic activity of selected protein preparations against broad panel of tumour cell lines

| Cell line | ACHN | | JURKAT A3 | | HL60 | | CCRF-CEM | |
|---|---|---|---|---|---|---|---|---|
| | mean | SD | mean | SD | mean | SD | mean | SD |
| rhTRAIL95-281 Ex. 14 | 10000 2.95 | 1.29 | 10000 0.112 | 0.1 | 10000 10000 | | 10000 10000 | |

| Cell line | MDA-M8-231 | | DU 145 | | LNCaP | | PC 3 | |
|---|---|---|---|---|---|---|---|---|
| | mean | SD | mean | SD | mean | SD | mean | SD |
| rhTRAIL95-281 Ex. 5 | 10000 108.8 | 18.67 | 10000 296.9 | 65.20 | 2052 459.9 | 466.0 45.04 | 10000 1649 | 861.3 |

| Cell line | SK-OV-3 | | OV-CAR-3 | | H69AR | | NCI-H69 | |
|---|---|---|---|---|---|---|---|---|
| | mean | SD | mean | SD | mean | SD | mean | SD |
| rhTRAIL95-281 Ex. 5 | 10000 5221 | 170.4 | 93.1 15.03 | 8.34 0.69 | 10000 1251 | 94.05 | 10000 5270 | 763.7 |

| Cell line | ACHN | | JURKAT A3 | | HL60 | | CCRF-CEM | |
|---|---|---|---|---|---|---|---|---|
| | mean | SD | mean | SD | mean | SD | mean | SD |
| rhTRAIL95-281 Ex. 5 | 10000 187.3 | 45.61 | 10000 372.2 | 225.1 | 10000 7000 | | 10000 7000 | |

2. Antitumour Effectiveness of Fusion Proteins in Vivo on Xenografts

Antitumour activity of protein preparations was tested in a mouse model of human colon cancer HCT116

Cells

The HCT116 cells were maintained in RPMI 1640 medium (Hyclone, Logan, Utah, USA) mixed in the ratio of 1:1 with Opti-MEM ((Invitrogen, Cat.22600-134) supplemented with 10% fetal calf serum and 2 mM glutamine. On the day of mice grafting, the cells were detached from the support by washing the cells with trypsin (Invitrogen), then the cells were centrifuged at 1300 rpm, 4° C., 8 min., suspended in HBSS buffer (Hanks medium), counted and diluted to the concentration of $25 \times 10^6$ cells/ml.

The PLC/PRF/5 (CLS) cells were maintained in DMEM (HyClone, Logan, Utah, USA) supplemented with 10% fetal calf serum and 2 mM glutamine. On the day of mice grafting, the cells were detached from the support by washing the cells with trypsin (Invitrogen), then the cells were centrifuged at 1300 rpm, 4° C., 8 min., suspended in HBSS buffer (Hanks medium), counted and diluted to the concentration of $25 \times 10^6$ cells/ml.

The HepG2 cells were maintained in MEM (HyClone, Logan, Utah, USA) supplemented with 10% fetal calf serum and 2 mM glutamine. On the day of mice grafting, the cells were detached from the support by washing the cells with trypsin (Invitrogen), then the cells were centrifuged at 1300 rpm, 4° C., 8 min., suspended in HBSS buffer (Hanks medium), counted and diluted to the concentration of $25 \times 10^6$ cells/ml.

Mice

Examination of antitumor activity of proteins of the invention was conducted on 7-9 week-old CD-nude (Crl:CD1-Foxn1$^{nu}$ 1) or on 4-5 week old Crl:SHO-Prkdc$^{scid}$Hr$^{hr}$ mice obtained from Charles River Germany. Mice were kept under specific pathogen-free conditions with free access to food and demineralised water (ad libitum). All experiments on animals were carried in accordance with the guidelines: "Interdisciplinary Principles and Guidelines for the Use of Animals in Research, Marketing and Education" issued by the New York Academy of Sciences' Ad Hoc Committee on Animal Research and were approved by the IV Local Ethics Committee on Animal Experimentation in Warsaw (No. 71/2009).

The Course and Evaluation of the Experiments

Human Colon Cancer Model

Mice Crl:CD1-Foxn1$^{nu}$ 1

On day 0 mice Crl:CD1-Foxn1$^{nu}$ 1 were grafted subcutaneously (sc) in the right side with $5 \times 10^6$ of HCT116 cells suspended in 0.2 ml HBSS buffer by means of a syringe with a 0.5×25 mm needle (Bogmark). When tumors reached the size of ~50-140 mm$^3$ (day 14), mice were randomized to obtain the average size of tumors in the group of ~70 mm$^3$ and assigned to treatment groups. The treatment groups were administered with the preparations of fusion proteins of the invention of Ex. 3, Ex. 12 and Ex.14 (10 mg/kg), and rhTRAIL114-281 (10 mg/kg) as a comparative reference and formulation buffer (5 mM NaH$_2$PO$_4$, 95 mM Na$_2$HPO$_4$, 200 mM NaCl, 5 mM glutathione, 0.1 mM ZnCl$_2$, 10% glycerol, 80 mM saccharose, pH 8.0) as a control. The preparations were administered intravenously (i.v.) daily for ten days on days 8-12 and 15-19. When a therapeutic group reached the average tumor size of ~1000 mm$^3$, mice were sacrificed by disruption of the spinal cord. The control group received rhTRAIL114-281.

Mice Crl:SHO-Prkdc$^{scid}$Hr$^{hr}$

On day 0 mice Crl:SHO-Prkdc$^{scid}$Hr$^{hr}$ were grafted subcutaneously (sc) in the right side with $5 \times 10^6$ of HCT116 cells suspended in 0.1 ml HBSS buffer by means of a syringe with a 0.5×25 mm needle (Bogmark). When tumors reached the size of 200-700 mm$^3$ (day 18), mice were randomized to obtain the average size of tumors in the group of ~400 mm$^3$ and assigned to treatment groups. The treatment groups were administered with the preparations of fusion proteins of the invention of Ex. 14 (50 mg/kg), rhTRAIL114-281 (20 mg/kg) as a comparative reference and formulation buffer (5 mM NaH$_2$PO$_4$, 95 mM Na$_2$HPO$_4$, 200 mM NaCl, 5 mM glutathione, 0.1 mM ZnCl$_2$, 10% glycerol, 80 mM saccharose, pH 8.0) as a control. The preparations were administered intravenously (i.v.) 6 times every second day. On the 32$^{nd}$ day of the experiment the mice were sacrificed by disruption of the spinal cord.

Human Liver Cancer Model
PLC/PRF/5 Cells

On day 0 mice Crl:SHO-Prkdc$^{scid}$Hr$^{hr}$ were grafted subcutaneously (sc) in the right side with 7×10$^6$ of PLC/PRF/5 cells suspended in 0.1 ml mixture of HBSS:Matrigel (3:1) buffer by means of a syringe with a0.5×25 mm needle (Bogmark). When tumors reached the size of 140-300 mm$^3$ (day 31), mice were randomized to obtain the average size of tumors in the group of –200 mm$^3$ and assigned to treatment groups. The treatment groups were administered with the preparations of fusion proteins of the invention of Ex. 14 (20 mg/kg), rhTRAIL114-281 (30 mg/kg) as a comparative reference, and formulation buffer (5 mM NaH$_2$PO$_4$, 95 mM Na$_2$HPO$_4$, 200 mM NaCl, 5 mM glutathione, 0.1 mM Zn 10% glycerol, 80 mM saccharose, pH 8.0) as a control. The preparations were administered intravenously (i.v.) 4 times every third day and subsequently 2 times every second day (q3dx4 and q2dx2). On the 32$^{nd}$ day of the experiment the mice were sacrificed by disruption of the spinal cord.

HepG2 Cells

On day 0 mice Crl:SHO-Prkdc$^{scid}$Hr$^{hr}$ were grafted subcutaneously (sc) in the right side with 7×10$^6$ of HepG2 cells suspended in 0.1 ml mixture of HBSS:Matrigel (3:1) buffer by means of a syringe with a 0.5×25 mm needle (Bogmark). When tumors reached the size of 250-390 mm$^3$ (day 19), mice were randomized to obtain the average size of tumors in the group of –330 mm$^3$ and assigned to treatment groups. The treatment groups were administered with the preparations of fusion proteins of the invention of Ex. 14 (50 mg/kg), rhTRAIL114-281 (30 mg/kg) as a comparative reference, and against formulation buffer (5 mM NaH$_2$PO$_4$, 95 mM Na$_2$HPO$_4$, 200 mM NaCl, 5 mM glutathione, 0.1 mM ZnCl$_2$, 10% glycerol, 80 mM saccharose, pH 8.0) as a control. The preparations were administered intravenously (i.v.) 6 times every second day. On the 31 day of the experiment the mice were sacrificed by disruption of the spinal cord.

Tumor size was measured using an electronic calliper, tumor volume was calculated using the formula: $(a^2 \times b)/2$, where a=shorter diagonal of the 25 tumor (mm) and b=longer diagonal of the tumor (mm). Inhibition of tumor growth was calculated using the formula:

$$\text{TGI [\%] (Tumor growth inhibition)} = (WT/WC) \times 100 - 100\%$$

wherein WT refers to the average tumor volume in the treatment group, WC refers to the average tumor volume in the control group.

The experimental results are presented as a mean value±standard deviation (SD). All calculations and graphs were prepared using the GraphPad Prism 5.0 software.

Figure 6:
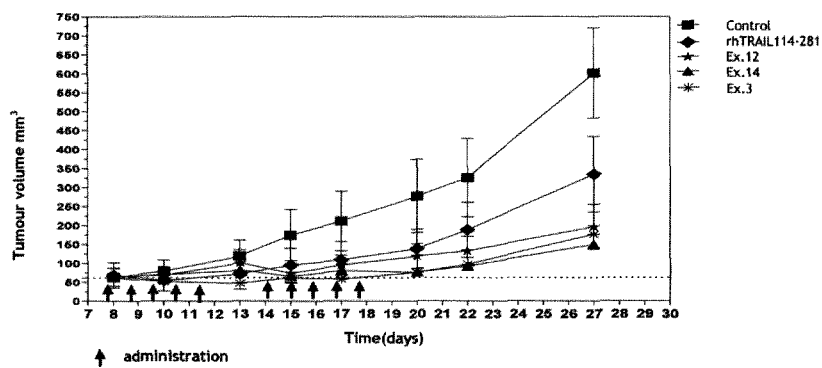
FIG. 6 presents tumor volume changes (% of initial stage) in Crl:CD1-Foxn1nu mice burdened with colon cancer HCT116, treated with fusion proteins of the invention of Ex. 3, Ex. 12 and Ex. 14 compared to rhTRAIL114-281.
Figure 7:
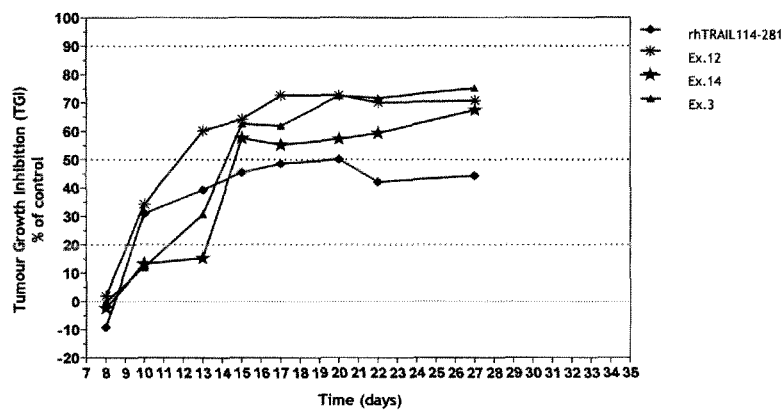
FIG. 7 presents the tumor growth inhibition values (% TGI) in Crl:CD1-Foxn1$^{nu}$ 1 mice burdened with colon cancer HCT116, treated with fusion proteins of the invention of Ex. 3, Ex. 12 and Ex. 14 compared to rhTRAIL114-281.

The experimental results obtained in mice Crl:CD1-Foxn1$^{nu}$ burdened with HCT116 colon cancer treated with fusion proteins of the invention of Ex. 3, Ex. 12 and Ex. 14 and comparatively with rhTRAIL114-281 are shown in FIG. 6 as a diagram of changes of the tumor volume and in FIG. 7 which shows tumor growth inhibition (% TGI) as the percentage of control.

The results of experiments presented in the graphs in FIGS. 6 and 7 show that administration of the fusion proteins of the invention of Ex. 3, Ex. 12 and Ex.14 caused tumor HCT116 growth inhibition, with TGI respectively 71%, 67% and 75% relative to the control on 28th day of the experiment. For rhTRAIL114-281 used as the comparative reference, a slight inhibitory effect on tumor cell growth was obtained relative to the control, with TGI at the level of 44%. Thus, fusion proteins of the invention exert much stronger effect compared to TRAIL alone.

Figure 8:
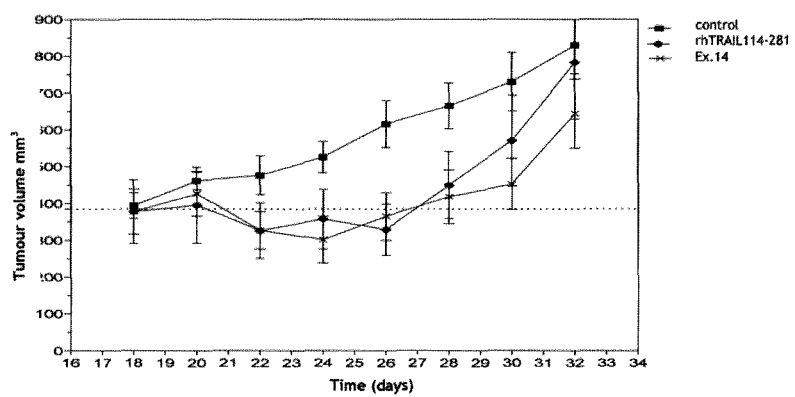
FIG. 8 presents tumor volume changes (% of initial stage) in Crl:SHO-PrkdcscidHrhr mice burdened with colon cancer HCT116 treated with fusion protein of the invention of Ex. 14 compared to rhTRAIL114-281.
Figure 9:
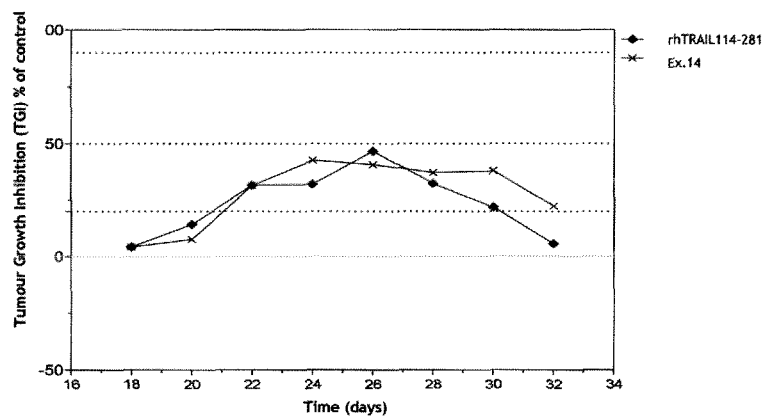
FIG. 9 presents the tumor growth inhibition values (% TGI) in Crl:SHO-PrkdcscidHrhr mice burdened with colon cancer HCT116 treated with fusion protein of the invention of Ex. 14 compared to rhTRAIL114-281.

The experimental results obtained in mice Crl:SHO-Prkdc$^{scid}$Hr$^{hr}$ burdened with HCT116 colon cancer treated with fusion protein of the invention of Ex. 14 20 mg/kg) and comparatively with rhTRAIL114-281 are shown in FIG. 8 as a diagram of changes of the tumor volume and in FIG. 9 which shows tumor growth inhibition (% TGI) as the percentage of control.

The results of experiments presented in the graphs in FIGS. 8 and 9 show that administration of the fusion protein of the invention of Ex. 14 caused tumor HCT116 growth inhibition, with TGI 22.5% relative to the control on 32$^{nd}$ day of the experiment. For rhTRAIL114-281 used as the comparative reference, a slight inhibitory effect on tumor cell growth was obtained relative to the control, with TGI at the level of 5.6%. Thus, fusion proteins of the invention exert much stronger effect compared to TRAIL.

Figure 10:
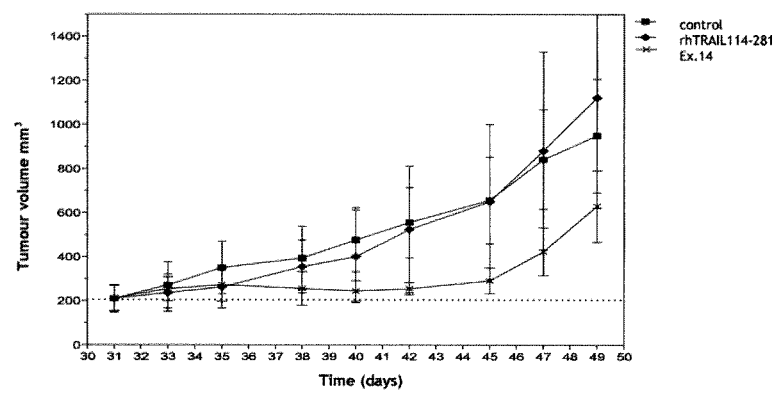
FIG. 10 presents tumor volume changes (% of initial stage) in Crl:SHO-PrkdcscidHrhr mice burdened with liver cancer PLC/PRF/5 treated with fusion protein of the invention of Ex. 14 compared to rhTRAIL114-281.
Figure 11:
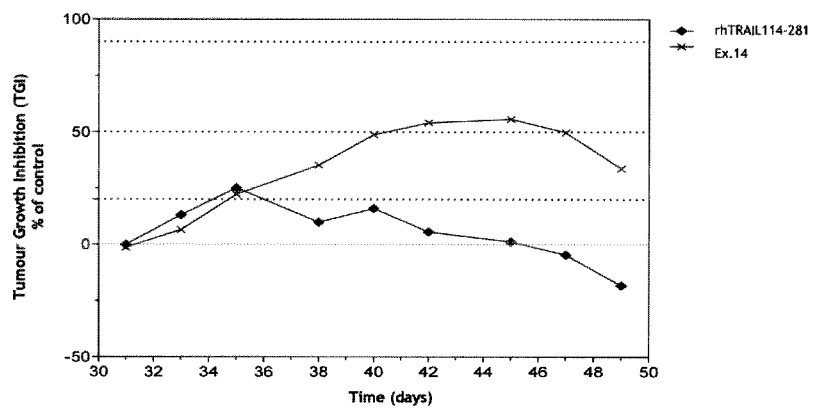
FIG. 11 presents the tumor growth inhibition values (% TGI) in Crl:SHO-PrkdcscidHrhr mice burdened with liver cancer PLC/PRF/5 treated with fusion protein of the invention of Ex. 14 compared to rhTRAIL114-281.

The experimental results obtained in mice CrLSHO-Prkdc$^{scid}$Hr$^{hr}$ burdened with PLC/PRF/5 liver cancer treated with fusion protein of the invention of Ex. 14 and comparatively with rhTRAIL114-281 are shown in FIG. 10 as a diagram of changes of the tumor volume and in FIG. 11 which shows tumor growth inhibition (% TGI) as the percentage of control.

The results of experiments presented in the graphs in FIGS. 10 and 11 show that administration of the fusion protein of the invention of Ex. 14 caused tumor PLC/PRF/5 growth inhibition, with TGI 34% relative to the control on 49$^{th}$ day of the experiment. For rhTRAIL114-281 used as the comparative reference, a slight inhibitory effect on tumor cell growth was obtained relative to the control, with TGI at the level of 18%. Thus, fusion proteins of the invention exert much stronger effect compared to TRAIL.

Figure 12:
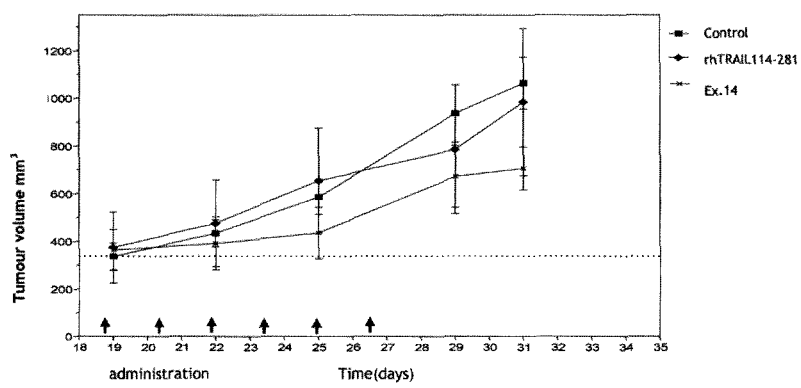
FIG. 12 presents tumor volume changes (% of initial stage) in Crl:SHO-PrkdcscidHrhr mice burdened with liver cancer HepG2, treated with fusion protein of the invention of Ex. 14 compared to rhTRAIL114-281.
Figure 13:
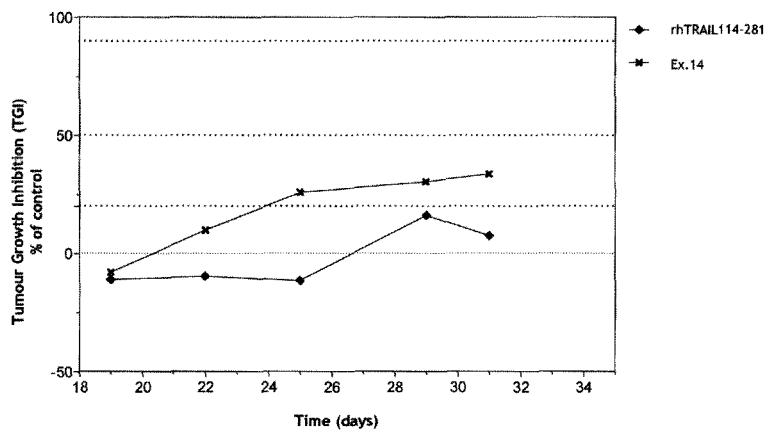
FIG. 13 presents the tumor growth inhibition values (% TGI) in Crl:SHO-PrkdcscidHrhr mice burdened with liver cancer HepG2 treated with fusion protein of the invention of Ex. 14 compared to rhTRAIL114-281.

The experimental results obtained in mice Crl:SHO-Prkdc$^{scid}$Hr$^{hr}$ burdened with HepG2 liver cancer treated with fusion protein of the invention of Ex. 14 and comparatively with rhTRAIL114-281 are shown in FIG. 12 as a diagram of changes of the tumor volume and in FIG. 13 which shows tumor growth inhibition (% TGI) as the percentage of control.

The results of experiments presented in the graphs in FIGS. 12 and 13 show that administration of the fusion protein of the invention of Ex. 14 caused tumor HepG2 growth inhibition, with TGI 33.6% relative to the control on 31 day of the experiment. For rhTRAIL114-281 used as the reference preparation, a slight inhibitory effect on tumor cell growth was obtained relative to the control, with TGI at the level of 7%. Thus, fusion proteins of the invention exert much stronger effect compared to TRAIL.

The tested fusion proteins did not cause significant side effects manifested by a decrease in body weight of mice (i.e. less than 10% of the baseline body weight). This shows low systemic toxicity of the protein.

The invention claimed is:

1. A fusion protein comprising:
   domain (a) which is a functional fragment of human Tumor Necrosis Factor-Related Apoptosis Inducing Ligand (hTRAIL) protein, wherein said fragment begins with an amino acid at a position not lower than hTRAIL95 and ends with the amino acid at position hTRAIL281, or a homolog of said functional fragment having at least 70% sequence identity; and
   domain (b) which is an immunostimulating effector peptide selected from the group consisting of pseudodimer of interferon gamma of SEQ ID NO: 19 and the pseudodimer of interferon alpha 2b of SEQ ID NO: 46;
   wherein domain (b) is attached at the C-terminus or N-terminus of domain (a)
   and wherein hTRAIL has the sequence set forth as SEQ ID NO: 16.

2. The fusion protein according to claim 1 wherein domain (a) comprises the fragment of hTRAIL protein that begins with an amino acid from the range hTRAIL95 to hTRAIL122, inclusive, and ends with the amino acid hTRAIL281.

3. A pharmaceutical composition, comprising as an active ingredient the fusion protein as defined in claim 2 in combination with a pharmaceutically acceptable carrier.

4. The fusion protein according to claim 2 wherein domain (a) is selected from the group consisting of fragments of hTRAIL95-281 that begin with an amino acid in position 95, 116, 120, 121 or 122.

5. A pharmaceutical composition, comprising as an active ingredient the fusion protein as defined in claim 4 in combination with a pharmaceutically acceptable carrier.

6. The fusion protein according to claim 1, which between domain (a) and domain (b) contains at least one domain (c) comprising a protease cleavage site selected from the group consisting of a sequence recognized by metalloprotease MMP, a sequence recognized by urokinase uPA, and combinations thereof.

7. A pharmaceutical composition, comprising as an active ingredient the fusion protein as defined in claim 6 in combination with a pharmaceutically acceptable carrier.

8. The fusion protein according to claim 6, wherein the sequence recognized by metalloprotease MMP is SEQ ID NO: 20, and the sequence recognized by urokinase uPA is SEQ ID NO: 21.

9. A pharmaceutical composition, comprising as an active ingredient the fusion protein as defined in claim 8 in combination with a pharmaceutically acceptable carrier.

10. The fusion protein according to claim 6, wherein domain (c) is a combination of the sequence recognized by metalloprotease MMP and the sequence recognized by urokinase uPA located next to each other.

11. A pharmaceutical composition, comprising as an active ingredient the fusion protein as defined in claim 10 in combination with a pharmaceutically acceptable carrier.

12. The fusion protein according to claim 6, which contains two domains (c) and between two domains (c) contains a domain (d) of a linker for attachment of a PEG molecule, wherein domain (d) has a sequence selected from the group consisting of SEQ ID NO: 22, SEQ ID NO: 23, SEQ ID NO: 24, and SEQ ID NO: 25.

13. The fusion protein according to claim 12 which additionally comprises a glycine-serine flexible steric linker between domains (a), (b), (c) or (d).

14. A pharmaceutical composition, comprising as an active ingredient the fusion protein as defined in claim 12 in combination with a pharmaceutically acceptable carrier.

15. The fusion protein according to claim 6 which additionally comprises a glycine-serine flexible steric linker between domains (a), (b) or (c).

16. The fusion protein according to claim 1 the amino acid sequence of which is selected from the group consisting SEQ ID NO: 12; SEQ ID NO: 13; SEQ ID NO: 14; SEQ ID NO: 15; and SEQ ID NO: 44.

17. A pharmaceutical composition, comprising as an active ingredient the fusion protein as defined in claim 1 in combination with a pharmaceutically acceptable carrier.

18. A method of treatment of cancer in a mammal comprising administration to the mammal in need thereof of an antineoplastic-effective amount of the fusion protein as defined in claim 1.

19. The method of claim 18, wherein the mammal is a human.

* * * * *